United States Patent
Hladio et al.

(10) Patent No.: US 11,321,849 B2
(45) Date of Patent: May 3, 2022

(54) SYSTEMS AND METHODS FOR TRACKER CHARACTERIZATION AND VERIFICATION

(71) Applicant: INTELLIJOINT SURGICAL INC., Kitchener (CA)

(72) Inventors: Andre Novomir Hladio, Waterloo (CA); Richard Tyler Fanson, Stoney Creek (CA); Luke Becker, Kitchener (CA); Arash Abadpour, Toronto (CA); Joseph Arthur Schipper, Kitchener (CA)

(73) Assignee: INTELLIJOINT SURGICAL INC., Kitchener (CA)

( * ) Notice: Subject to any disclaimer, the term of this patent is extended or adjusted under 35 U.S.C. 154(b) by 179 days.

(21) Appl. No.: 16/871,809

(22) Filed: May 11, 2020

(65) Prior Publication Data
US 2020/0273178 A1    Aug. 27, 2020

Related U.S. Application Data

(63) Continuation of application No. 16/592,008, filed on Oct. 3, 2019, now Pat. No. 10,650,536, which is a continuation of application No. 16/253,641, filed on Jan. 22, 2019, now Pat. No. 10,438,359, which is a continuation of application No. 15/606,723, filed on May 26, 2017, now Pat. No. 10,223,798.

(60) Provisional application No. 62/362,857, filed on Jul. 15, 2016, provisional application No. 62/354,355, filed on Jun. 24, 2016, provisional application No. 62/349,887, filed on Jun. 14, 2016, provisional application No. 62/342,366, filed on May 27, 2016.

(51) Int. Cl.
| | |
|---|---|
| *G06T 7/246* | (2017.01) |
| *A61B 34/20* | (2016.01) |
| *A61N 5/10* | (2006.01) |
| *A61B 17/00* | (2006.01) |
| *A61B 6/04* | (2006.01) |

(52) U.S. Cl.
CPC .............. *G06T 7/246* (2017.01); *A61B 34/20* (2016.02); *A61B 6/0487* (2020.08); *A61B 2017/00725* (2013.01); *A61B 2034/207* (2016.02); *A61B 2034/2055* (2016.02); *A61N 5/1049* (2013.01); *A61N 2005/1051* (2013.01); *A61N 2005/1059* (2013.01); *G06T 2207/30004* (2013.01); *G06T 2207/30204* (2013.01)

(58) Field of Classification Search
None
See application file for complete search history.

(56) References Cited

U.S. PATENT DOCUMENTS

| | | | |
|---|---|---|---|
| 7,613,361 B2 | 11/2009 | Anabuki et al. | |
| 7,831,082 B2* | 11/2010 | Holsing | A61B 90/36 382/131 |
| 8,781,162 B2* | 7/2014 | Zhu | G06T 7/75 382/103 |

(Continued)

*Primary Examiner* — Anand P Bhatnagar

(57) ABSTRACT

The present application relates to systems and methods used to characterize or verify the accuracy of a tracker comprising optically detectable features. The tracker may be used in spatial localization using an optical sensor. Characterization results in the calculation of a Tracker Definition that includes geometrical characteristics of the tracker. Verification results in an assessment of accuracy of a tracker against an existing Tracker Definition.

24 Claims, 34 Drawing Sheets

(56) References Cited

U.S. PATENT DOCUMENTS

| | | | |
|---|---|---|---|
| 9,341,704 B2* | 5/2016 | Picard | A61B 34/20 |
| 9,400,170 B2* | 7/2016 | Steffey | G01B 21/045 |
| 9,713,506 B2* | 7/2017 | Fanson | A61B 17/1703 |
| 9,881,375 B2* | 1/2018 | Gordon | G06T 7/85 |
| 10,013,808 B2* | 7/2018 | Jones | G06F 3/0346 |
| 2001/0039421 A1 | 11/2001 | Heilbrun et al. | |
| 2005/0256395 A1* | 11/2005 | Anabuki | G06T 7/246 |
| | | | 600/414 |
| 2006/0071946 A1* | 4/2006 | Anabuki | G06K 9/3216 |
| | | | 345/633 |
| 2009/0177081 A1* | 7/2009 | Joskowicz | A61B 90/13 |
| | | | 600/426 |
| 2009/0190826 A1* | 7/2009 | Tate | H04N 1/00087 |
| | | | 382/153 |
| 2010/0039421 A1* | 2/2010 | Toyomura | G09G 3/3208 |
| | | | 345/212 |
| 2010/0080417 A1* | 4/2010 | Qureshi | G06T 7/74 |
| | | | 382/103 |
| 2010/0328451 A1* | 12/2010 | Hotta | G06T 7/73 |
| | | | 348/135 |
| 2011/0052008 A1* | 3/2011 | Holsing | A61B 90/36 |
| | | | 382/103 |
| 2011/0174276 A1* | 7/2011 | Bierl | F02M 25/0809 |
| | | | 123/518 |
| 2011/0184276 A1 | 7/2011 | Lyon et al. | |
| 2012/0078418 A1* | 3/2012 | Borm | B25J 9/1692 |
| | | | 700/254 |
| 2013/0064427 A1* | 3/2013 | Picard | A61B 34/20 |
| | | | 382/103 |
| 2015/0085072 A1* | 3/2015 | Yan | A61N 5/1048 |
| | | | 348/43 |
| 2016/0005185 A1* | 1/2016 | Geissler | G06T 7/579 |
| | | | 348/47 |
| 2016/0171702 A1* | 6/2016 | Wittmeier | G01S 11/12 |
| | | | 382/103 |
| 2016/0220320 A1* | 8/2016 | Crawford | A61B 90/98 |
| 2016/0225192 A1* | 8/2016 | Jones | G06F 3/017 |

* cited by examiner

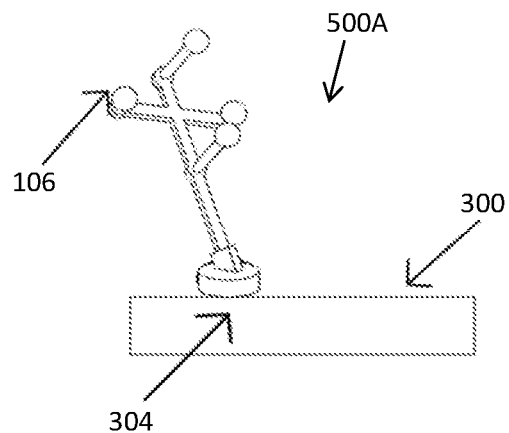 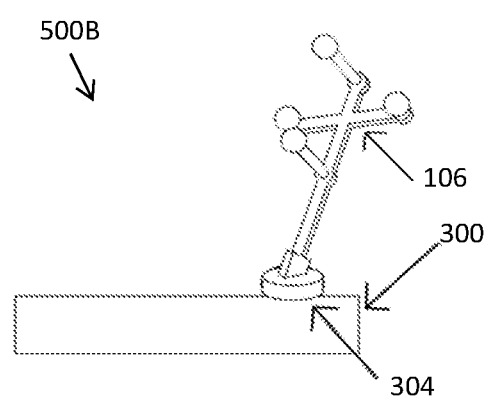
Fig. 5A        Fig. 5B
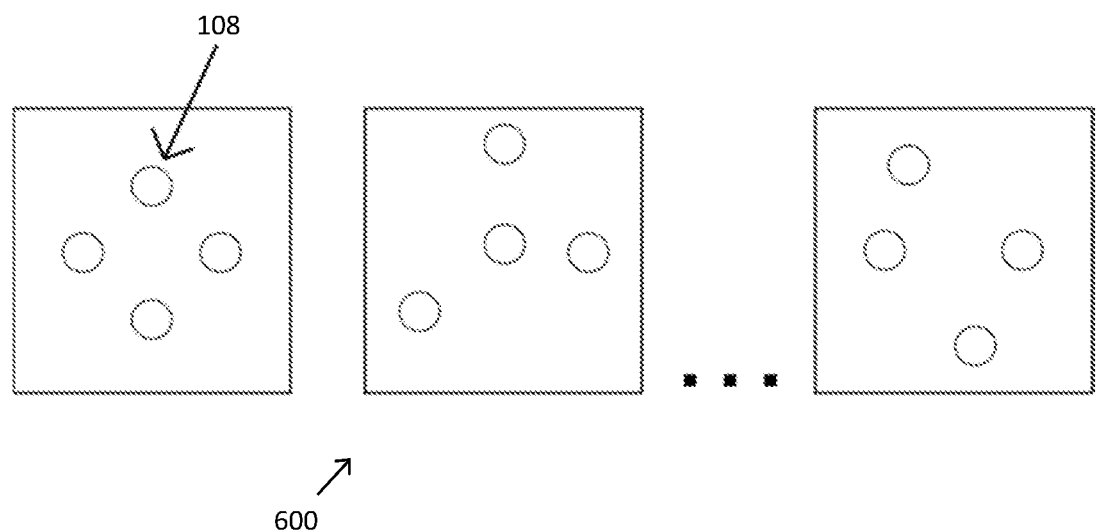
Fig. 6

SYSTEMS AND METHODS FOR TRACKER CHARACTERIZATION AND VERIFICATION

CROSS-REFERENCE TO RELATED APPLICATIONS

The present application is a continuation of prior U.S. patent application Ser. No. 16/592,008, filed Oct. 3, 2019 (issued as U.S. patent Ser. No. 10/650,536), and entitled, "Systems and Methods for Tracker Characterization and Verification" incorporated herein by reference, which prior application is a continuation of prior U.S. patent application Ser. No. 16/253,641, filed Jan. 22, 2019 (now U.S. patent Ser. No. 10/438,359), and entitled, "Systems and Methods for Tracker Characterization and Verification" incorporated herein by reference, which prior application is a continuation of prior U.S. patent application Ser. No. 15/606,723, filed May 26, 2017 (now U.S. Pat. No. 10,223,798), and entitled, "Systems and Methods for Tracker Characterization and Verification" incorporated herein by reference and which prior application claims the benefit of the following four US provisional applications, all having the same title and all incorporated herein by reference: Provisional Patent Application No. 62/342,366, filed May 27, 2016, entitled "Systems and Methods for Tracker Characterization and Verification"; Provisional Patent Application No. 62/349,887, filed Jun. 14, 2016; Provisional Patent Application No. 62/354,355, filed Jun. 24, 2016; and Provisional Patent Application No. 62/362,857, filed Jul. 15, 2016.

FIELD

The present application relates to trackers having optically detectable features for tracking objects in a space and more particularly to systems, methods and devices to calculate a Tracker Definition through characterization, or to verify the accuracy of a tracker with respect to a known Tracker Definition. Trackers may include those attached to bones, instruments or other objects in surgical localization systems.

BACKGROUND

Localization systems that use optical sensors to detect and measure a location of an object in space may rely on the assumption that the optically detectable features of an object (or of a tracker attached to the object) are spatially located in a known pattern or geometry. However, there are several drawbacks to relying on this assumption. The tracker or its optically detectable features may be damaged due to normal wear and tear causing deviations of its physical geometry. Repeated sterilization to allow use in a sterilized environment may lead to deformities in physical geometry that may not be caught through visual inspection. Such inaccuracies may result in incorrect pose calculation during localization.

BRIEF SUMMARY

There is a desire to obtain information about the spatial location of the optically detectable features that are being tracked or verify the accuracy of the features with respect to an expected geometry.

BRIEF DESCRIPTION OF DRAWINGS

Embodiments disclosed herein will be more fully understood from the detailed description and the corresponding drawings, which form a part of this application, and in which:

FIGS. 5A and 5B depict two views (from the perspective of a camera) of the tracker attached to different tracker mounting locations on a characterization jig comprising mounting locations configured to receive a tracker;

FIG. 6 shows a plurality of images from an optical feed of an optical camera;

Figure 1:
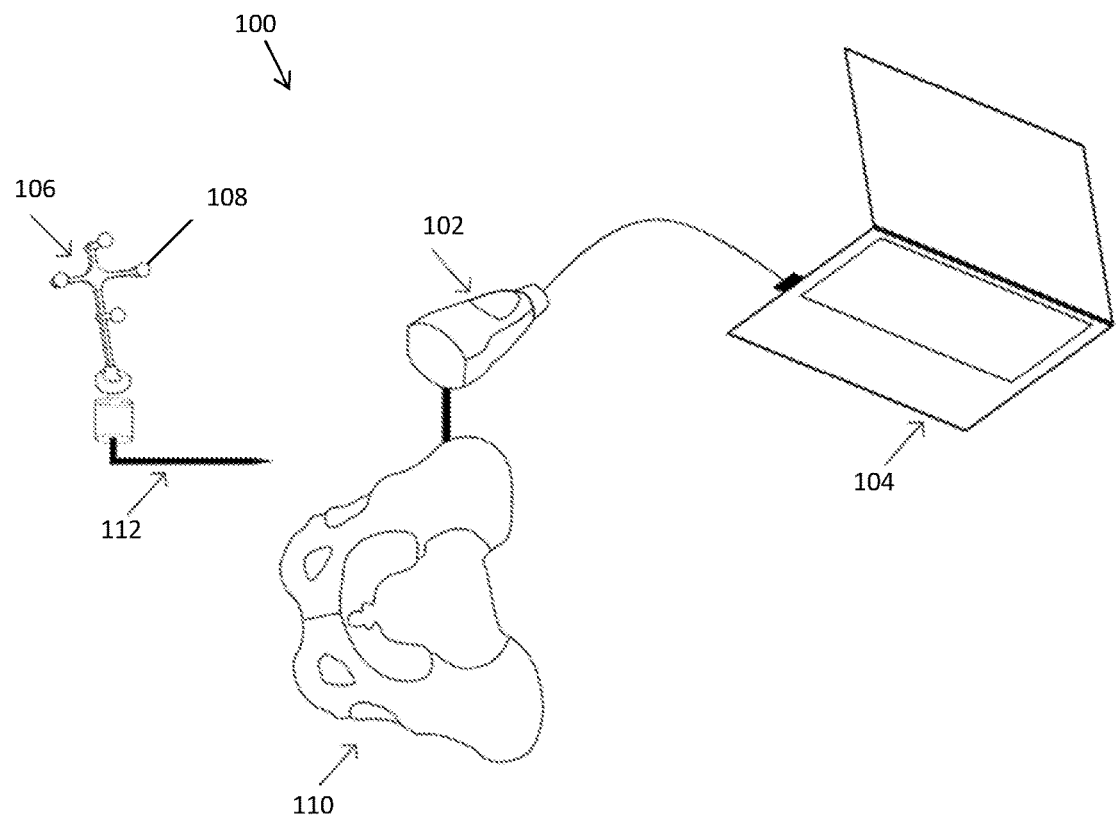
FIG. 1 depicts a localization system using a camera attached to a patient's anatomy and a tracker attached to a surgical instrument in accordance with the prior art.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION

Reference in the specification to "one embodiment", "preferred embodiment", "an embodiment", or "embodiments" means that a particular feature, structure, characteristic, or function described in connection with the embodiment is included in at least one embodiment, and may be in more than one embodiment. Also, such phrases in various places in the specification are not necessarily all referring to the same embodiment or embodiments.

A computing unit may comprise a laptop, workstation, or other computing device having at least one processing unit and at least one storage device such as memory storing software (instructions and/or data) as further described herein to configure the execution of the computing unit.

A localization system provides spatial localization of objects (instruments, implants, anatomical structures) with respect to another object such as a patient's anatomy. An example of a localization system is described herein. A miniature localization system comprising a sensor (such as an optical sensor e.g.: a monocular camera) is used to detect a tracker comprising optically detectable features of given shapes (e.g., spheres) arranged in a particular pattern or constellation. The optically detectable features may be passive (e.g. constructed from retroreflective materials) or active (e.g. LED light sources). The tracker has a base that may be used to mount the tracker on the object to be tracked. The base may comprise a kinematic mount that allows a repeatable connection between the tracker and the object. The system further comprises a computing unit that is in communication with the camera. The computing unit receives a real time feed of images from the camera, extracts the optically detectable features (e.g., spherical markers) and generates/calculates a six degrees of freedom (DOF) pose of the tracker in real-time. By knowing the spatial location of the optically detectable features (relative to each other), the computing unit is able to calculate the position of the tracker, and hence the object to which the tracker is attached. In order to calculate the pose of the tracker, one or more geometrical parameters related to the markers, such as the pattern in which the markers are arranged, the distance between two or more markers, the 3D geometry of the tracker, etc. are pre-loaded in to the computing unit. This pre-loaded information is called the Static Tracker Definition in this specification. This is the "expected" Tracker Definition: e.g. if the tracker is not physically deformed; if the optically detectable features are located where expected (by the computing unit); if the geometrical definition of the tracker conforms to mechanical specifications; etc. The Static Tracker Definition may be determined during the manufacturing process through adherence to strict tolerances described within the mechanical specification of the tracker. Assuming that the Static Tracker Definition accurately represents the physical tracker during a localization procedure, instructions executing on the computing unit can accurately calculate the pose of the tracker.

However, there are several drawbacks to relying on the assumption that the Static Tracker Definition accurately represents the physical tracker. If the tracker relies on individual markers being attached thereto, the accuracy of the physical tracker geometry depends on the manufacturing quality of the markers, the accuracy of installation of the markers on the tracker, etc. In addition, the tracker may be damaged due to normal wear and tear causing deviations of its physical geometry from its Static Tracker Definition. Repeated sterilization to allow use of the tracker in a sterilized environment may lead to deformities in its physical geometry that may not be caught through visual inspection. Inaccuracies in the Static Tracker Definition may result in incorrect pose calculation in the localization procedure.

There is a desire to obtain a new Tracker Definition for a given tracker quickly and accurately and/or to verify the accuracy of a tracker with respect to the Static Tracker Definition.

This specification describes two systems—one for localization and the other for characterization. It is to be understood that these may be unique systems that utilise the same hardware such as the camera to capture images and the computing unit to execute instructions. These systems may also be distinct units that use different hardware. It is also possible that these discrete systems communicate with each other to present a seamless user experience but optionally utilise the same hardware. Alternatively, the characterization system may be used separately from the localization system. For example, the characterization system may be used as part of quality control at a manufacturing site while manufacturing a localization system for use in a surgical setting. The hardware and software used to characterize the tracker may be completely distinct.

FIG. 1 illustrates a localization system 100 where a sensor comprising an optical sensor (e.g.: camera) 102 communicates with a computing unit 104. The terms "optical sensor" and "camera" are used interchangeably in this specification. Images of a tracker 106 comprising optically detectable features (e.g. markers) 108 are captured by the optical sensor 102. The pose (position and orientation) of the tracker 106 can be calculated by the computing unit 104 and spatial measurements (based on the pose of the tracker) may be displayed on a graphical user interface (GUI) of the computing unit 104. The optical sensor 102 may be a monocular camera. A monocular camera can be small and compact. It may be attached to a platform near the operating table on which the patient is located, to a tool or instrument used during surgery, or directly to the patient's anatomy 110. The optical sensor 102 may be attached to the platform through a kinematic mount mechanism. The kinematic mount mechanism may be on the camera 102 itself or on another holding mechanism such as a clamp that is configured to hold a camera 102 in place by restricting its movement. The computing unit 104 may use the pose of the target to further display relevant measurements. The tracker 106 may be attached to an object of interest, a surgical instrument 112 or to the anatomy of a patient 110.

A corresponding workflow 200 to calculate the pose of a tracker 106 in the localization system described above is illustrated in FIG. 2. The computing unit 104 receives a real time feed of images 202 from the optical sensor 102, accesses the Static Tracker Definition 204 (e.g. in memory 206) and performs Localization Operations 208 in order to calculate the pose of a tracker with respect to the optical sensor 102. The pose of the tracker 210 may then be used to provide the surgeon real-time intra-operative spatial measurements to aid the surgical procedure.

Figure 2:
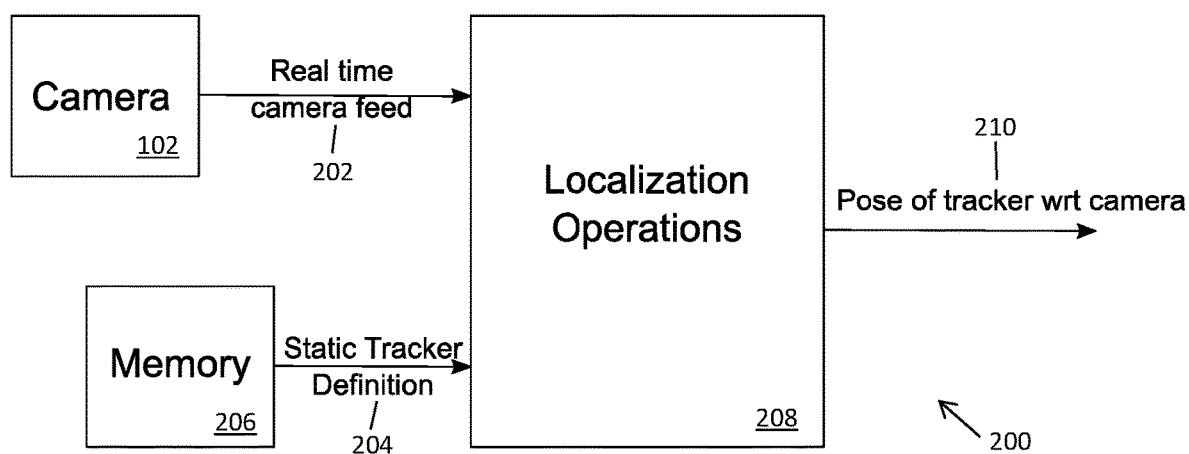
FIG. 2 is a block diagram depicting how to detect a pose of a tracker using an image feed of an optical camera and a Static Tracker Definition.

This specification discloses various embodiments of systems and methods and components for tracker characterization and verification. FIGS. 1-2 are relevant to all.

Tracker Characterization and Verification with Characterization Jig

Systems, methods and components for Tracker Characterization and Verification using Characterization Jig are described predominantly with reference to FIGS. 1-19.

There is disclosed a system comprising: a characterization jig comprising: a base; and a plurality of mounting locations on the base, each mounting location configured to selectively receive an optical sensor or a tracker; and a computer-readable storage device storing instructions which, when executed on a computing unit, configure the computing unit to: receive a first image of the tracker such that the tracker appears in a field of view of the optical sensor when one of the tracker and the optical sensor is attached to a first of the plurality of mounting locations on the characterization jig and another of the tracker and the optical sensor is attached to a platform; receive a second image of the tracker such that the tracker appears in the field of view of the optical sensor when at least one of the tracker and the optical sensor having been attached to the first mounting location is attached to a second of the plurality of mounting locations on the characterization jig and the other of the tracker and the optical sensor is attached to the platform; and calculating at least one of: a tracker definition using the first image, the second image, and a spatial relationship between the first of the plurality of mounting locations and the second of the plurality of mounting locations; and a tracker assessment parameter using the first image, the second image, the spatial relationship between the first of the plurality of mounting locations and the second of the plurality of mounting locations, and a static tracker definition.

The plurality of mounting locations on the characterization jig may be configured to receive optical sensors. The characterization jig may provide the platform for the tracker.

The plurality of mounting locations on the characterization jig may be configured to receive trackers. The characterization jig may provide the platform for the optical sensor. The system may further comprise the optical sensor, where the optical sensor is configured to attach to the platform for the optical sensor on the characterization jig.

The characterization jig may comprise an identifier to identify the spatial relationship between at least the first and the second of the plurality of mounting locations of the characterization jig. The identifier may be readable by the optical sensor.

The characterization jig may be made entirely of sterilisable material. It may be configured as a part of a lid of a tray of medical instruments.

At least one of the first or the second of the plurality of mounting locations on the characterization jig may be in a different plane than the other mounting locations.

User instructions may be displayed to a user on a display unit.

The computing unit may be configured to calculate the tracker assessment parameter and provide it to a display unit.

The computing unit may be configured to calculate the tracker assessment parameter and the system may further comprise a display unit to display the tracker assessment parameter.

At least one of the tracker definition and the tracker assessment parameter may be provided for a localization procedure.

There is disclosed a computer-implemented method comprising: receiving, by at least one computing unit, a first image of a tracker appearing in a field of view of an optical sensor when one of the tracker and the optical sensor is attached to a first mounting location on a characterization jig comprising a base and a plurality of mounting locations and another of the tracker and the optical sensor is attached to a platform; receiving, by the at least one computing unit, a second image of the tracker when the one of the tracker and the optical sensor having been attached to the first mounting location is attached to a second mounting location on the characterization jig such that the tracker appears in the field of view of the optical sensor and the other of the tracker and the optical sensor is attached to the platform; and calculating, by the at least one computing unit, at least one of: a tracker definition using the first image, the second image, and a spatial relationship between the first mounting location and the second mounting location; and a tracker assessment parameter using the first image, the second image, the spatial relationship between the first mounting location and the second mounting location, and a static tracker definition.

When the method calculates the tracker definition the method may provide spatial measurements based on a pose between the optical sensor and the tracker for intra-operative localization with respect to an anatomy of a patient.

There is provided a computer-implemented method comprising: receiving, by at least one computing unit, a first image of the tracker when the tracker is attached to a first of the plurality of mounting locations on a characterization jig comprising a plurality of mounting locations when the tracker is appearing in the field of view of the optical sensor attached to a platform; receiving, by the at least one computing unit, a second image of the tracker when the tracker is attached to a second of the plurality of mounting locations on the characterization jig when the tracker is appearing in the field of view of the optical sensor attached to the platform; and calculating, by the at least one computing unit, a tracker base geometry using the first image, the second image and a sensor tracker mount spatial relationship.

There is disclosed a computer-implemented method comprising: calculating, by at least one computing unit, a sensor tracker mount spatial relationship between an optical sensor and a characterization jig using additional features of the characterization jig, the characterization jig comprising a base and a plurality of mounting locations; receiving, by the at least one computing unit, a first image of the tracker when the tracker is attached to a first of the plurality of mounting locations on the characterization jig when the tracker is appearing in the field of view of the optical sensor attached to the platform; receiving, by the at least one computing unit, a second image of the tracker when the tracker is attached to a second of the plurality of mounting locations on the characterization jig when the tracker is appearing in the field of view of the optical sensor attached to the platform; and calculating, by the at least one computing unit, a tracker base geometry using the first image, the second image and the sensor tracker mount spatial relationship.

There is disclosed a system comprising: a characterization jig: a base; a plurality of mounting locations; and at least three divots; and a computer-readable storage medium storing instructions which, when executed on a computing unit, configure the computing unit to: receive divot image data comprising at least three images of a tracker attached to a calibrated probe while the tracker is appearing in a field of view of an optical sensor, the optical sensor attached to a platform, when the probe with the tracker attached to it is placed in each of at least three of the divots on the characterization jig; calculate a sensor tracker mount spatial relationship using the divot image data and a divot tracker mount spatial relationship; receive a first image of the tracker when the tracker is attached to a first of the plurality of mounting locations on the characterization jig when the tracker is appearing in the field of view of the optical sensor attached to the platform; receive a second image of the tracker when the tracker is attached to a second of the plurality of mounting locations on the characterization jig and when the tracker is appearing in the field of view of the optical sensor attached to the platform; and calculate a tracker base geometry using the first image, the second image and the sensor tracker mount spatial relationship.

The computing unit may be configured to calculate a tracker definition.

The computing unit may be configured to, before capturing the divot image data, calibrate a tip of the probe by pivoting the probe, having an attached tracker, about a fixed point while the optical sensor captures images of the tracker appearing in the field of view, and calculate the tip of the probe by executing center of rotation operations.

The computing unit may be further configured to include the tracker base geometry to a tracker definition.

There is disclosed a computer-implemented method comprising: receiving, by at least one computing unit, divot image data comprising at least three images of a tracker attached to a calibrated probe while the tracker is appearing in a field of view of an optical sensor, the optical sensor attached to a platform, when the probe with the tracker attached to it is placed in each of at least three divots on a characterization jig comprising a base and a plurality of mounting locations; calculating, by the at least one computing unit, a sensor tracker mount spatial relationship using the divot image data and a divot tracker mount spatial relationship; receiving, by the at least one computing unit, a first image of the tracker when the tracker is attached to a first of the plurality of mounting locations on the characterization jig when the tracker is appearing in the field of view of the optical sensor attached to the platform; receiving, by the at least one computing unit, a second image of the tracker when the tracker is attached to a second of the plurality of mounting locations on the characterization jig when the tracker is appearing in the field of view of the optical sensor attached to the platform; and calculating, by the at least one computing unit, a tracker base geometry using the first image, the second image and the sensor tracker mount spatial relationship.

The method may further comprise, before capturing divot image data, calibrating a tip of the probe by pivoting the probe, having an attached tracker, about a fixed point while the optical sensor captures images of the tracker appearing in the field of view, and the computing unit further configured to calculate the tip of the probe by executing center of rotation operations. The method may include calculating a tracker definition. The method may include including the tracker base geometry to a tracker definition.

There is disclosed a system comprising: a characterization jig: a base; a plurality of mounting locations; and at least three or more divots; and a computer-readable storage medium storing instructions which, when executed on a computing unit, configure the computing unit to: receive divot image data comprising at least three images of a tracker attached to a platform while the tracker is appearing in a field of view of an optical sensor, the optical sensor attached to a calibrated probe, when the probe with the optical sensor attached to it is placed in each of at least three of the plurality of divots on the characterization jig; calculate a tracker sensor mount spatial relationship using the divot image data and a divot sensor mount spatial relationship; receive a first image of the tracker when the optical sensor is attached to a first of the plurality of mounting locations on the characterization jig when the tracker attached to the platform is appearing in the field of view of the optical sensor; receive a second image of the tracker when the optical sensor is attached to a second of the plurality of mounting locations on the characterization jig when the tracker attached to the platform is appearing in the field of view of the optical sensor; and calculate a sensor mount spatial relationship using the first image, the second image and the tracker sensor mount spatial relationship.

There is disclosed a computer-implemented method to characterize a plurality of trackers simultaneously comprising: receiving, by at least one computing unit, a first image of the plurality of trackers when the trackers are in a fixed positional relationship to one another and appear simultaneously in a field of view of an optical sensor, the optical sensor attached to a first of a plurality of sensor mounting locations on a characterization jig, the characterization jig further comprising a base; and receiving, by at least one computing unit, a second image of the plurality of trackers when the trackers are in the fixed positional relationship to one another and appear simultaneously in the field of view of the optical sensor, the optical sensor attached to a second of the plurality of sensor mounting locations on the characterization jig; and calculating, by the at least one computing unit, a Tracker Definition for each tracker using the first image, the second image, information to distinguish the plurality of trackers and a spatial relationship between the first and the second of the plurality of sensor mounting locations on the characterization jig.

There is disclosed a system comprising: a characterization jig comprising: a base; and a plurality of mounting locations on the base; and a computer-readable storage medium storing instructions which, when executed on a computing unit, configure the computing unit to: receive a first image of a plurality of trackers when the trackers are in a fixed positional relationship to one another and appear simultaneously in a field of view of an optical sensor, the optical sensor attached to a first of the plurality of sensor mounting locations on the characterization jig; receive a second image of the plurality of trackers when the trackers are in the fixed positional relationship to one another and appear simultaneously in the field of view of the optical sensor, the optical sensor attached to a second of the plurality of sensor mounting locations on the characterization jig; and calculate a tracker definition for each tracker using the first image, the second image, information to distinguish the plurality of trackers and a spatial relationship between the first and the second of the plurality of sensor mounting locations on the characterization jig.

There is disclosed a computer-implemented method comprising: receiving, by at least one computing unit, a first image of a tracker appearing in a field of view of an optical sensor when the optical sensor is attached to a platform and the tracker is attached to a first tracker mounting location on a characterization jig, the characterization jig comprising a base and a plurality of tracker mounting locations; receiving a second image of the tracker when the tracker is attached to a second tracker mounting location on the characterization jig such that the tracker appears in the field of view of the optical sensor; and calculating at least one of: a tracker definition using the first image, the second image, and an inter tracker mount spatial relationship; and a tracker assessment parameter using the first image, the second image, the inter tracker mount spatial relationship, and a static tracker definition.

There is disclosed a system comprising: a characterization jig comprising: a base; and a plurality of tracker mounting locations on the base, each tracker mounting location configured to receive a tracker; and a computer-readable storage device storing instructions which, when executed on a computing unit, configure the computing unit to: receive a first image of a tracker when the tracker appears in a field of view of an optical sensor, the optical sensor attached to a platform and the tracker is attached to a first tracker mounting location on the characterization jig; receive a second image of the tracker when the tracker is attached to a second tracker mounting location on the characterization jig when the tracker appears in the field of view of the optical sensor; calculate at least one of a tracker definition using the first image, the second image, and an inter tracker mount spatial relationship; and a tracker assessment parameter using the first image, the second image, the inter tracker mount spatial relationship, and a static tracker definition.

There is disclosed a computer-implemented method comprising: receiving a first image of a tracker when the tracker appears in a field of view of an optical sensor, the tracker attached to a platform and the optical sensor attached to a first sensor mounting location on a characterization jig, the characterization jig comprising a base and a plurality of sensor mounting locations; receiving a second image of the tracker when the sensor is attached to a second sensor mounting location on the characterization jig when the tracker appears in a field of view of the optical sensor; and calculating at least one of: a tracker definition using the first image, the second image, and an inter sensor mount spatial relationship; and a tracker assessment parameter using the first image, the second image, the inter sensor mount spatial relationship, and a static tracker definition.

There is disclosed a system comprising: a characterization jig comprising: a base; and a plurality of sensor mounting locations on the base, each sensor mounting location configured to receive an optical sensor; and a computer-readable storage device storing instructions which, when executed on a computing unit, configure the computing unit to: receive a first image of a tracker when the tracker appears in a field of view of an optical sensor, the tracker attached to a platform and the optical sensor attached to a first sensor mounting location on the characterization jig; receive a second image of the tracker when the tracker appears in the field of view of the optical sensor, the tracker attached to the platform and the optical sensor attached to a sensor second mounting location on the characterization jig; and calculate at least one of a tracker definition using the first image, the second image, and an inter sensor mount spatial relationship; and a tracker assessment parameter using the first image, the second image, the inter sensor mount spatial relationship, and a static tracker definition.

It is understood that in any system described herein that includes a computer storage medium additional components may be present such as a computing unit, an optical sensor, and one or more targets, etc.

A characterization system that comprises a characterization jig may be used with the components of a localization system such as a sensor (e.g., a camera) and a tracker with optically detectable features (e.g., markers). The camera may be the same hardware used for localization or may be a part of a computing unit or laptop e.g., a webcam on a laptop. The characterization jig may be used to characterize a tracker (i.e. compute a current Tracker Definition) or to verify the accuracy of a tracker with respect to a previously defined Tracker Definition. In one example, the characterization jig comprises at least two mounting locations upon which a tracker can be attached. Two objects are "attached" when both are in contact with each other to form a connection and there is a holding mechanism to enforce the connection. The attachment may be rigid and removable, for example, selectively removable. It may also be repeatable by virtue of the type of mechanism used for attachment, for e.g. a kinematic mount. The jig may be made of sterilisable material to allow use within an operating room or any such sterilized environment. The jig may optionally comprise a mounting location for a camera such that the camera can obtain a pose measurement of the tracker while the tracker is attached to any of the tracker mounting locations. Alternatively, the camera may be attached to a platform that is optionally a part of the characterization jig. The geometry of the characterization jig is known. This implies that the physical shape, size, features etc. of the characterization jig are known since the jig may be manufactured under strict tolerances. The examples used in this specification utilize a known spatial relationship between the mounting locations of the tracker and therefore, between the corresponding poses of the tracker. This known spatial relationship or any of the other geometrical characteristics may be pre-loaded into the memory of the computing unit of the characterization system (e.g. as a hard-coded value, as a 3D model, etc.) and used in the calculation of the Tracker Definition or the verification of the accuracy of a tracker.

This specification repeatedly references the spatial relationship between multiple components, and uses the following nomenclature. The difference in position and orientation (in up to 6 degrees of freedom) of two components is referred to the spatial relationship between Component_1 and Component_2, and labelled as Component_1 Component_2 Spatial Relationship. The specification also refers to the spatial relationship between multiple instances of the same component as Inter Component Spatial Relationship.

To verify the accuracy of a tracker, the camera captures images specifically for characterization (also called "image data" in this specification) of the tracker when the tracker is attached to the tracker mounting locations on the characterization jig. Using a known spatial characteristic of the characterization jig (such as an Inter Tracker Mount Spatial Relationship between the tracker mounting locations), the computing unit compares image data of the tracker when the tracker is attached to each mounting location with image data that is calculated using the pre-loaded Static Tracker Definition. The computing unit may also calculate a new Tracker Definition and compare it with the Static Tracker Definition. This comparison results in a determination of accuracy of the tracker. Alternatively, the new Tracker Definition may be used as an input in a localization procedure. The characterization and verification processes are further described below.

Figure 3:
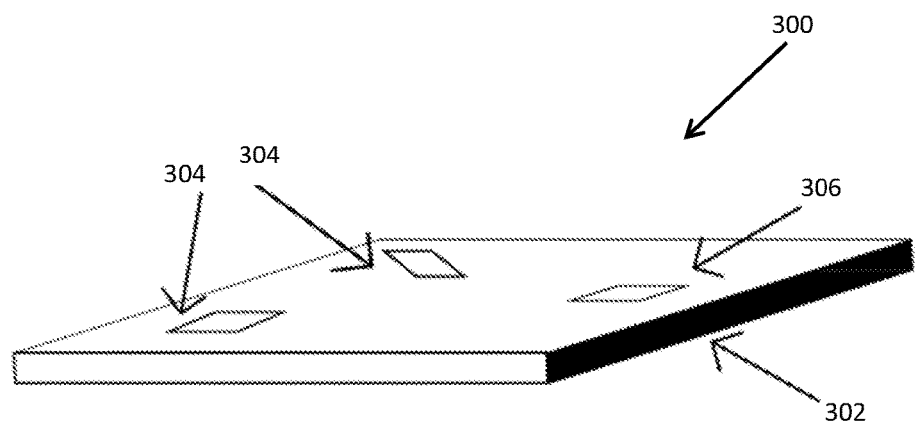
FIG. 3 shows an example of a characterization jig with a plurality of mounting locations.
Figure 4:
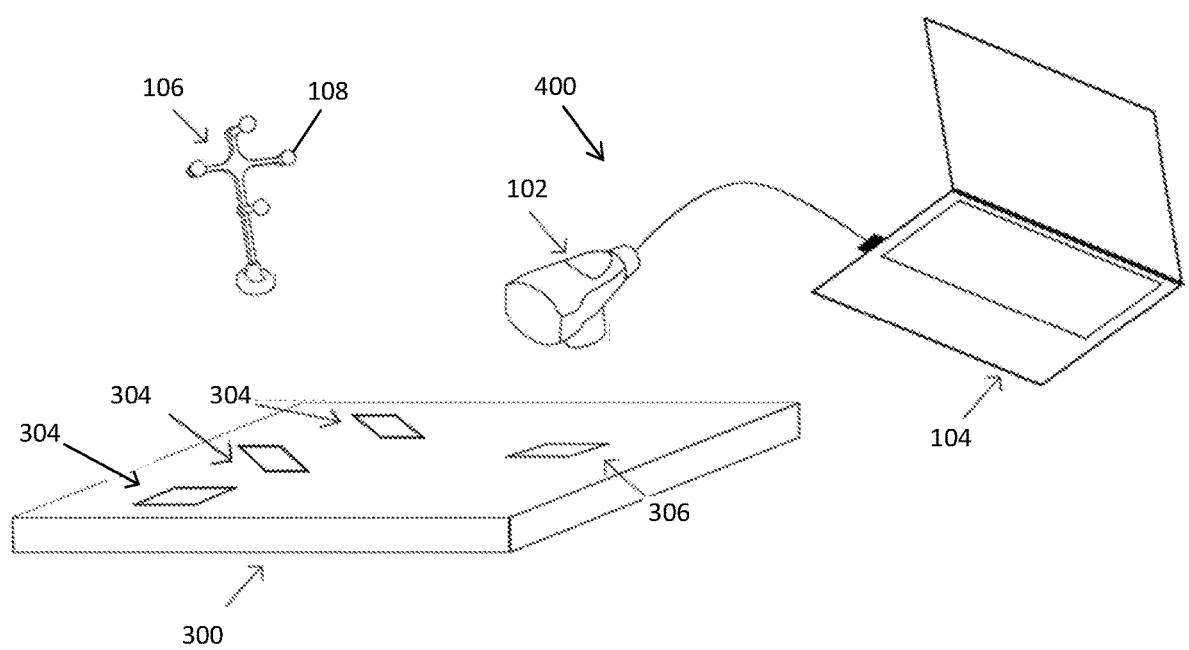
FIG. 4 shows an embodiment of a localization system comprising a camera and a tracker being used with a characterization jig of a characterization system where the jig comprises mounting locations for the camera and tracker.

Reference is now made to FIG. 3 showing a characterization jig 300 comprising a rigid base 302 and at least two mounting locations 304 for a tracker (e.g. 106). The characterization jig 300 may optionally comprise a platform for a camera or a camera mounting location 306. FIG. 4 shows a use of an embodiment of a characterization jig 300 along with a localization system 400 and a tracker 106. The camera 102 is in communication with the computing unit 104. An exemplary characterization jig 300 shown in this figure depicts a mounting location 306 on the characterization jig 300 for a camera 102 as well as three mounting locations 304 on the same base for tracker 106 with optically detectable features 108.

The Inter Tracker Mount Spatial Relationship may be stored in memory 206 as a numerical representation of the relative poses between the mounting locations represented as rotation matrices, quaternions, euler angles, translational vectors, Cartesian distances etc. The characterization jig 300 may be manufactured to meet a specific Inter Tracker Mount Spatial Relationship, and the same spatial relationship may be accessible to the computing unit 104. For example, the numerical representation of this spatial relationship may be data stored in memory 206, preferably in a manner that prevents or reduces the possibility of deletion. There may be an identifier (not shown) such as a barcode, QR-code, URL, etc. on the characterization jig 300 itself that identifies the Inter Tracker Mount Spatial Relationship. The identifier may be read using the optical camera 102 and used to look up the Inter Tracker Mount Spatial Relationship that is stored in memory 206 or remotely such as at a server on a network.

In an exemplary application of the disclosed characterization system, when optical sensor 102 is attached to its mounting location 306 and its field of view is directed towards tracker 106 attached to a tracker mounting location 304 on characterization jig 300, optical sensor 102 is able to capture image data 600 (See FIG. 6) of tracker 106 (including at least optically detectable features 108). Multiple mounting locations 304 are provided and the Inter Tracker Mount Spatial Relationship between tracker mounting locations 304 is known to computing unit 104 that is in communication with camera 102. As the number of tracker mounting locations 304 increases, a person skilled in the art will appreciate that the level of accuracy of the resulting calculations may improve. Tracker mounting locations 304 provide multiple vantage points to camera 102 such that the view of tracker 106 (as seen from the camera attached to its mounting location) is substantially different in each location. Computing unit 104 executes instructions to receive at least one image from camera 102 while tracker 106 is in each mounting location 304 to identify optically detectable features 108 (e.g. markers) in the image data 600. Using the known Inter Tracker Mount Spatial Relationship between each tracker mounting location 304 on characterization jig 300, computing unit 104 generates a Tracker Definition for tracker 106. This may be done by performing an optimization operation using the Inter Tracker Mount Spatial Relationship as an optimization constraint. A person skilled in the art will appreciate that a larger quantity of image data 600 from the camera may be acquired in order to improve calculations in terms of speed, accuracy, robustness to errors (especially errors caused by a user), etc. The new Tracker Definition may then be provided to a localization procedure e.g., a navigated surgical procedure.

FIGS. 5A and 5B illustrate two views 500A and 500B of jig 300 having tracker 106 mounted in two different tracker mounting locations 304 similar to the perspective of camera 102. Note that the pose of the tracker is substantially different in each tracker mounting location 304 and characterization jig 300 does not provide the platform for the camera 102. This provides computing unit 104 with image data 600 from various vantage points. Reference is now made to FIG. 6 which depicts multiple instances of image data 600 comprising images of markers 108 of tracker 106 within a field of view of camera 102. Each instance of image data 600 corresponds to tracker 106 being attached at a different tracker mounting location 304.

Figure 7A:
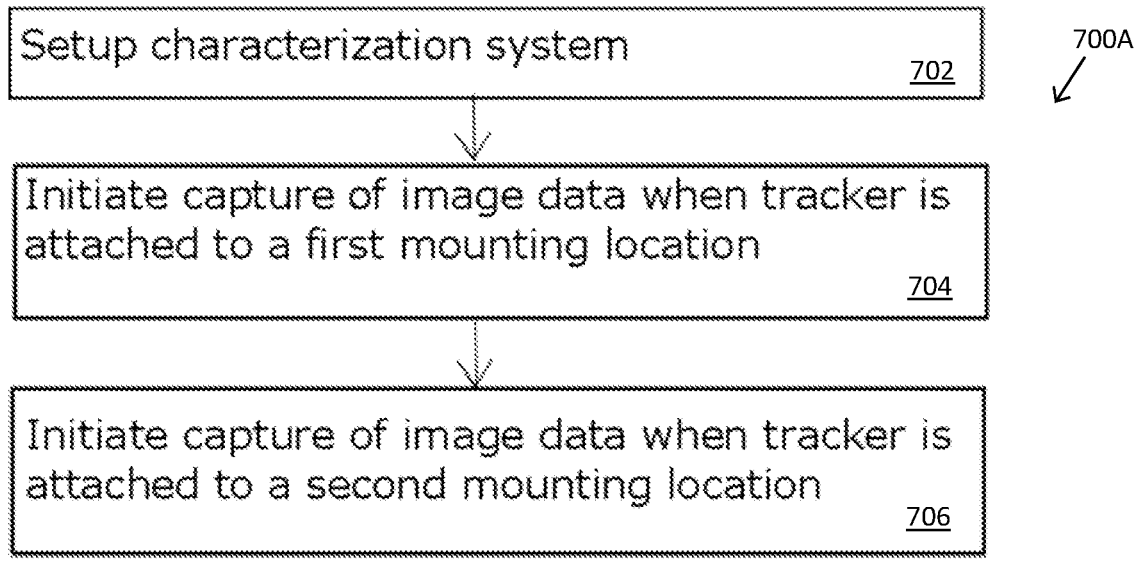
FIGS. 7A and 7B are flowcharts showing workflow and other computer operations to generate a Tracker Definition.
Figure 7B:
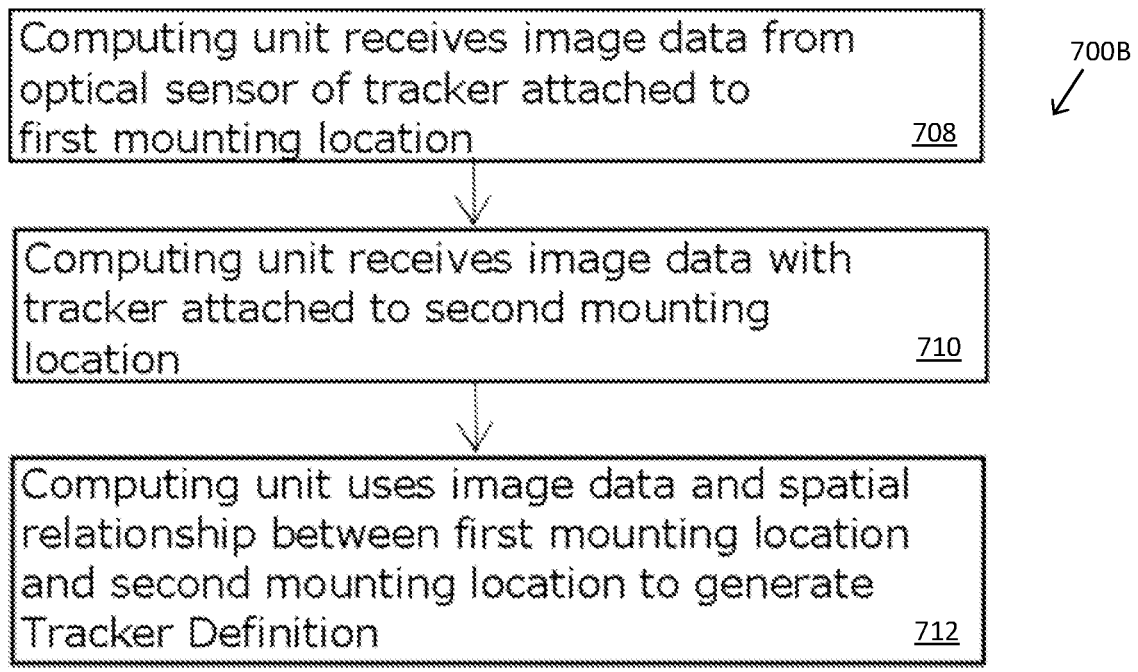

Reference is now made to flowcharts FIGS. 7A and 7B showing workflow and other computer operations. A workflow 700A executing on a computing unit 104 directs a user to capture image (image data 600). At 702, operations by computing unit 104 direct the user to set up the characterization system by attaching camera 102 to sensor mounting location 306. The user is instructed (at 704) by workflow 700A (e.g. via a graphical user interface and/or audible instructions or otherwise (not shown)) to attach tracker 106 on a first mounting location 304 and to initiate the capture of image data 600. The user is then instructed (at 706) to attach tracker 106 to a second mounting location 304 and to initiate the capture image data 600 for characterization. The user may be instructed to initiate the capture of data or the data may be captured automatically using methods like stability detection described further below. In a corresponding computer-implemented method 700B, computing unit 104 receives (at 708 and 710) image data 600 from camera 102 (attached to optical sensor mounting location 306) of tracker 106 where tracker 106 is sequentially attached to at least two tracker mounting locations. Computing unit 104 may automatically capture image data 600 via stability detection, or may receive it manually via a human machine interface, such as a button on camera 102 or a command through computing unit 104 or foot pedal. In order to implement stability detection, computing unit 104 may capture image data 600 when optically detectable features 108 in image data 600 appear to be stable for a substantial period of time (as appropriate for the application). Using image data 600 and a known spatial relationship, such as the Inter Tracker Mount Spatial Relationship between the various tracker mounting locations 304, computing unit 104 calculates a Tracker Definition 712. This Tracker Definition can then be used in localization procedures to calculate pose 210 of tracker 106. It is understood that optical sensor 102 and tracker 106 locations may be reversed such that optical sensor 102 is moved among a plurality of sensor mounting locations while tracker 106 remains attached to a single tracker mounting location 304.

The instructions executing on computing unit 104 preferably include error checks to ensure that the tracker 106 is correctly attached to the appropriate mounting locations 304 during the workflow. This error check may come in the form of an error residual of an optimization operation that uses image data 600 as an input. If the error residual is too high, computing unit 104 may prompt the user to verify the accuracy of the position of tracker 106 on tracker mounting location 304. Computing unit 104 may further provide the Tracker Definition to a localization system.

Figure 8:
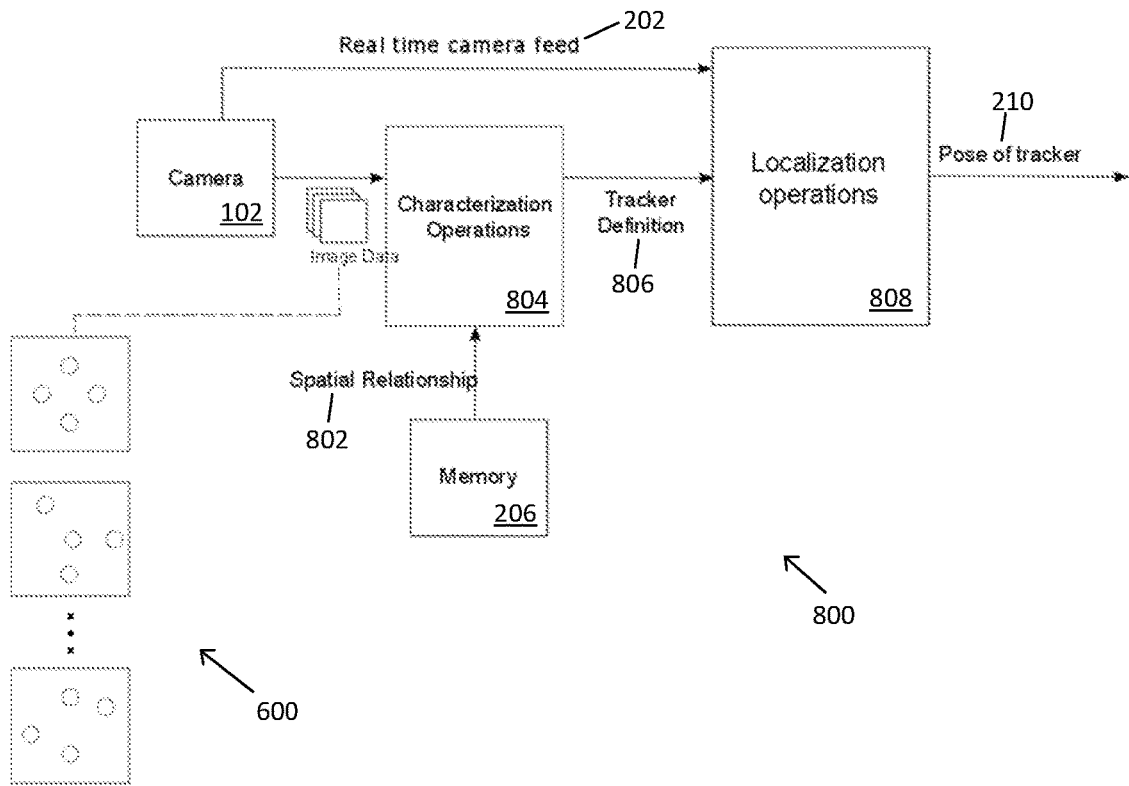
FIG. 8 shows a block diagram depicting a characterization operation providing input to localization operations as an example for clarity.

FIG. 8 shows a block diagram depicting a characterization operation providing input to localization operations. Computing unit 104 receives image data 600 from optical sensor 102 of tracker 106 attached to characterization jig 600 and receives from memory 206 a known spatial relationship, such as Inter Tracker Mount Spatial Relationship 802. Computing unit 104 performs characterization operations 804 using image data 600 and known spatial relationship 802 to determine a tracker definition 806. Computing unit 104 then receives a real time feed of images 202 from optical sensor 102 and tracker definition 806 and performs Localization Operations 808 in order to calculate the pose 210 of a tracker with respect to optical sensor 102.

Tracker Verification

Figure 9A:
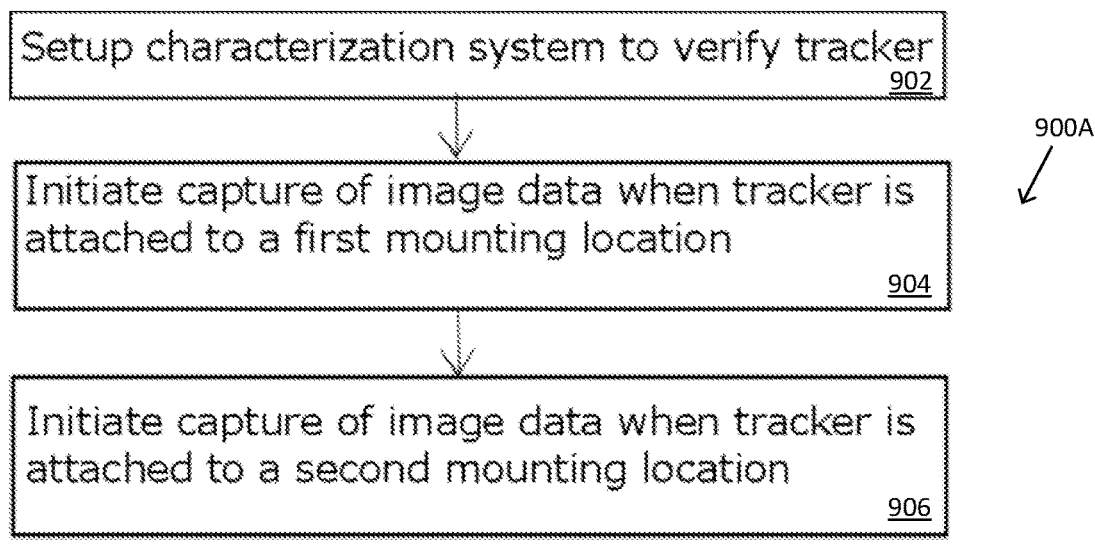
FIGS. 9A and 9B are flowcharts showing workflow and other computer operations to verify the accuracy of a tracker.
Figure 9B:
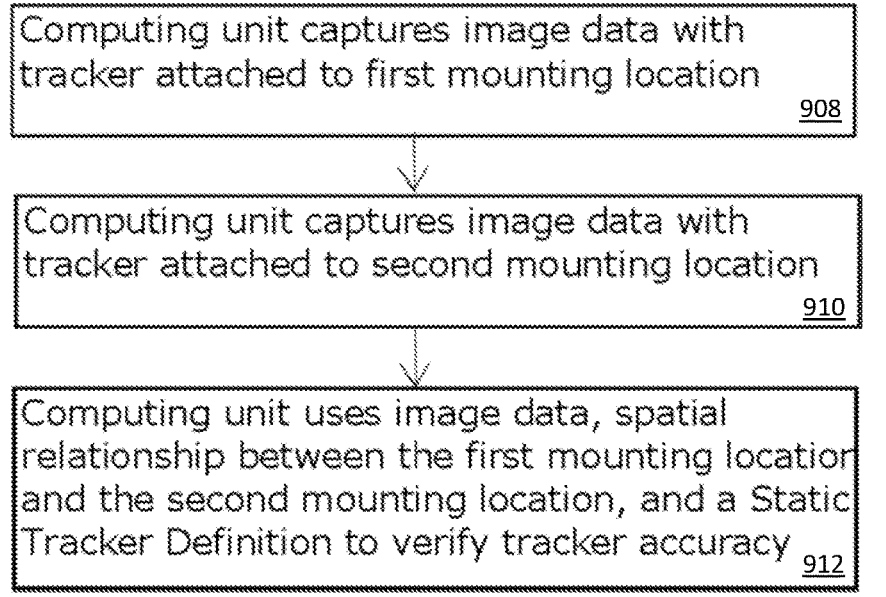

During tracker verification, computing unit 104 verifies the accuracy of a tracker with respect to a Static Tracker Definition 204. Reference is now made to FIGS. 9A and 9B which are flowcharts showing workflow and other computer operations 900A and 900B executing on computing unit 104. At 902 operations direct (e.g. via a GUI or other human machine interface) a user to set up the characterization system by attaching camera 102 to a sensor mounting location 306. The user is further instructed by the workflow at 904 and 906 to attach tracker 106 consecutively on a first mounting location 304 and a second mounting location 304 in order to capture image data 600 for verification at two locations. It is understood that more captures at more locations may be instructed and performed. A corresponding computer-implemented method 900B is illustrated in FIG. 9B comprising steps 908, 910 and 912. Computing unit 104 captures image data 600 from camera 102 attached to a sensor mounting location 306 of tracker 106 attached to a first tracker mounting location 304, and a second tracker mounting location 304. Using a known Inter Tracker Mount Spatial Relationship between tracker mounting locations 304, computing unit 104 verifies the accuracy of a tracker. This may be done in several ways such as by analyzing image data 600 associated with tracker 106 for consistency with a given Static Tracker Definition 204 (e.g., expected image data 600 using the Static Tracker Definition 204 may be generated by computing unit 104, and compared with actual image data 600 captured by the camera 102), by calculating a Tracker Definition 806 for tracker 106 and comparing the results with Static Tracker Definition 204, etc.

Figure 10:
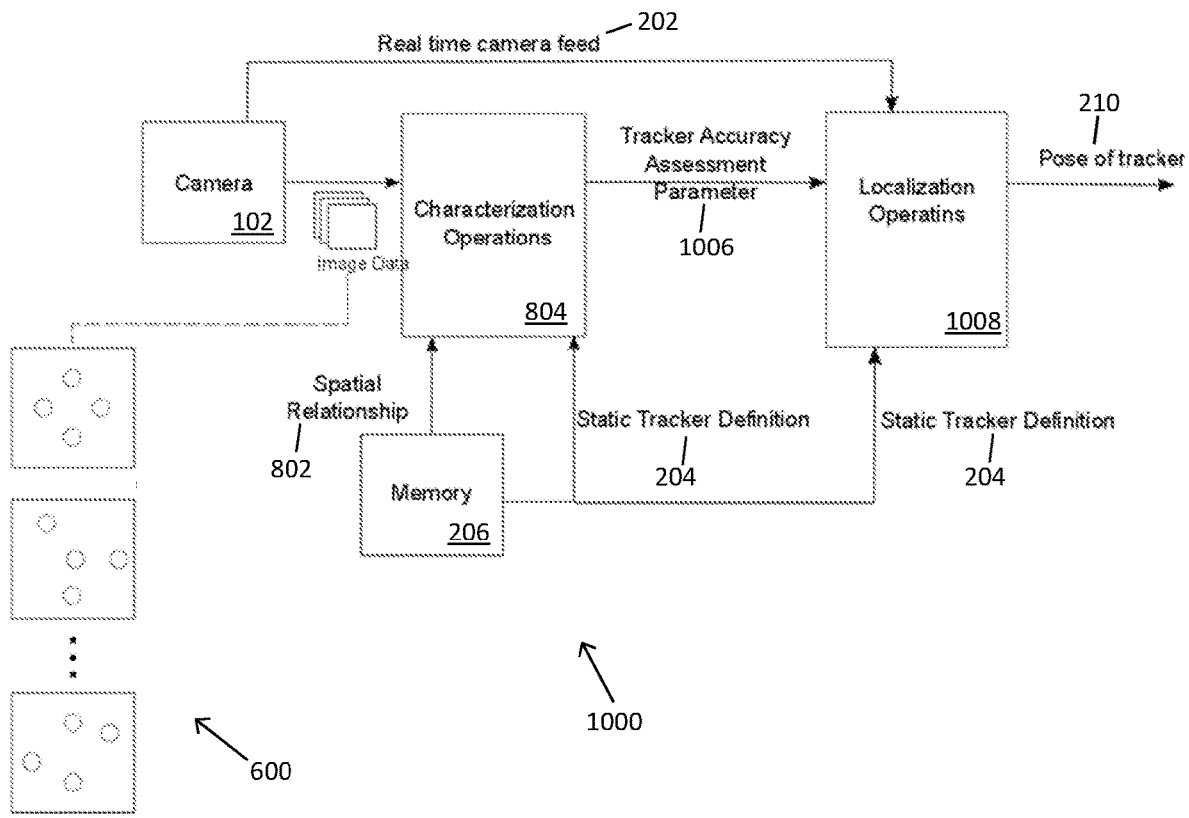
FIG. 10 shows a block diagram depicting a verification operation (part of characterization operations) that provides a Tracker Assessment Parameter to a localization operation as an example for clarity.

It is possible that for some surgical applications, deviation of tracker 106 from a Static Tracker Definition 204 is unacceptable. The system may generate a Tracker Assessment Parameter to quantify this deviation. This Tracker Assessment Parameter may then be used by computing unit 104 during a localization procedure to determine whether the tracker 106 being used is accurate or not. Some of the examples of how the Tracker Assessment Parameter is presented could be a Boolean flag, a single numerical value or multiple numerical values associated with how closely Tracker Definition 806 matches Static Tracker Definition 204, etc. FIG. 10 shows a block diagram depicting a verification operation 1000 (part of characterization operations) that provides a Tracker Assessment Parameter 1006 to a localization operation 1008. The localization system further calculates a pose 210 of the tracker 210. As described previously, the characterization operations 804 and localization operations 1008 may be executed in the form of instructions on the same computing unit 104.

Figure 11A:
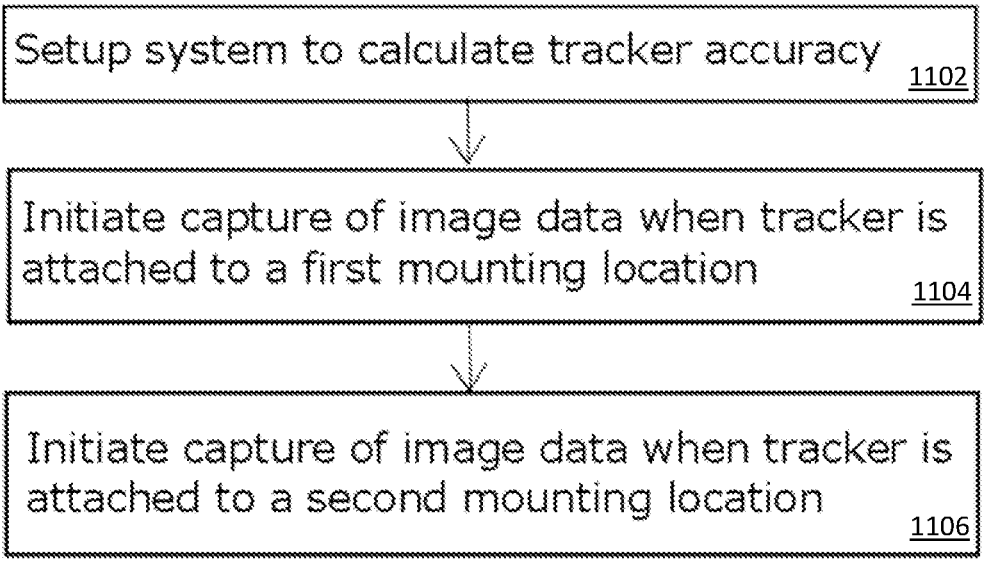
FIGS. 11A and 11B are flowcharts showing workflow and other computer operations to calculate a Tracker Assessment Parameter.
Figure 11B:
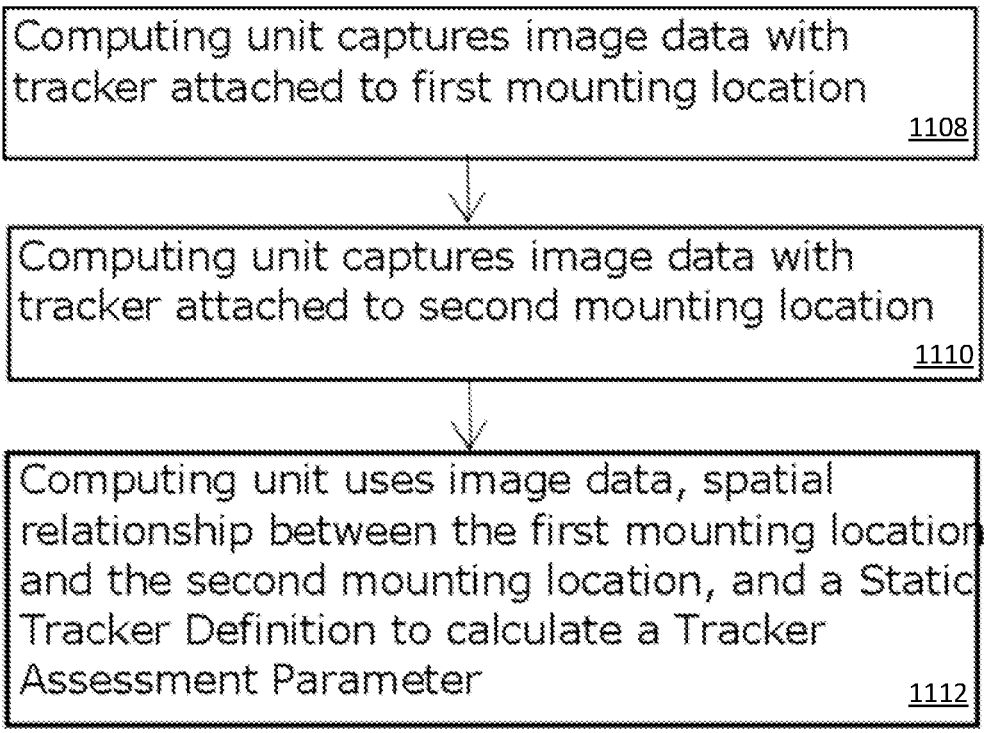

Reference is now made to flowcharts FIGS. 11A and 11B showing workflow 1100A and other computer operations 1100B to calculate a Tracker Assessment Parameter.

Figure 12:
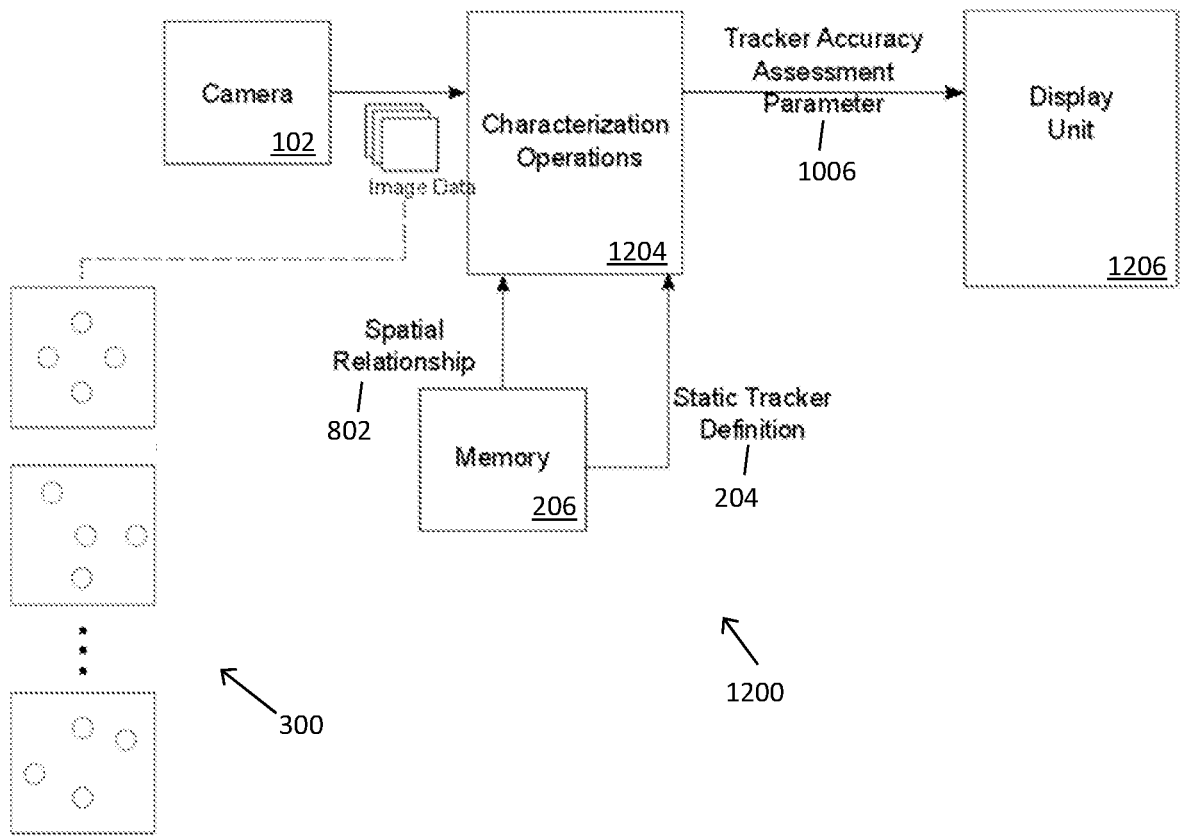
FIG. 12 shows a block diagram depicting a verification operation (part of characterization operations) that provides a Tracker Assessment Parameter to a display unit as an example for clarity.

At 1102, workflow 1100A, executing on a computing unit 104, provides user instructions to set up the system by attaching camera 102 to sensor mounting location. At 1104 and then 1106 the user is further instructed by the workflow 1100A to attach tracker 106 consecutively on a first mounting location 304 and a second mounting location 304 in order to capture image data 600 for verification. Corresponding computer-implemented method 1100B calculate the Tracker Assessment Parameter 1006 in operations 1108, 1110 and 1112. Computing unit 104 captures at 1108 and 1110 image data 600 of a tracker 106 attached to a first tracker mounting location 304 and a second tracker mounting location 304 on a characterization jig 300. Using image data 600, known Inter Tracker Mount Spatial Relationship 802 between the tracker mounting locations 304, and the Static Tracker Definition 204, the computing unit 104 calculates the Tracker Assessment Parameter 1006 at 1112. The Tracker Assessment Parameter 1006 may simply be presented to the user (e.g.: on a display unit 1206) to allow the user to make further decisions. FIG. 12 shows a block diagram depicting a verification operation 1200 (part of characterization operations) that provides a Tracker Assessment Parameter to a display unit. Computing unit 104 receives image data 600 from the optical sensor 102 of the tracker 106 attached to the characterization jig 600 and receives from memory 206 a known spatial relationship, such as the Inter Tracker Mount Spatial Relationship 802 and the Static Tracker Definition 204. The computing unit 104 performs characterization operations 1204 using the image data 600, the known spatial relationship 802, and the Static Tracker Definition 204 to calculate the Tracker Accuracy Assessment Parameter 1006. The computing unit 104 then displays the Tracker Accuracy Assessment Parameter on a display unit 1206.

Figure 13:
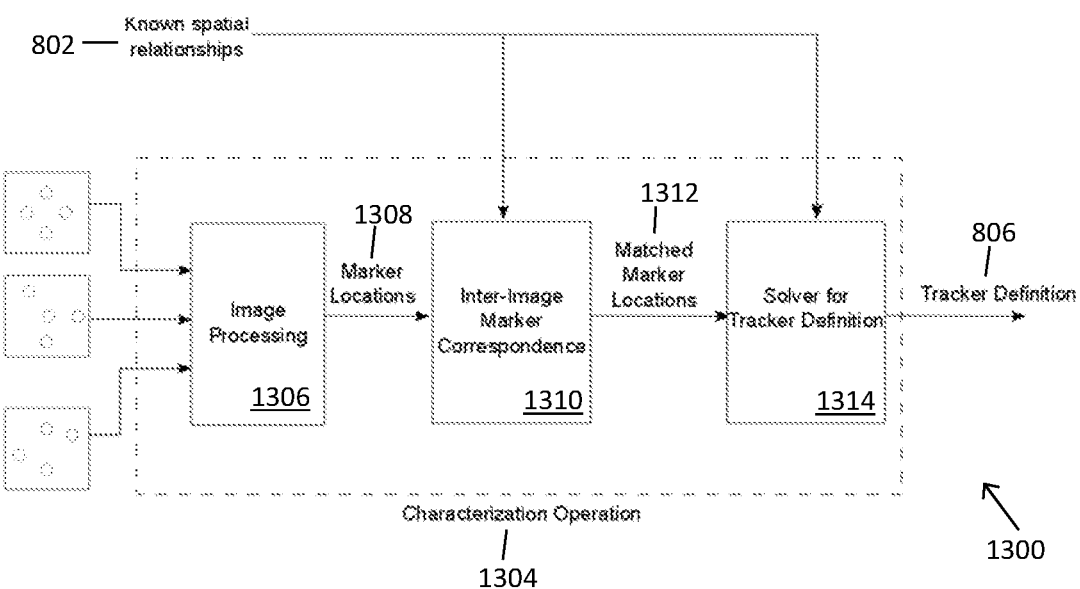
FIG. 13 depicts an exemplary characterization operation to show how inputs are processed in order to calculate a Tracker Definition.

FIG. 13 depicts an exemplary characterization operation 1300 in a block diagram to show how inputs are processed in order to calculate Tracker Definition 806. Characterization operation 1300 is shown in three stages 1304. First, image data 600 (comprising multiple 2D images) received from camera 102 is image processed 1306 to discern the optically detectable features 108 (e.g., markers) in each instance of image data 600. The locations of each optically detectable feature 1308, also called the marker locations, in an image are used in the next stage 1310 where the operations create a correspondence between an optically detectable feature of one image and the same feature in a second image, and so on. The resulting matched marker locations 1312 are optimized and presented to the third stage 1314 where operations solve for a value for Tracker Definition 806. Persons skilled in the art will understand that this is an exemplary operation, and that there may be a variety of operations that can be executed to perform such calculations.

Computing unit 104 may comprise multiple, distributed processing units (e.g. characterization may be carried out on one computing unit 104, whereas intra-operative localization may be carried out by another computing unit 104). It will be evident to those skilled in the art what data must be transferred between various computing units 104 to enable the functionality of the systems and methods described herein. Tracker characterization or verification may be performed on an ad-hoc basis as part of routine maintenance of trackers 106, or may be performed prior to each localization procedure that uses tracker 106. A person skilled in the art will appreciate that the level of accuracy of measurements will improve with an increase in the number of mounting locations for tracker 304, or camera 306 and the corresponding image data 600 captured by the camera 102.

Characterization jig 300 has a plurality of mounting locations that can receive a sensor 306 or a tracker 304. In the exemplary configuration of the characterization jig 300 described above, multiple tracker mounting locations 304 with a known Inter Tracker Mount Spatial Relationship 802 are described. In another configuration, multiple camera mounting locations 306 are provided and a known Inter Sensor Mount Spatial Relationship may be used. Tracker 106 may be attached to one tracker mounting location 304 while the multiple camera mounting locations 306 provide multiple vantage points of tracker 106. The instructions on computing unit 104 may be adapted accordingly. Each of the variations described above are applicable to a characterization jig 300 that comprises multiple mounting locations 306 for an optical sensor such as camera 102. An advantage of moving the camera 102 (instead of the tracker 106) to achieve the various vantage points is that the system can then characterize tracker 106 that does not have a repeatable mounting mechanism in its base. For example, the tracker 106 may be a fully integrated probe with a tip and no mounting mechanism; the optically detectable features 108 (e.g.: markers) may be attached to a surgical instrument directly instead of attaching tracker 106 to the instrument, etc.

It may be desirable to characterize multiple trackers 106 simultaneously. The characterization jig 300 may comprise at least two camera mounting locations 306 for use with one camera 102 and a known Inter Sensor Mount Spatial Relationship. The multiple trackers 106 are fixed relative to each other i.e. there is a fixed positional relationship amongst the trackers 106. For example, tracker 106 may be attached via its own mount to another instance of a tracker 106, and multiple trackers 106 may be attached to tracker mounting locations 304 on a characterization jig 300. In another example, multiple trackers 106 may be resting on a surface during characterization, etc. The multiple trackers 106 are within a field of view of the camera 102 when camera 102 is attached to each of the at least two camera mounting locations 306 on characterization jig 300. Image data 600 comprising at least two images of trackers 106 showing optically detectable features 108 of each tracker 106 are provided to computing unit 104. Computing unit 104 may have access to additional information to distinguish between or among multiple trackers 106 in the image data 600. For example, this information may be an approximate Tracker Definition (Rough Tracker Definition) for each tracker 106, shapes of the optically detectable features 108 etc. In another example, optically detectable features 108 of each tracker 106 may be of different colours, and this difference may be known. In another example, the system may be configured to have substantial spacing between or among trackers 106 during image capture such that the various trackers 106 can be distinguished within an image based on the spacing of optically detectable features 108 within image data 600. Computing unit 104 may calculate an instance of Tracker Definition 806 for each tracker using image data 600, the Inter Sensor Mount Spatial Relationship and the additional information to distinguish between or among multiple trackers 106.

Characterization jig 300 may be encoded with an optically readable barcode or other identifier that can be used to load specific information about the spatial relationships between the various mounting locations, comprising the tracker mounting locations 304 and the camera mounting locations 306. Each characterization jig 300 may have a different Inter Tracker Mount Spatial Relationship 802 or Inter Sensor Mount Spatial Relationship associated with it. At the beginning of the tracker verification or characterization process, camera 102 may read the identifier to allow computing unit 104 to access known pre-loaded information, such as the spatial relationships between the various mounting locations 802 for that characterization jig 300. It is understood that the information may be retrieved from a remote store (not shown) via a communication network (not shown). Similarly, tracker 106 itself may be encoded with an optically readable barcode or other identifier or any other method of encoding that can be used to load or distinguish its Static Tracker Definition 204 in computing unit 104. The accuracy of tracker 106 may then be verified with respect to its Static Tracker Definition 204.

Figure 14:
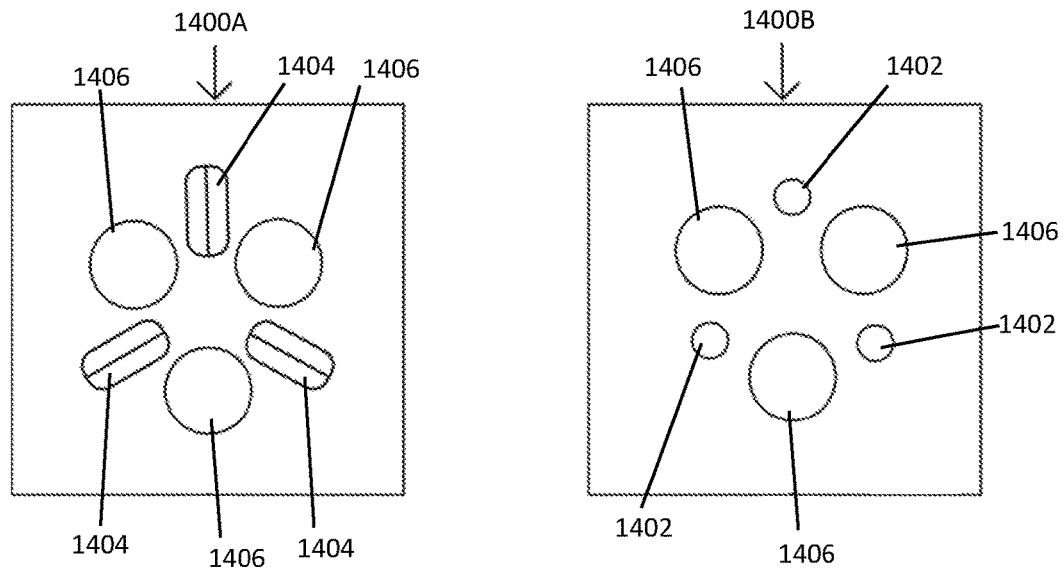
FIG. 14 depicts two sides/components of a kinematic mount that uses three pairs of attractive magnets and three pairs of pins and slots as an example for clarity.

A mounting location on characterization jig 300 can be any positionally repeatable mounting mechanism, preferably repeatable in six degrees of freedom. Depending on the application, it may be sufficient to use a mount that is repeatable in less than six degrees of freedom as long as the instructions executing on computing unit 104 take this factor into account. In this case, it may be necessary to obtain more than two images from the camera. Any mechanism achieving positional repeatability may form the repeatable mounting locations for tracker 106 and/or optical sensor 102 on characterization jig 300. For example, a magnetic kinematic mount may comprise two mating sides. Each side may have attractive pairs of magnets to hold the mechanism together, and precise slots/hemispherical pins that mate with each other when the mechanism is "connected", and provide a highly repeatable kinematic mount. A kinematic mount is a mechanical interface which is highly repeatable (i.e. between connect and disconnect cycles) in up to 6 degrees of freedom (3 degrees of freedom in orientation and 3 degrees of freedom in translation). Two views of an exemplary kinematic mount 1400 (1400A, 1400B) are illustrated in FIG. 14. Three pairs of hemispherical pins 1402 and corresponding slots 1404 or V-grooves mate using three pairs of attractive magnets 1406 to hold the first side of the kinematic mount 1400A together with the second side of the kinematic mount 1400 Band enforce a kinematic connection. It is important to note that there are several kinds of kinematic mounts, an example of which is provided in this specification. This kinematic mount is included as an example for clarity and is not meant to limit the scope of the specification. Any other repeatable mounting mechanism and/or feature may be used, e.g. dovetail connections, cam locks, v-grooves, rails, flat surfaces, ball detents, clamps, etc.

Figure 15:
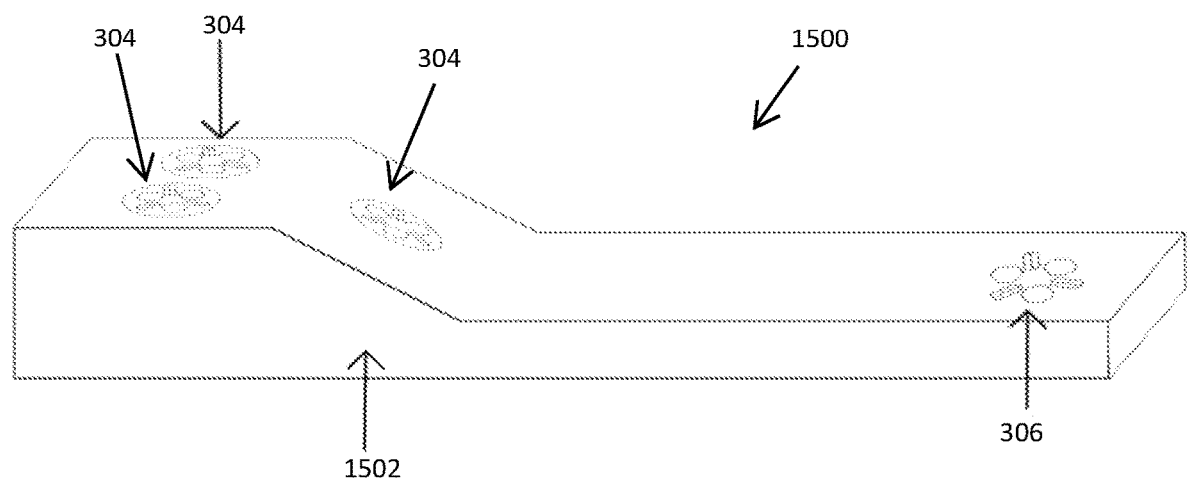
FIG. 15 shows another configuration of a characterization jig with one mounting location for a tracker in a different plane as an example for clarity.

A minimum of two repeatable mounting locations are required to enable Tracker Characterization and Verification as described above. Multiple repeatable mounting locations may increase the accuracy, performance or robustness of the characterization or verification process. Where more than two mounting locations are used, it may be desirable for at least one mounting location to be in a different plane than the first two mounting locations. In FIG. 15, a characterization jig 1500 comprises a rigid base 1502, a camera mounting location 306 and three tracker mounting locations 304. The first tracker mounting location 304 and second tracker mounting location 304 differ by one degree of freedom in the pose of the tracker 106 when attached to these tracker mounting locations 304, whereas a third tracker mounting location 304 further provides a difference in a second degree of freedom. In other words, the rotations between the three tracker mounting locations are about two different 3D vectors.

In an exemplary configuration of the characterization jig 1500, a single mounting location using a magnetic kinematic mount may provide multiple poses of the tracker 106 to the camera 102, such that the difference in rotation between each of the poses is known. The single mounting location may effectively act as two (or more) mounting locations. Additionally, for example, the kinematic mount of FIG. 14 may permit indexing functionality. In the absence of other constraints, the mount may be mated in a total of three orientations, each spaced at 120 degrees. In this case, in at least one of three mounting configurations, the tracker 106 is likely facing away from the camera 102, and may not generate a valid image for pose calculation due to optical occlusion. However, the remaining two mounting configurations may yield a vantage point from which a valid pose of the tracker 106 may be captured. The difference in rotation in these two mounting configurations is 120 degrees. In the example depicted in FIG. 14, the number of slots 1404 (or pins 1402) could be increased to provide finer indexing capability (e.g. doubling the number of equally spaced slots 1404 would provide rotational indexing at 60 degree increments). Various types of indexing mounts are contemplated, including the use of indexing adaptors. The advantage of indexing mounts is that a single mount may effectively serve as multiple mounts, without the cost/complexity/size/footprint associated with multiple mounts.

It may be advantageous to obtain information about the geometry of the optically detectable features of the tracker with respect to the base of the tracker. This information, also known as the Tracker Base Geometry, may be added to the Tracker Definition and be used to allow a localization system to determine the location of the object to which the tracker is attached. The steps to obtain Tracker Base Geometry are described below. In order to obtain this information, the spatial relationship between the camera and each tracker mounting location (referred to in this specification as Sensor Tracker Mount Spatial Relationship) is required. The base of the tracker may comprise a repeatable mounting mechanism. The camera mounting location and tracker mounting locations may optionally be on the same characterization jig.

Figure 16A:
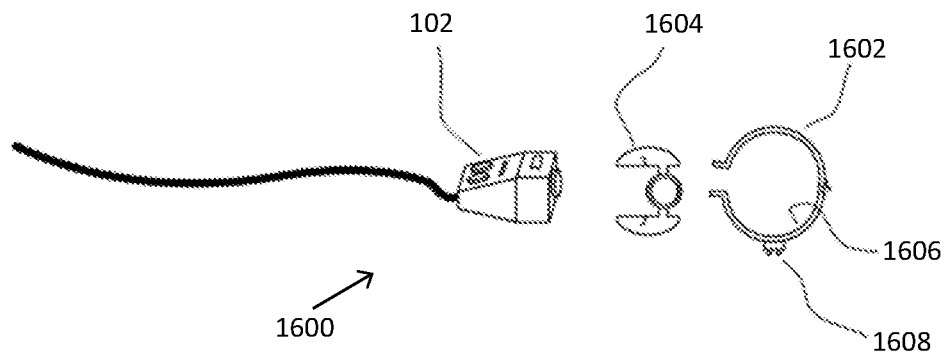
FIGS. 16A and 16B shows the components of a camera with a shroud and a clamp and the assembled shroud, camera and clamp assembly.
Figure 16B:
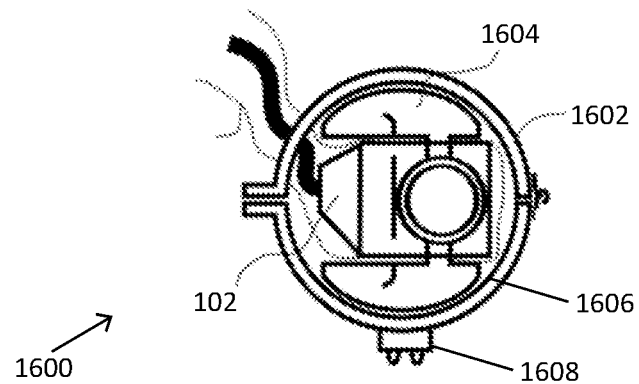

The camera may attach directly and repeatably to the characterization jig or be attached with the use of a clamp or other means. Reference is now made to FIG. 16A. A clamp assembly 1600 consists of an optical sensor 102 and a clamp 1602, and optionally a shroud 1604. The shroud 1604 fixes the optical sensor 102, and is placed within the clamp 1602. The shroud 1604 (shown in a simplified manner) has an outer surface which matches a mating surface 1606 on the inside of the clamp 1604. Each of the mating surfaces may define portions of a sphere, such that the clamp 1602/shroud 1604 interface provides an alignment mechanism that is functionally a lockable ball joint. The clamp 1602 has a mechanism (e.g. a screw/hinge combination) which applies a force on the shroud 1604 (and, in turn, the optical sensor 102), and clamps it rigidly and releasably in place. The shroud 1604 and the clamp 1602 have respective mating surfaces which, when the optical sensor 102 is in the shroud 1604 and the clamp 1602 is in a partially closed position, enable relative movement of the shroud 1604 and clamp 1602 to adjust the orientation of the optical sensor 102. The clamp 1602 has a base 1608 which may be a kinematic mount. FIG. 16B shows a camera 102 assembled with a shroud 1604 and clamp 1602. Since the sensor 102, when fixed within the clamp assembly 1600 and attached to the sensor mounting location 306 on the characterization jig, is not in a known spatial relationship with respect to the characterization jig, the characterization jig must be registered to the optical sensor 102 i.e. the optical sensor 102 must localize the characterization jig in space, as described further below.

Figure 17:
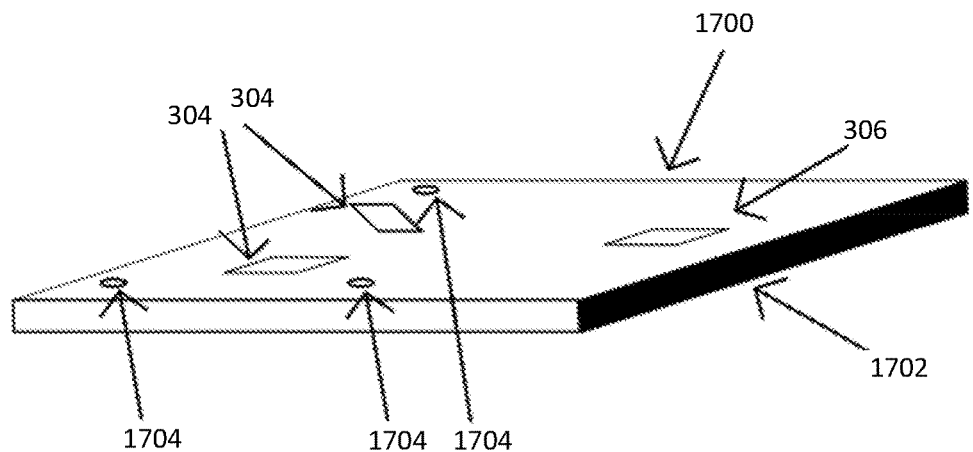
FIG. 17 shows calibration divots on another exemplary configuration of a characterization jig.

Reference is now made to FIG. 17 showing an exemplary configuration of a characterization jig 1700 comprising a rigid base 302, tracker mounting locations 304, a camera mounting location 206, and additional features such as calibration divots 1704. Once the optical sensor 102 is attached to its mounting location 306 on the characterization jig 1700, the three calibration divots 1702 are used to register the characterization jig 1700 to the optical sensor 102. The three calibration divots 1702 are not collinear since collinear divots would not yield enough information to perform registration.

Figure 18:
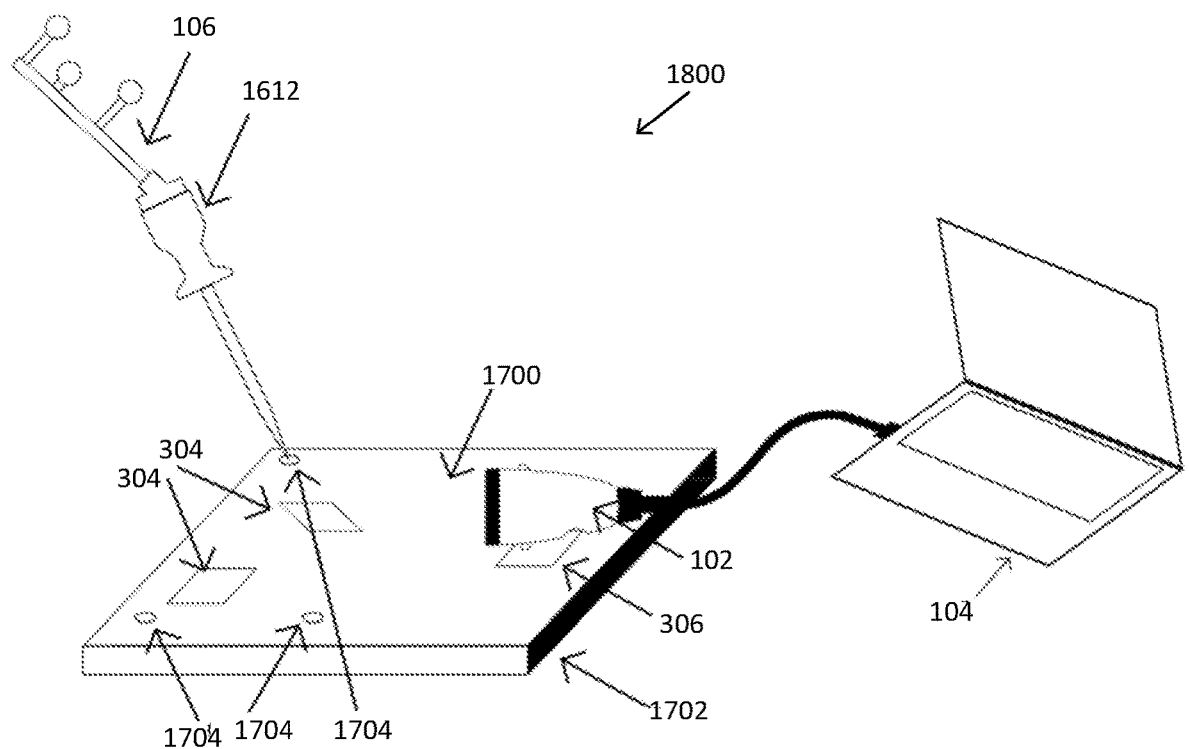
FIG. 18 shows a probe with a tracker attached to it probing divots on a characterization jig.

If a probe 1612 is used to localize calibration divots 1702 with respect to the camera 102, then the probe 1612 itself must be calibrated (i.e. the position of the tip of the probe with respect to the markers 108 on the tracker 106 must be known). A different tracker 106 may be used for this purpose. The probe 1612 and tracker 106 may be precalibrated i.e. the position of the tip may be known via the manufacturing and/or inspection process or determined via a calibration procedure. FIG. 18 illustrates a characterization system 1800, a probe 1612 with a tracker 106 attached to it is placed in one of the calibration divots 1702 on the characterization jig 1700. An exemplary probe calibration process involves the following steps: the tracker 106 is attached to the probe 1612 and is pivoted about a fixed point (e.g.: one of the calibration divots 1702 on the characterization jig 1700) while being tracked by the camera 102. Using images of the tracker 106 generated during pivoting, a computing unit 104 executes a "center of rotation" operation to determine the location of the tip of the probe.

Figure 19A:
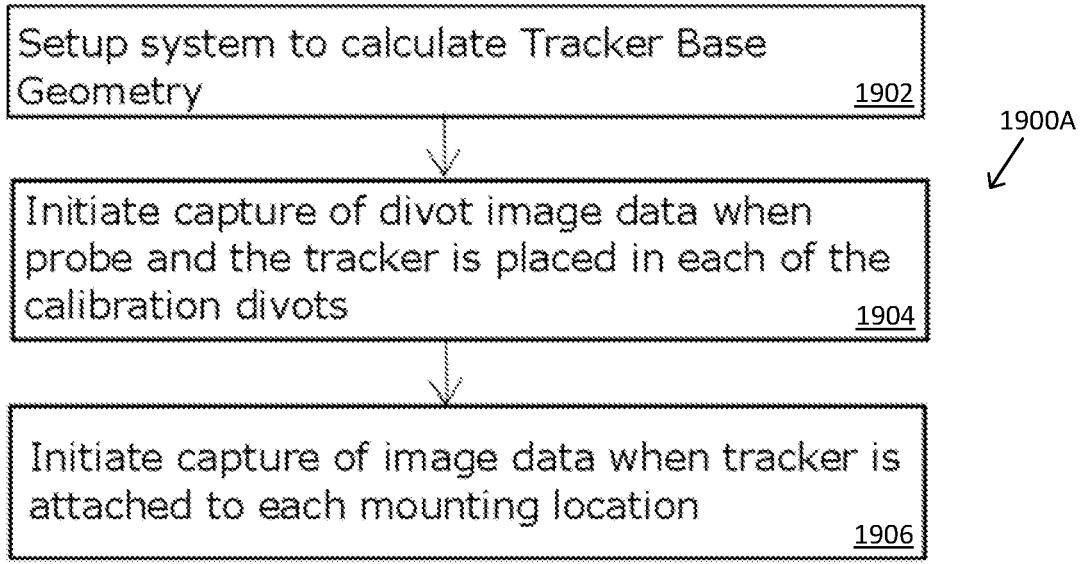
FIGS. 19A and 19B are flowcharts showing workflow and other computer operations to calculate a Tracker Base Geometry.
Figure 19B:
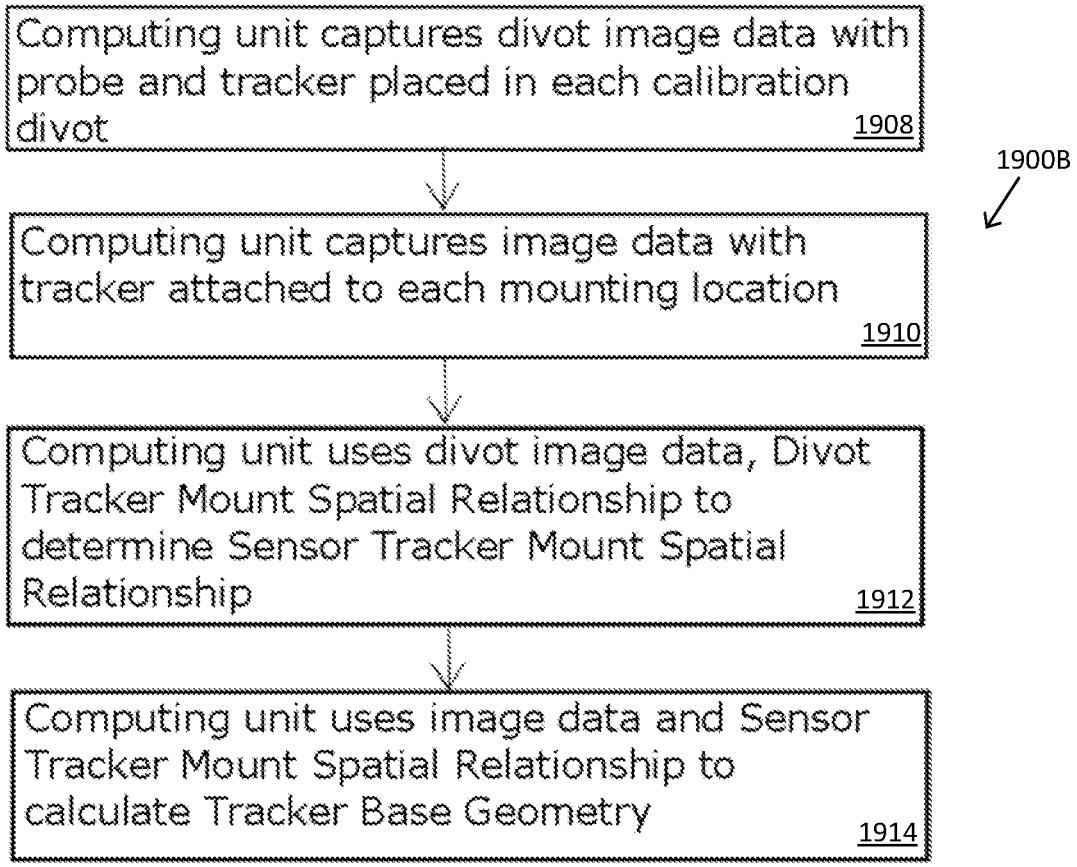

As described previously, the geometrical spatial relationships 802 between the various features of the characterization jig 1700, its 3D shape, etc. are known. For calculation of a Tracker Definition 806, instructions executing on the computing unit 104 utilize the known spatial relationships between a first mounting location and a second mounting location 802. In the examples above, the use of the Inter Tracker Mount Spatial Relationship 802 or the Inter Sensor Mount Spatial Relationship has been described. Similarly, the spatial locations of each of the three calibration divots with respect to the tracker mounting locations (Divot Tracker Mount Spatial Relationship) is known to the computing unit 104 and are used in the calculation of Tracker Base Geometry. FIGS. 19A and 19B are flowcharts showing workflow 1900A and other computer operations 1900B to calculate a Tracker Base Geometry. At 1902, a computing unit instructs a user to set up the system to calculate Tracker Base Geometry. The user is instructed, by a workflow executing on the computing unit 104, to place the probe 1612 (with the tracker 106 attached to it) in each of the three (or more) calibration features and initiate capture of divot image data 600 that comprises at least three images of the tracker (at 1904 and 1906). A corresponding computer-implemented method is illustrated where a computing unit 104 captures divot image data from a camera 102 with the probe 1612 (with the tracker 106 attached to it) placed in each calibration divot 1702, 1908. The computing unit 104 then captures image data 600 from a camera 102 with the tracker 106 attached to each tracker mounting location 304, 1910. The computing unit 104 utilizes the divot image data, as well as the known Divot Tracker Mount Spatial Relationship to determine the Sensor Tracker Mount Spatial Relationship 1912. The computing unit 104 further utilizes the Sensor Tracker Mount Spatial Relationship, as well as image data 600 of a tracker 106 attached to a particular tracker mounting location 304, to calculate the Tracker Base Geometry 1914. The Tracker Base Geometry may be added to the Tracker Definition 806. The Sensor Tracker Mount Spatial Relationship is required for determining the Tracker Base Geometry. The Sensor Tracker Mount Spatial Relationship may be determined using a known spatial relationship between the optical sensor and the sensor mounting location, and the Sensor Mount Tracker Mount Spatial Relationship. The computing unit 104 uses both known spatial relationships to determine the Sensor Tracker Mount Spatial Relationship. To compute the Tracker Base Geometry, the computing unit 104 further utilizes the Sensor Tracker Mount Spatial Relationship, as well as image data 600 of a tracker 106 when attached to tracker mounting locations 304.

If the positions of the optical sensor 102 and tracker 106 on the characterization jig 1700 are reversed, the resulting calculation is that of a Sensor Sensor Mount Spatial Relationship, instead of a Tracker Base Geometry for the tracker.

In addition to using the calibration divots 1702 for determining geometry of the markers 108 to the base of the tracker, the calibration divots 1702 may also be used to verify the accuracy of the measurements provided by the localization system. The computing unit 104 may be adapted to execute instructions such that a user can check if a physical location of the tip of the probe 1612 on a known geometrical model of a characterization jig 1700 corresponds to the location obtained through localization.

Figure 20:
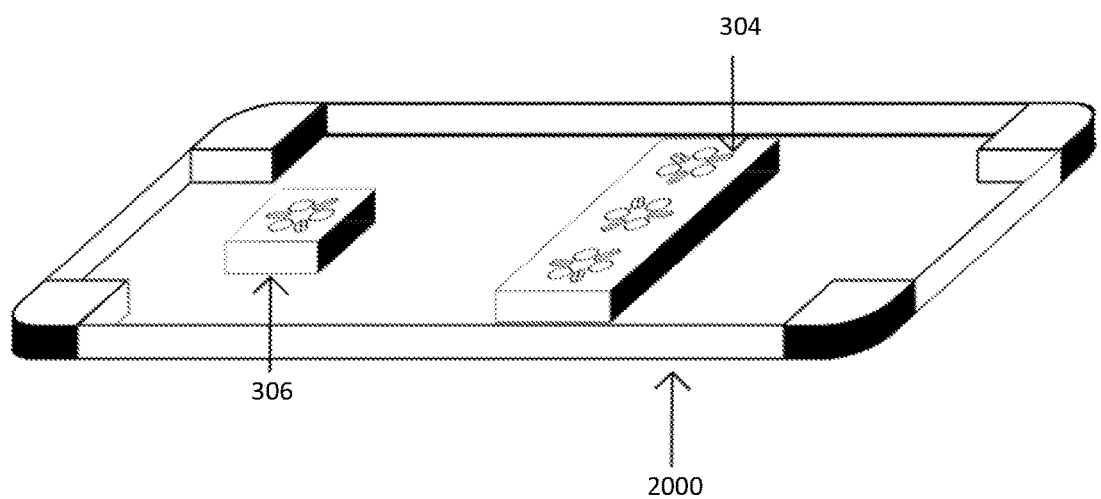
FIG. 20 shows a characterization jig on a lid of a sterilization tray.

For use in surgical applications, the characterization jigs described above may be made entirely of sterilisable materials. The characterization jigs may also be configured to fit within a sterilization tray. It may be integrated into a lid of the sterilization tray or be a separate component. FIG. 20 illustrates a lid of a sterilization tray 2000 (typically used in surgical settings) configured to be a characterization jig with a camera mounting location 306 and tracker mounting locations 304.

Tracker Characterization and Verification with Golden Tracker

Systems, methods and components for tracker characterization and verification using a Golden Tracker are predominantly described with reference to FIGS. 1-2, 6, and 20-30 though it will be understood that there is some overlap with concepts etc. to earlier or later described embodiments herein. There is described and shown a computer-implemented method comprising the steps of: receiving, by a computing unit, a first image of a tracker and a Golden Tracker, separated by a fixed spatial relationship, the first image captured by an optical sensor from a first vantage point when both trackers appear in a field of view of the optical sensor; receiving, by the computing unit, a second image of a tracker and a Golden Tracker, separated by the fixed spatial relationship, the second image captured by the optical sensor from a second vantage point when both trackers appear in the field of view of the optical sensor; and calculating, by the computing unit, at least one of: a Tracker Definition using the first image, the second image, an image difference, and the Golden Tracker Definition; and a Tracker Assessment Parameter using the first image, the second image, the Golden Tracker Definition and a Static Tracker Definition.

The method may further comprise calculating, by the computing unit, the image difference by calculating a difference in pose of the Golden Tracker between the first image and the second image using the first image, the second image and the Golden Tracker Definition.

The fixed spatial relationship may be an Inter Tracker Mount Spatial Relationship of a characterization jig comprising mounting locations for the tracker and Golden Tracker and when the method calculates the Tracker Definition, the method may further comprise calculating, by the computing unit, a Tracker Base Geometry using the first image, the second image, the image difference, the Inter Tracker Mount Spatial Relationship, the Golden Tracker Definition and a Golden Tracker Base Geometry.

The optical sensor may be attached to a platform and the tracker and the Golden Tracker are attached to each other.

When the method calculates the Tracker Definition, the method may further comprise calculating, by the computing unit, a Tracker Base Geometry using the first image, the second image, the image difference, the fixed spatial relationship, the Golden Tracker Definition and a Golden Tracker Base Geometry. The tracker and the Golden Tracker may be attached to each other.

The method may further comprise providing, by the computing unit, at least one of the Tracker Definition or the Tracker Assessment Parameter as calculated for use in a localization procedure.

The method may further comprise providing, by the computing unit, user instructions for display by a display unit.

When the method calculates the Tracker Assessment Parameter, the method may further comprise providing, by the computing unit, the Tracker Assessment Parameter for display by a display unit.

The tracker and the Golden Tracker may be attached to a respective mounting location on a characterization jig.

There is shown and described a computer-implemented method comprising the steps of: receiving, by a computing unit, an image of a tracker and a Golden Tracker attached to each other from one vantage point when both trackers appear in a field of view of an optical sensor; calculating, by the computing unit, a Tracker Assessment Parameter using the image, a Golden Tracker Definition, a Golden Tracker Base Geometry, a Static Tracker Definition and a Static Tracker Base Geometry.

There is shown and described a system comprising: a Golden Tracker; and a computer-readable storage device storing instructions and data, including a Golden Tracker Definition for the Golden Tracker, which, when executed on a computing unit, configure the computing unit to: receive a first image of a tracker and the Golden Tracker, separated by a fixed spatial relationship, the first image captured by an optical sensor from a first vantage point when both trackers appear in a field of view of the optical sensor; receive a second image of the tracker and the Golden Tracker, separated by the fixed spatial relationship, the second image captured by the optical sensor from a second vantage point when both trackers appear in the field of view of the optical sensor; and calculate at least one of a Tracker Definition for the tracker using the first image, the second image, an image difference, and the Golden Tracker Definition; and a Tracker Assessment Parameter for the tracker using the first image, the second image, the image difference, and a Static Tracker Definition.

The computing unit may be further configured to calculate the image difference by calculating a difference in pose of the Golden Tracker between the first image and the second image using the first image, the second image and the Golden Tracker Definition.

The computing unit may be further configured to provide at least one of the Tracker Definition or the Tracker Assessment Parameter for use in a localization procedure.

The computing unit may be further configured to provide user instructions for display on a display unit.

The computing unit may be further configured to provide the Tracker Assessment Parameter when calculated for display on a display unit.

The system may further comprise a display unit to display the Tracker Assessment Parameter.

The tracker and the Golden Tracker may be attached to a respective mounting location on a characterization jig.

The characterization jig may be made entirely of sterilisable material or made entirely of non-sterilisable material.

The system may further comprise the characterization jig.

The system may further comprise the optical sensor.

The fixed spatial relationship may be an Inter Tracker Mount Spatial Relationship of a characterization jig comprising mounting locations for the tracker and Golden Tracker and when the computing unit is configured to calculate the Tracker Definition, the computing unit may be further configured to calculate a Tracker Base Geometry using the first image, the second image, the image difference, the Inter Tracker Mount Spatial Relationship, the Golden Tracker Definition and a Golden Tracker Base Geometry.

The optical sensor may be attached to a platform and the tracker and the Golden Tracker are attached to each other.

When the computing unit is configured to calculate the Tracker Definition, the computing unit may be further configured to calculate a Tracker Base Geometry using the first image, the second image, the image difference, the fixed spatial relationship, the Golden Tracker Definition and a Golden Tracker Base Geometry. The tracker and the Golden Tracker may be attached to each other.

There is shown and described a system for characterizing a tracker for localization in a surgical procedure, the system comprising: a non-sterile Golden Tracker; a sterile characterization jig comprising at least two mounting locations and further configured to simultaneously attach the Golden Tracker and a sterile tracker on each mounting location respectively without compromising the sterility of the tracker; a computer-readable storage device storing instructions and data, including a Golden Tracker Definition for the Golden Tracker, which, when executed on a computing unit, configure the computing unit to: receive a first image of the tracker and the Golden Tracker captured by an optical sensor from a first vantage point when both trackers appear in a field of view of the optical sensor; receive a second image of the tracker and the Golden Tracker captured by the optical sensor from a second vantage point when both trackers appear in the field of view of the optical sensor; and calculate at least one of: a Tracker Definition for the tracker using the first image, the second image, an image difference, and the Golden Tracker Definition; and a Tracker Assessment Parameter for the tracker using the first image, the second image, the image difference, the Golden Tracker Definition and a Static Tracker Definition.

This document describes two systems—one for localization and the other for characterization. It is to be understood that these may be distinct systems that utilise the same hardware such as the camera to capture images and the computing unit to execute instructions. These systems may also be distinct units that use different hardware. It is also possible that these distinct systems communicate with each other to present a seamless user experience but optionally utilise the same hardware. Alternatively, the characterization system may be used separately from the localization system. For example, the characterization system may be used as part of quality control at a manufacturing site while manufacturing a localization system for use in a surgical setting. The hardware and software used to characterize the tracker may be completely distinct.

In an embodiment, a tracker may be characterized i.e. its Tracker Definition calculated by using a characterization system comprising a "Golden Tracker", with a known Golden Tracker Definition, and instructions executing on the computing unit. The "Golden Tracker" refers to a tracker whose optically detectable features have a spatial relationship that precisely match its Golden Tracker Definition. The degree of precision may be dependent on the desired accuracy for localization measurements using the characterized tracker. In this embodiment, the tracker and the Golden Tracker are separated by a fixed positional relationship i.e. the relationship must not vary during the execution of characterization and/or verification operations. An optical sensor, in communication with a computing unit, is not required to be attached to a sensor mounting location and can be handheld to capture at least one image each from multiple vantage points around the trackers such that the view of the trackers is substantially different from each vantage point. Alternatively, the optical sensor may be attached to multiple mounting locations on a characterization jig or to platforms configured to receive optical sensors; the mounting locations or platforms thus providing the multiple vantage points. Or, the optical sensor may be attached to a platform while the tracker and Golden Tracker are attached to each other and images are captured as both trackers are moved around together. Both trackers should appear in a field of view of the optical sensor from each vantage point. The image data comprising images of the tracker and Golden Tracker are provided by the optical sensor as an input to characterization and/or verification operations executing on the computing unit. By identifying and classifying the optically detectable features of the tracker and the Golden Tracker in the image data captured from various vantage points and the Golden Tracker Definition, instructions executing on the computing unit may calculate a Tracker Definition for the tracker (e.g. by performing an optimization routine). The accuracy of a tracker can also be verified with respect to a previously defined Tracker Definition. The verification process may further generate a Tracker Assessment Parameter. Exemplary operations are described further in this document.

Figure 21:
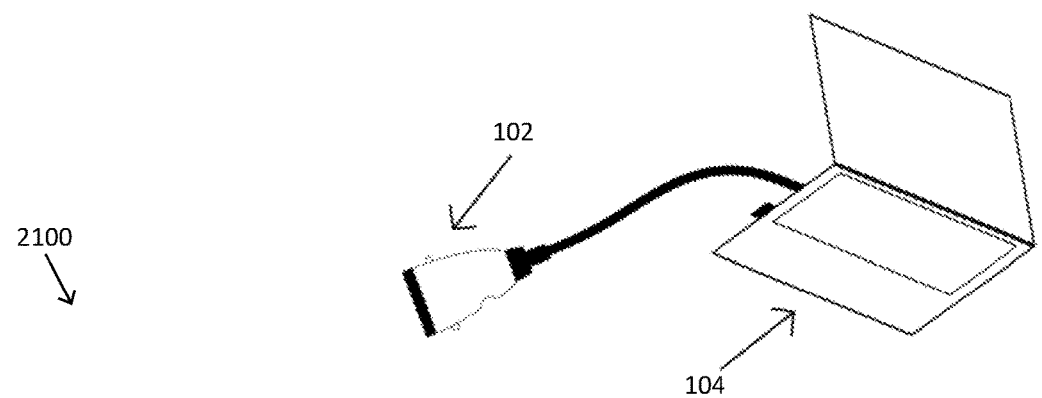
FIG. 21 illustrates a characterization system using a handheld camera connected to a computing unit to capture image data showing both a tracker and a Golden Tracker separated by a fixed positional relationship.
Figure 21:
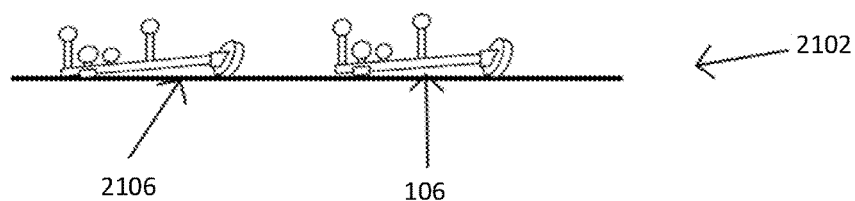

FIG. 21 illustrates a system 2100 of characterizing and/or verifying tracker accuracy where the tracker 106 and Golden Tracker 2106 are separated by a fixed relationship with respect to each other while placed on a flat surface 2102 e.g., a table. The optical sensor 102 is not attached to a sensor mounting location 306 or a platform 2306 and can be moved around to capture image data 2506 comprising at least two images of both trackers from two vantage points respectively. The optical sensor 102 is connected to a computing unit 104 that is executing instructions comprising characterization operations to characterize the tracker 106 and determine a Tracker Definition 806 or instructions comprising verification operations 2702 to verify the accuracy of the tracker 106 with respect to a known Static Tracker Definition 204. The outputs of the characterization and/or verification operations may be fed into a localization system or displayed on a display unit 1206. In the exemplary figures of this document, both trackers appear to be of a similar geometrical shape and dimensions. This document also contemplates the use of a tracker 106 and Golden Tracker 2106 with different geometrical features. For example, the trackers may have a different number of optically detectable features 108, the spatial arrangement of the features may be different, geometrical characteristics of the optically detectable features may vary, etc. These known differences can further be used, in addition to the Golden Tracker Definition 2502, in the characterization and/or verification operations executing on the computing unit 104, for example, to improve efficiency, speed or robustness of the operations.

A practical example of how a Golden Tracker 2106 may be used in a sterile environment (such as an operating room) involves two nurses, one of whom is a sterile nurse assisting the surgeon during a surgical procedure and can handle the sterile tracker 106 (that is part of a localization system being used in the same operating room). The second nurse, a non-sterile nurse, can handle the non-sterile Golden Tracker 2106. Each nurse may respectively place the tracker 106 and Golden Tracker 2106 on a surface. The optical sensor 102 (that is optionally a part of the localization system) may be sterile or non-sterile; the respective nurse may move the optical sensor 102 such that it is aimed at both trackers, and capture image data. Since the spatial relationship between the trackers is fixed (i.e. the trackers are not moved during characterization or verification), operations executing on a computing unit 104 can determine a Tracker Definition 806 for the tracker 106 or verify its accuracy against a known Static Tracker Definition 204 using the difference in pose of the Golden Tracker 2106 from one vantage point of the optical sensor 102 to another. An exemplary operation is described in the paragraphs below.

The characterization system described in the example above may optionally comprise a characterization jig with at least two tracker mounting locations to attach the tracker and Golden Tracker respectively. Two objects are "attached" when both are in contact with each other to form a connection and there is a holding mechanism to enforce the connection. The attachment may be rigid and removable, for example, selectively removable. It may also be repeatable by virtue of the type of mechanism used for attachment, for example, a kinematic mount. The jig may be made entirely of sterilisable materials to allow use in sterile environments. The optical sensor may be handheld or attached to additional sensor mounting locations on the jig or attached to separate platforms to capture image data of the trackers while each tracker is attached to a respective tracker mounting location. The optical sensor may capture at least one image from each vantage point to provide input for the characterization operations. At least two vantage points must be used to capture the image data. With the trackers being separated by a fixed spatial relationship by virtue of the fixed tracker mounting locations, the computing unit executes instructions to optimize values for the Tracker Definition using the Golden Tracker Definition and image data.

Figure 22A:
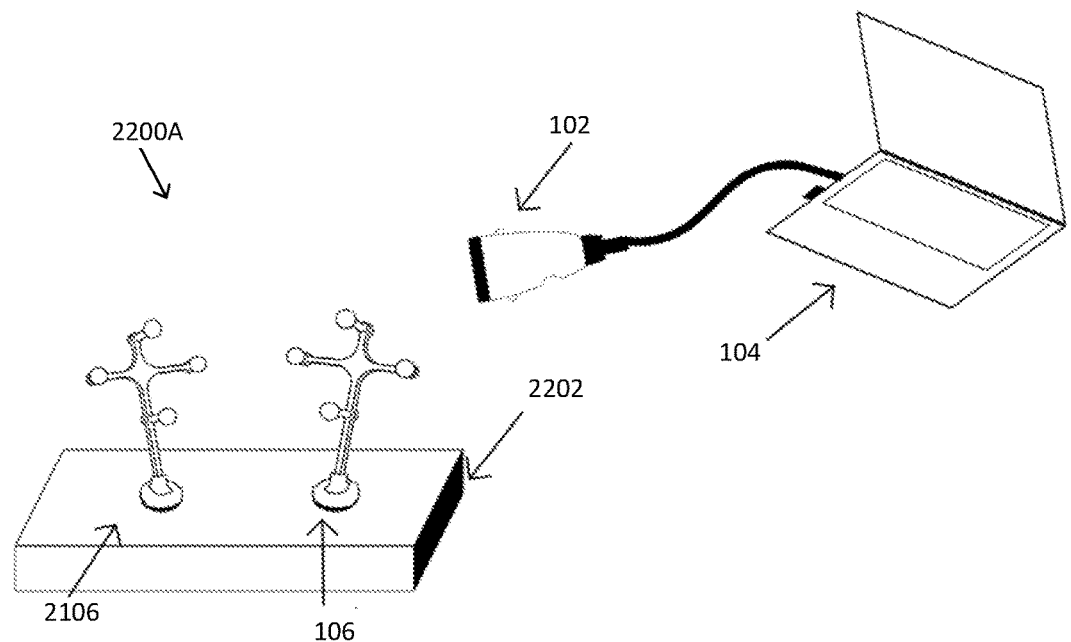
FIG. 22A illustrates a configuration of the characterization system in which the tracker and the Golden Tracker are attached to a characterization jig.
Figure 22B:
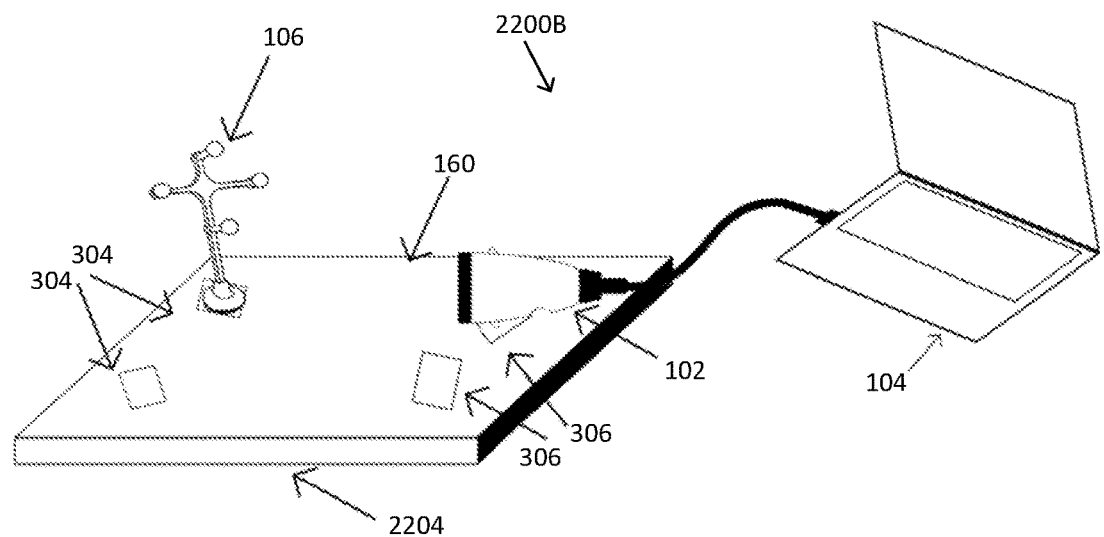
FIG. 22B illustrates a configuration of the characterization system in which the tracker, Golden Tracker and the camera are attached to the characterization jig.

Reference is now made to FIG. 22A of a system 2200A comprising a characterization jig 2202 with at least two tracker mounting locations 304 and a fixed spatial relationship between the tracker mounting locations while the optical sensor 102 is handheld. One of the two trackers is the Golden Tracker 2106 with a known Golden Tracker Definition and the other is the tracker 106 with an unknown Tracker Definition 806. The optical sensor 102 is in communication with a computing unit 104 and is used to capture a plurality of images of the trackers from a variety of vantage points or multiple viewing angles. A person skilled in the art will appreciate that for greater accuracy, a larger number of images may be captured during optimization. FIG. 22B illustrates a system 2200B comprising a characterization jig 2204 with multiple tracker mounting locations 304 and sensor mounting locations 306. The optical sensor 102 is moved from one sensor mounting location 306 to another to capture image data 2506 for characterization or verification.

Figure 23:
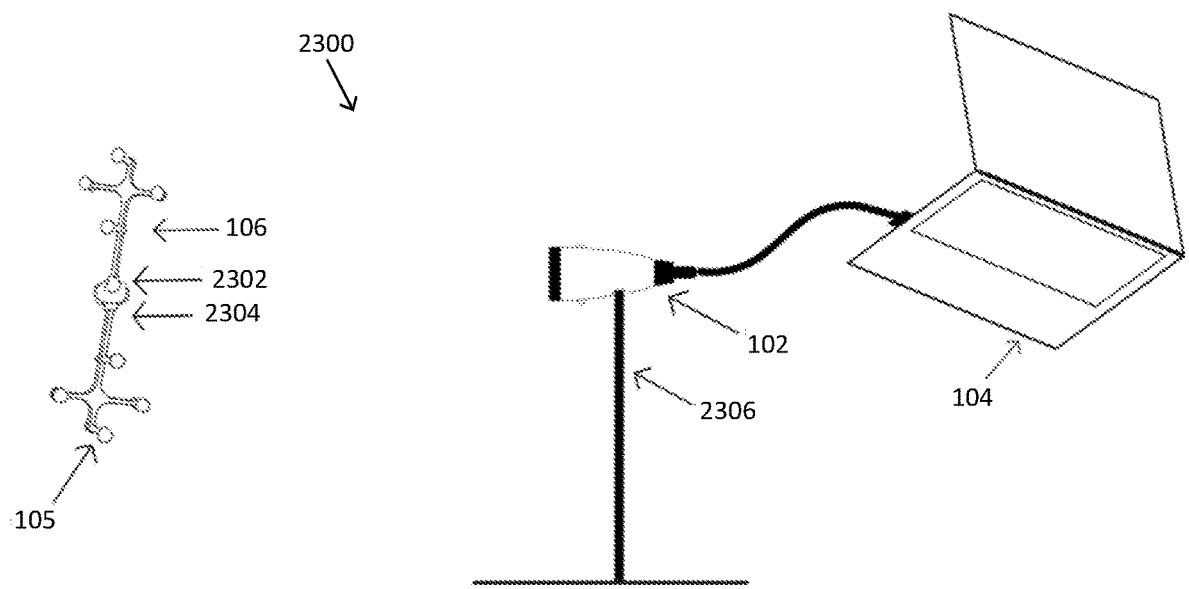
FIG. 23 illustrates a configuration of the characterization system in which the tracker and the Golden Tracker are attached to each other.

Reference is now made to FIG. 23 which illustrates a characterization system 2300. System 2300 comprises Golden Tracker 2106, tracker 106, optical sensor 102, computing unit 104, and a platform 2306. Golden Tracker 2106 and tracker 106 are attached to one another. Optical sensor 102 is coupled for communication with computing unit 104 and optical sensor 102 is mounted (attached) to platform 2306. The tracker 106 comprises a base 2302 and the Golden Tracker 2106 comprises a base 2304 that allow it to be attached to another mount. Such attachment means include magnets, springs, mating threads, cam-locks, etc. The attachment must be rigid. When using magnets as the attachment means, the magnets of the tracker 106 may be complementary to allow a direct attachment to the Golden Tracker 2106. Alternatively, an adapter may be used to allow an indirect attachment between the trackers. The adapter, with known geometrical dimensions, may have a first side comprising complementary magnets to attach the tracker 106, and a second side comprising complementary magnets to attach the Golden Tracker 2106. The use of the adapter may require the operations executing on the computing unit 104 to be modified accordingly.

In the example of FIG. 23, the Golden Tracker Definition 2502 (see too FIG. 25) includes the spatial relationship between the optically detectable features 108 and the base 2304 of the Golden Tracker. This is referred to as the Golden Tracker Base Geometry 2920 (see too FIG. 29) in this document. When the tracker 106 and Golden Tracker 2106 are attached to each other, the optical sensor 102 may be attached to a sensor mounting location 306 on a characterization jig or on a platform 2306 and image data from multiple vantage points may be captured by moving the tracker 106 and Golden Tracker 2106 instead of moving the optical sensor 102. Using image data and the Golden Tracker Definition including the Golden Tracker Base Geometry, the unknown Tracker Definition 806 may be calculated. In this configuration, the resulting Tracker Definition 806 also includes a Tracker Base Geometry for the tracker 106 i.e. the spatial relationship of the optically detectable features of the tracker 108 to the base of the tracker 2302.

Calculating a Tracker Base Geometry of the tracker 106 may also be done by attaching each of the tracker 106 and Golden Tracker 2106 to a tracker mounting location 304 respectively on a characterization jig 2202, 2204. The spatial relationship between the two tracker mounting locations 304 (also referred to as the Inter Tracker Mount Spatial Relationship) must be known for this variation of the embodiment. Using image data of both the tracker 106 and the Golden Tracker 2106, the Golden Tracker Definition that further comprises a Golden Tracker Base Geometry, and the Inter Tracker Mount Spatial Relationship 802, characterization operations can calculate the Tracker Definition 806 and the Tracker Base Geometry for the tracker (e.g. by performing optimization operations).

The Inter Tracker Mount Spatial Relationship 802 may be stored in memory 206 as a numerical representation of the relative poses between the mounting locations represented as rotation matrices, quaternions, Euler angles, translational vectors, Cartesian distances etc. The characterization jig may be manufactured to meet a specific Inter Tracker Mount Spatial Relationship 802, and the same spatial relationship may be accessible to the computing unit 104. For example, the numerical representation of this spatial relationship may be data stored in memory 206, preferably in a manner that prevents or reduces the possibility of deletion. There may be an identifier such as a barcode, QR-code, URL, etc. on the characterization jig itself that identifies the Inter Tracker Mount Spatial Relationship 802. The identifier may be read using the optical camera 102 and used to look up the Inter Tracker Mount Spatial Relationship 802 that is stored in memory 206 or remotely on a network.

Figure 24A:
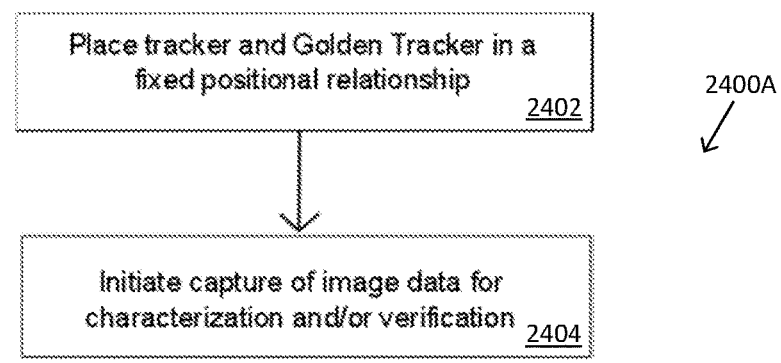
FIGS. 24A and 24B depict a user method and a computer-implemented method respectively to calculate tracker definition using the Golden Tracker.
Figure 24B:
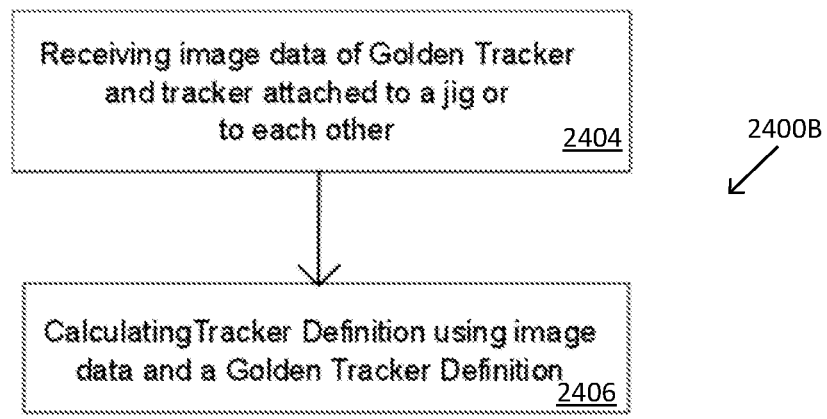

Reference is now made to FIGS. 24A and 24B that depict a user method 2400A and a corresponding computer-implemented method 2400B to calculate a Tracker Definition 806 using the systems described above. A workflow executing on the computing unit 104 instructs the user to place the tracker 106 and Golden Tracker 2106 in a fixed positional relationship 2402 to each other by attaching to each other, placing on flat surface 2102 or attaching to a characterization jig. The user may then initiate capture of image data by the optical sensor 102 from multiple vantage points 2404. The computing unit 104 receives image data of the tracker 106 and the Golden Tracker 2106 from the optical sensor 102, 2404. The computing unit 104 executes instructions to optimize and calculate the Tracker Definition 806 for the tracker using the Golden Tracker Definition.

Figure 25A:
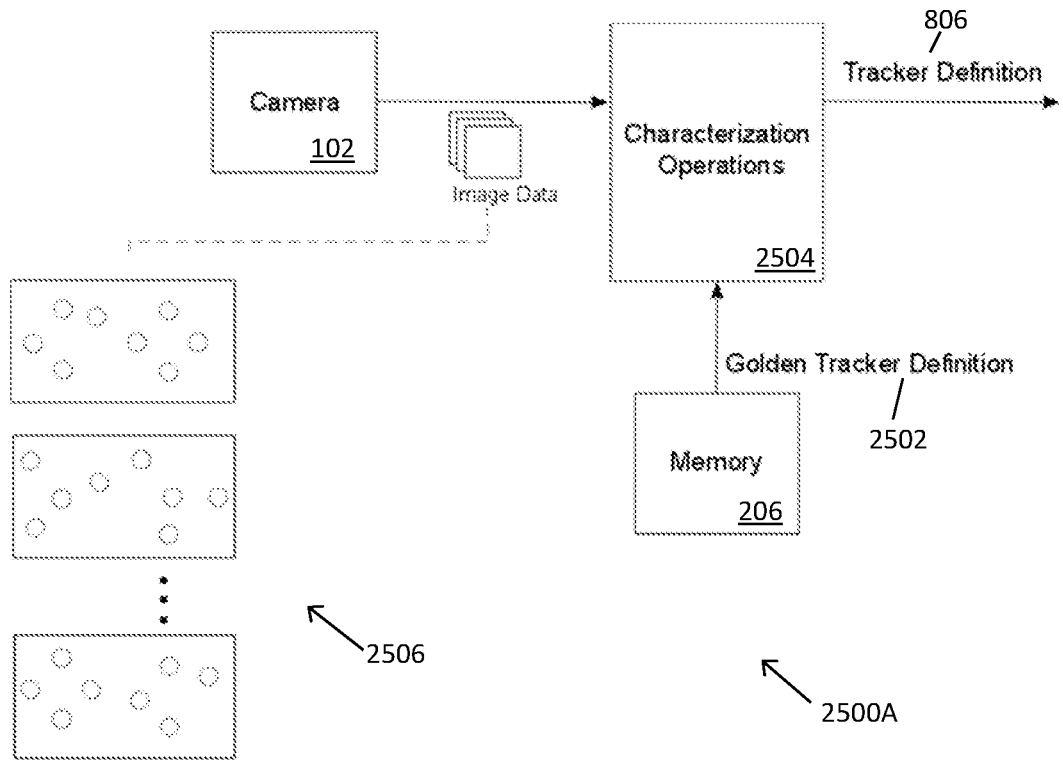
FIGS. 25A and 25B show block diagrams illustrating the inputs into characterization operations to determine a tracker definition and the tracker definition being used as an input into localization operations respectively.
Figure 25B:
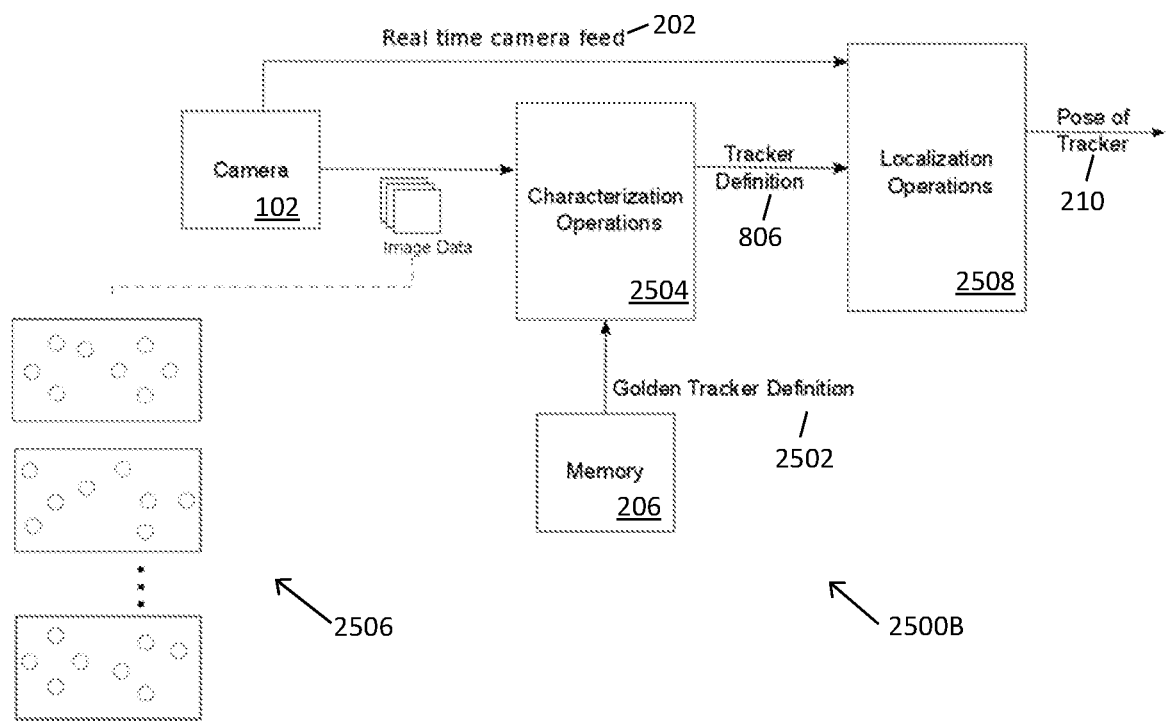

FIG. 25A depicts the method 2500A as a block diagram of the inputs into characterization operations 2504 to calculate a Tracker Definition 806. Using image data 2506 from the camera 102 and the Golden Tracker Definition 2502, characterization operations 2504 can optimize and calculate the Tracker Definition 806. The Tracker Definition 806 may further be used as an input to localization operations 2508 to calculate the pose of the tracker 210 as in the method 2500B illustrated in FIG. 25B or be displayed to a user on a display unit 1206.

Figure 26:
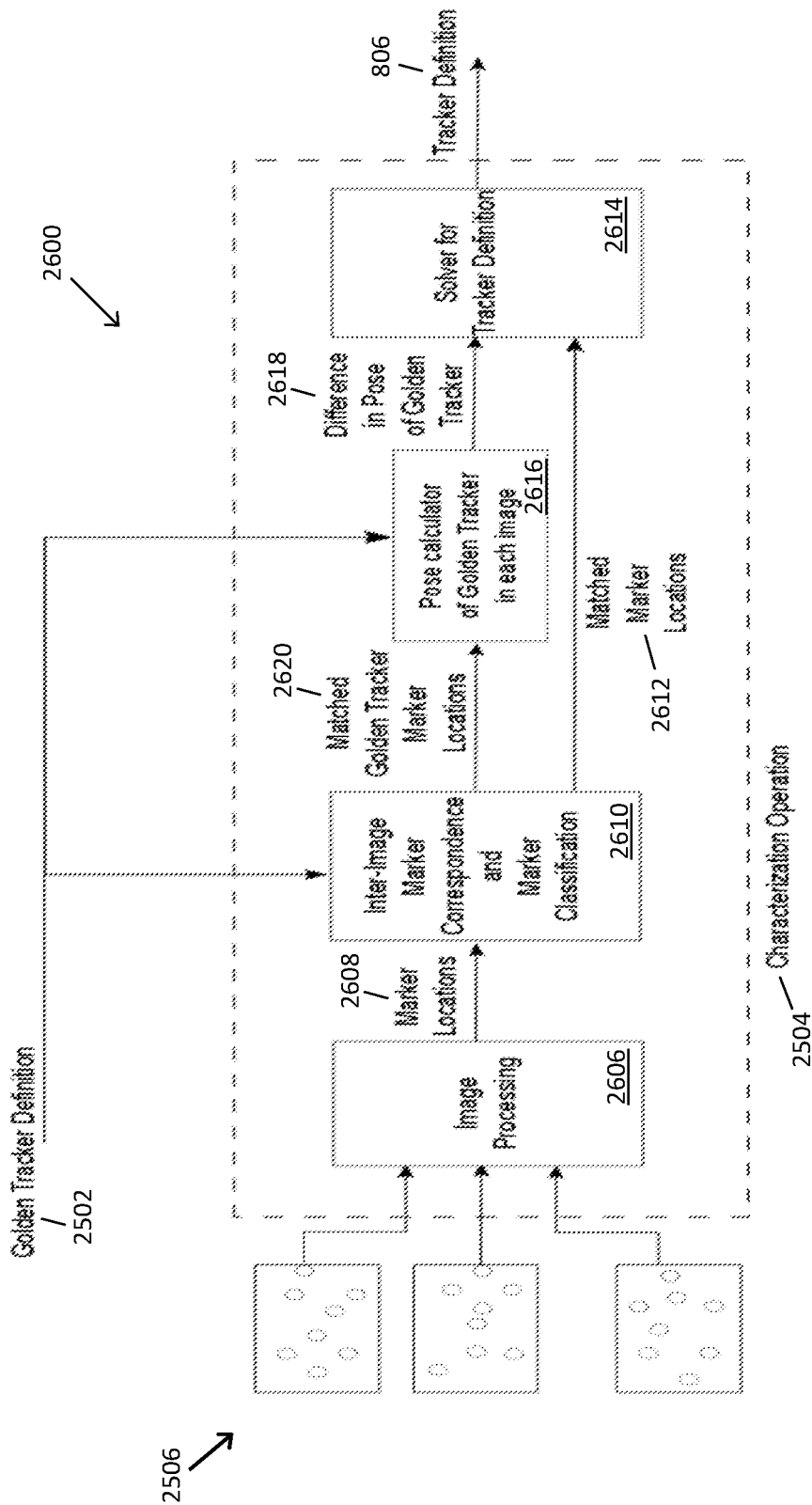
FIG. 26 shows a characterization operation as an example for clarity.

An exemplary method 2600 of characterization operation using the Golden Tracker 2106 is shown in FIG. 26. The figure describes multiple stages of the characterization operation 2504. First, image data 2506 (comprising multiple 2D images of the tracker and Golden Tracker appearing together) is received from the camera 102 and processed 2606 to discern the optically detectable features 108 (e.g., markers) in each image. The locations of each optically detectable feature, also called the marker locations 2608, in an image are used in the next stage where the operations create a correspondence between an optically detectable feature of one image and the same feature in a second image, and so on 2620. In addition to matching markers between each image, each marker is also classified to determine whether it is part of the Golden Tracker 2106 or the tracker 106, 2610. For example, this classification may be performed by optimizing subsets of matched markers for a best fit with the Golden Tracker Definition 2502. If the Golden Tracker Definition 2502 fits two subsets of matched markers, the characterization operation may conclude that the Tracker Definition 806 is identical to the Golden Tracker Definition 2502, thus reflecting a scenario where the tracker 106 and Golden Tracker 2106 have an identical physical geometry. If not, the operation further uses the matched marker locations of the Golden Tracker 2612 to calculate the pose of the Golden Tracker 2106 between the various images 2616 (thus computing a difference in the various vantage points of the optical sensor 102). The operation further solves 2614 for a Tracker Definition 806 using the matched marker locations of the tracker 2612 and the difference in the vantage point from which each image was captured (i.e. the relative pose of the Golden Tracker between each image) 2618. Persons skilled in the art will understand that this is an exemplary operation, and that there may be a variety of operations that can be executed to perform such calculations.

Figure 27:
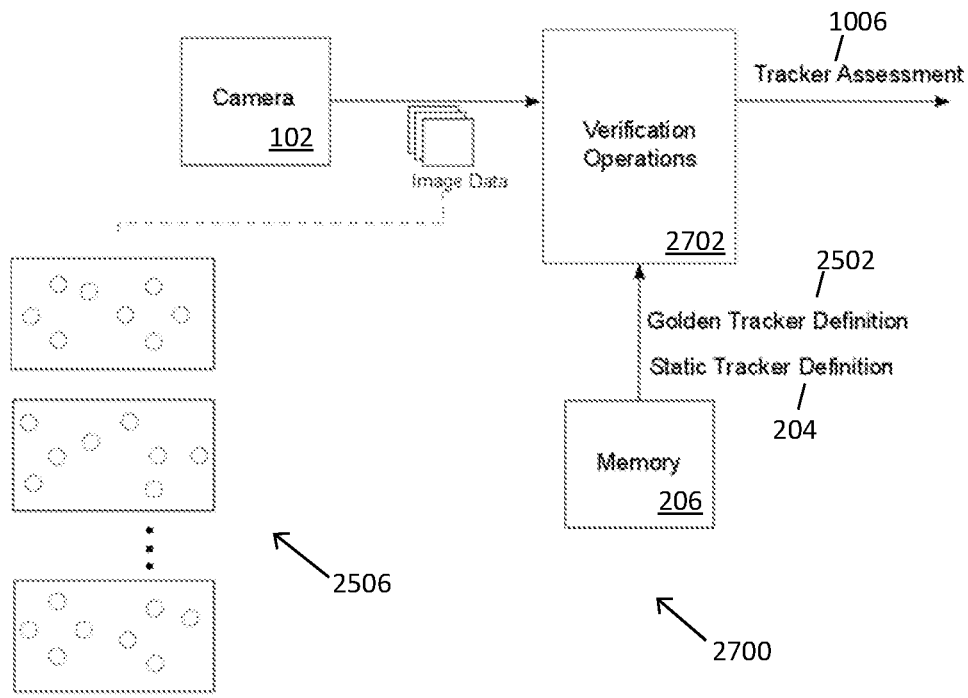
FIG. 27 shows a block diagram illustrating the inputs into verification operations to assess a tracker.

Similar to characterization, FIG. 27 illustrates a workflow 2700 where a tracker is assessed for accuracy with respect to a Static Tracker Definition 204. In addition to the Golden Tracker Definition 2502, the method further utilizes the Static Tracker Definition 204 to optimize the received image data 2506 and assess the accuracy of the tracker. It is possible that for some surgical applications, deviation of a tracker 106 from a Static Tracker Definition 204 is unacceptable. Through verification operations 2702, the method may generate a Tracker Assessment Parameter 1006 to quantify this deviation. This parameter may then be used by the computing unit 104 during a localization procedure to determine whether the tracker 106 being used is accurate or not. Some of the examples of how the Tracker Assessment Parameter 1006 is presented could be a Boolean flag, a single numerical value or multiple numerical values associated with how closely the Tracker Definition 806 matches the Static Tracker Definition 204, etc.

Figure 28A:
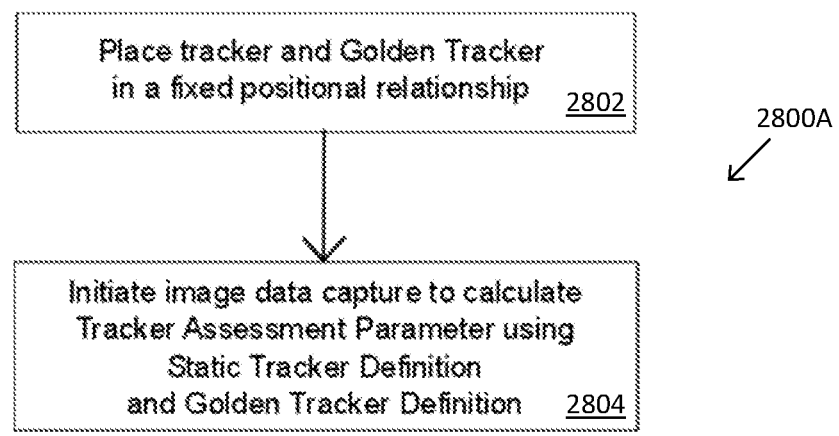
FIGS. 28A and 28B depict a user method and a computer-implemented method respectively to verify the accuracy of a tracker with respect to a Static Tracker Definition.
Figure 28B:
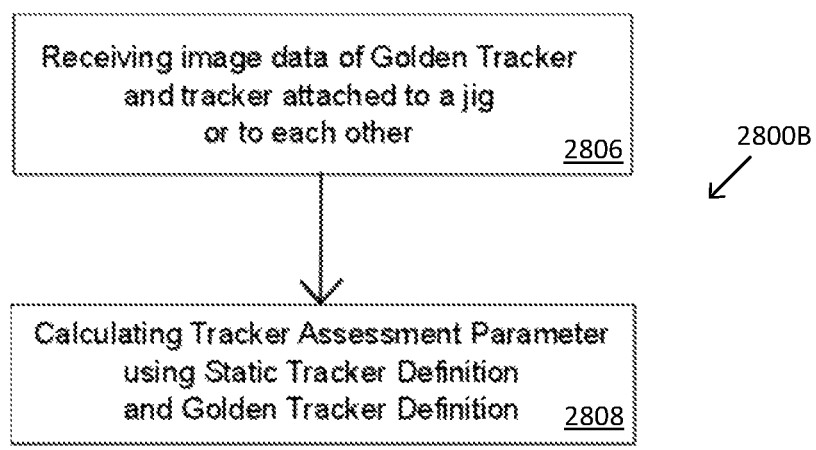

FIGS. 28A and 28B illustrate a user method 2800A and a corresponding computer implemented method 2800B to assess the tracker. A workflow executing on the computing unit 104 instructs the user to place the tracker 106 and the Golden Tracker 2106 in a fixed positional relationship 2802. The user may then initiate capture of image data 2506 by the optical sensor 102 from multiple vantage points 2804. The computing unit 104 receives image data 2506 of the tracker 106 and the Golden Tracker 2106 from the optical sensor 102, 2804. The computing unit 104 executes instructions to optimize and verify the accuracy of the tracker 106 with respect to the Static Tracker Definition 204 using the Golden Tracker Definition 2502, 2808.

Figure 29:
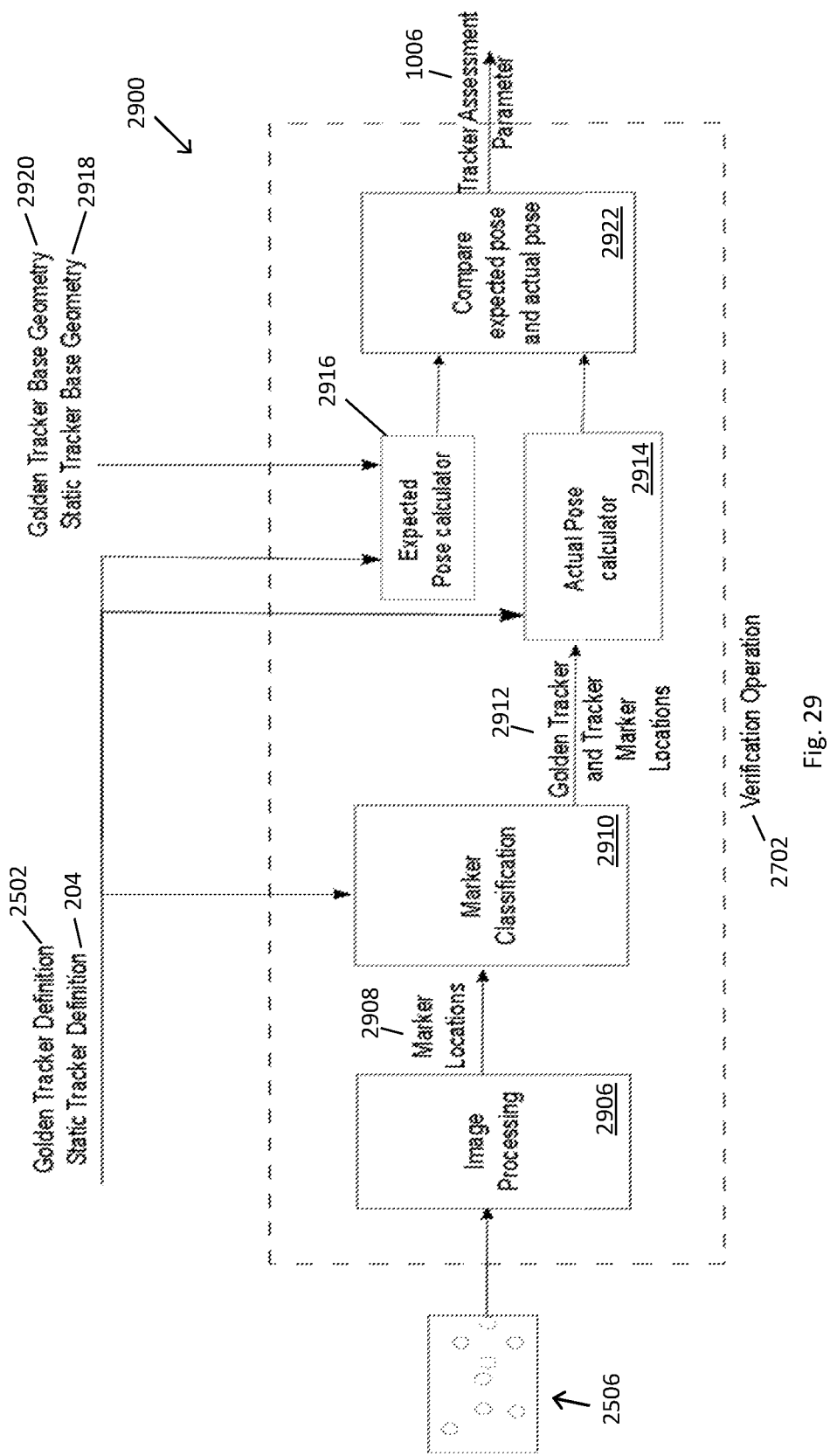
FIG. 29 shows a verification operation using one image as an example for clarity.

If the tracker 106 and the Golden Tracker 2106 are attached to each other and the Static Tracker Definition 204 includes the Static Tracker Base Geometry (i.e. the spatial relationship between the optically detectable features 108 and the base of the Static Tracker), and the Golden Tracker Base Geometry is known, only one image comprising the Golden Tracker 2106 and tracker 106 is required to assess the accuracy of the tracker 106. Reference is now made to FIG. 29 is a block diagram that depicts an exemplary method 2900 of performing the verification operations 2702. Image data 2506 is processed 2906 to identify the location of the markers 2908 in the image data 2506. Using the Static Tracker Definition 204, the Golden Tracker Definition 2502 and the marker locations 2908, the marker locations are then classified 2910 to determine the location of the tracker markers and the golden tracker markers, respectively 2912. The actual pose is calculated 2914 using the location of the tracker markers and the golden tracker markers 2912, the static tracker definition 204 and the golden tracker definition 2502. The expected pose is calculated 2916 using the static tracker definition 204, the golden tracker definition 2502, the known static tracker base geometry 2918 and the golden tracker base geometry 2920 A Tracker Assessment Parameter 1006 is generated by comparing an expected relative pose between the Golden Tracker 2106 and the tracker 106, and an actual relative pose 2922.

Figure 30A:
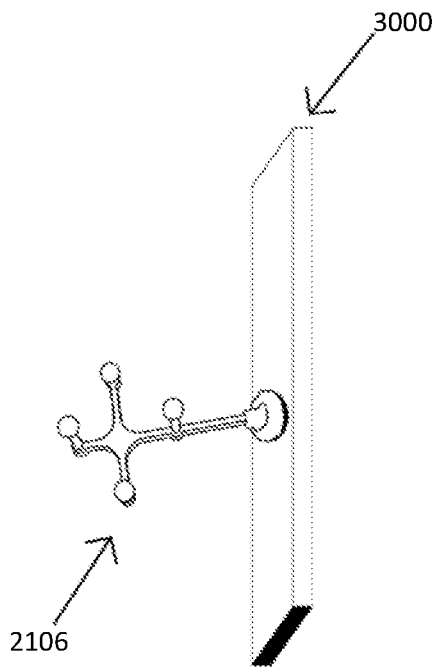
FIGS. 30A and 30B depict a characterisation jig as a vertical plate having tracker mounting surfaces on opposite faces.
Figure 30B:
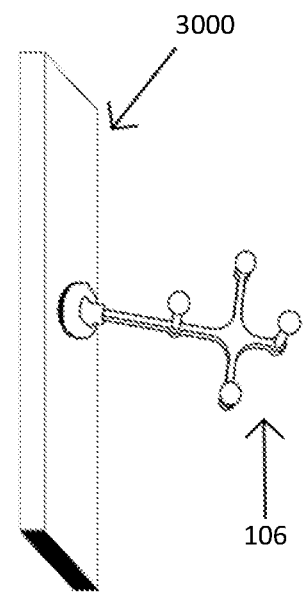

Expanding further on the previously described example of use in the operating room, the sterile nurse assisting the surgeon during the operation can handle the tracker 106 and the characterization jig 2202, 2204. The second, non-sterile nurse can handle the non-sterile Golden Tracker 2106. The non-sterile nurse can attach the Golden Tracker 2106 to one of the two tracker mounting locations 304 on the characterization jig 2202, 2204. This characterization jig 2202, 2204 may be configured to allow both the tracker 106 and Golden Tracker 2106 to be attached to the characterization jig 2202, 2204 simultaneously without compromising the sterility of the tracker 106 (i.e. there is no risk of contaminating the tracker 106) while allowing the tracker 106 and the Golden Tracker 2106 to appear in the field of the view of the optical sensor 102. For example, the characterization jig 2202, 2204 may have a tracker mounting location 304 on each end of its length for both the tracker 106 and the Golden Tracker 2106 such that the mounting locations 304 are separated by a sufficient distance to avoid contact between the tracker 106 and Golden tracker 2106 (the distance not being so large that either the tracker 106 or the Golden Tracker 2106 falls outside of the field of view of the optical sensor 102). For example, as shown in FIGS. 30A and 30B the characterization jig 3000 may be a flat plate intended to be used vertically such that there is a tracker mounting location 304 on each side (e.g. opposite faces of the jig), etc. It may not be necessary to obtain image data 2506 with both the tracker 106 and the Golden Tracker 2106 in the field of view simultaneously.

It is contemplated that the optical sensor 102 may capture image data 2506 serially by capturing a primary image of the tracker 106 attached to a mounting location 304 and a secondary image of the Golden Tracker 2106 attached to another mounting location 304 while the optical sensor 102 is positioned at a given vantage point. Such use avoids any possibility of contamination while the tracker 106 and Golden Tracker 2106 are attached or removed from the mounting locations 304 on the characterization jig 3000 and the method of use may be repeated to capture image data 2506 from multiple vantage points. The tracker 106 may then be characterized or verified using the image data 2506 and the Golden Tracker Definition 2502 by instructions executing on the computing unit 104.

These methods of use where the Golden Tracker 2106 does not have to be sterilized may be advantageous. Sterilization may reduce the accuracy of the Golden Tracker 2106. This method of use further allows non-sterilisable materials to be used to manufacture the Golden Tracker 150. In addition, some of the design limitations of a tracker 106 meant for use in localization do not apply. For example, the Golden Tracker 2106 may be made of cheaper materials in order to reduce costs. Alternatively, it may be manufactured using more expensive optically detectable features 108 if that lends higher accuracy to the measurements derived from it.

Tracker Characterization and Verification with Pivotal Characterization Jig

Systems, methods and components for tracker characterization and verification using a pivotal characterization jig are predominantly described with reference to FIGS. 1-2, 6, and 31-39C though it will be understood that there is some overlap with concepts, etc. to earlier or later described embodiments herein. There is described a system comprising: a characterization jig comprising a base, at least two tracker mounting locations and a pivot leg, the pivot leg having a first end that attaches the pivot leg to the characterization jig and a second end having a pivot point; and a computer-readable storage device storing instructions which, when executed on a computing unit, configure the computing unit to: receive a first set of articulation images of a tracker from an optical sensor attached to a sensor mounting location when the tracker is attached to a first tracker mounting location on the characterization jig and the characterization jig is pivoted about the pivot point while the pivot point is mated with a first mating member of a surface; receive a second set of articulation images of the tracker from the optical sensor attached to the sensor mounting location when the tracker is attached to a second tracker mounting location on the characterization jig and the characterization jig is pivoted about the pivot point while the pivot point is mated with a second mating member of the surface; and calculate at least one of: A) a Tracker Definition that comprises a Tracker Base Geometry using knowledge that the first set of articulation images and the second set of articulation images are of the tracker being articulated about the pivot point, a spatial relationship between the first tracker mounting location and the second tracker mounting location, a Pivot Tracker Mount Spatial Relationship, the first set of articulation images and the second set of articulation images; and B) a Tracker Assessment Parameter using knowledge that the first set of articulation images and the second set of articulation images are of the tracker being articulated about the pivot point, a spatial relationship between the first tracker mounting location and the second tracker mounting location, a Pivot Tracker Mount Spatial Relationship, the first set of articulation images, the second set of articulation images, and a Static Tracker Definition comprising a Static Tracker Base Geometry.

The first set of articulation images and the second set of articulation images may each comprise at least four distinct images of the optically detectable features of the tracker.

The pivot feature and at least one of the first mating member and the second mating member may further comprise a magnetic component to allow a magnetic connection between them.

The first mating member and second mating member may be coincident.

At least one of the first mating member and the second mating member may be provided on a sterilization tray containing medical instruments for use in a surgical procedure.

The characterization jig may comprise an identifier to identify the spatial relationship between the first tracker mounting location and the second tracker mounting location of the characterization jig. The identifier may be readable by the optical sensor.

The characterization jig may comprise an identifier to identify the Pivot Tracker Mount Spatial Relationship. The identifier may be readable by the optical sensor.

The characterization jig may be made entirely of sterilisable material.

The instructions may configure the computing unit to calculate the Tracker Assessment Parameter and provide it to a display unit.

The instructions may configure the computing unit to calculate the Tracker Assessment Parameter and the system may further comprise a display unit to display the Tracker Assessment Parameter.

User instructions may be displayed to a user on a display unit.

The instructions may configure the computing unit to calculate the Tracker Definition and the computer readable storage device may further comprise instructions to measure a pose of an object attached to the tracker using the Tracker Definition. The object may be a surgical tool.

There is described a system comprising: a characterization jig comprising a base and at least two tracker mounting locations; an optical sensor enclosed in a shroud and placed within a clamp, the shroud and the clamp having respective mating surfaces; and a computer-readable storage device storing instructions which, when executed on a computing unit, configure the computing unit to: receive a first set of articulation images of a tracker from the optical sensor when the tracker is attached to a first tracker mounting location on the characterization jig and the optical sensor and shroud is articulated within the clamp; receive a second set of articulation images of the tracker from the optical sensor when the tracker is attached to a second tracker mounting location on the characterization jig and the optical sensor and shroud is articulated within the clamp; and calculate at least one of: A) a Tracker Definition that comprises a Tracker Base Geometry using knowledge that the first set articulation images and the second set of articulation images are obtained from the optical sensor being articulated about a center of the clamp, a spatial relationship between the first tracker mounting location and the second tracker mounting location, the first set of articulation images and the second set of articulation images; and B) a Tracker Assessment Parameter using knowledge that the first set articulation images and the second set of articulation images are obtained from the optical sensor being articulated about the center of the clamp, the spatial relationship between the first tracker mounting location and the second tracker mounting location, the first set of articulation images, the second set of articulation images, and a Static Tracker Definition comprising a Static Tracker Base Geometry. The first set of articulation images and the second set of articulation images may each comprise at least four distinct images of the optically detectable features of the tracker.

There is provided a computer implemented method comprising the steps of: receiving, by a computing unit, a first set of articulation images of a tracker from an optical sensor attached to a sensor mounting location when the tracker is attached to a first tracker mounting location on a characterization jig comprising a base, at least two tracker mounting locations and a pivot leg, the pivot leg having a first end that attaches the pivot leg to the characterization jig and a second end that has a pivot point, and the characterization jig is pivoted about the pivot point while the pivot point is mated with a first mating member of a surface; receiving, by the computing unit, a second set of articulation images of the tracker from the optical sensor when the tracker is attached to a second tracker mounting location on the characterization jig and the characterization jig is pivoted about the pivot point while the pivot point is mated with a second mating member of the surface; and calculating, by the computing unit, at least one of: A) a Tracker Definition that comprises a Tracker Base Geometry using knowledge that the first set articulation images and the second set of articulation images are of a tracker being articulated about the pivot point, a spatial relationship between the first mounting location and the second mounting location, a Pivot Tracker Mount Spatial Relationship, the first set of articulation images and the second set of articulation images; and B) a Tracker Assessment Parameter using knowledge that the first set articulation images and the second set of articulation images are of the tracker being articulated about the pivot point, a spatial relationship between the first mounting location and the second mounting location, a Pivot Tracker Mount Spatial Relationship, the first set of articulation images, the second set of articulation images, and a Static Tracker Definition. The first set of articulation images and the second set of articulation images may each comprise at least four distinct images of the optically detectable features of the tracker.

The method may further comprise providing, by the computing unit, at least one of the Tracker Definition or the Tracker Assessment Parameter as calculated for use in a localization procedure.

There is described a characterization jig comprising a base, the base having a top side and a bottom side, the top side comprising at least two tracker mounting locations and the bottom side comprising a pivot leg, the pivot leg further comprising a first end to attach to the bottom side of the characterization jig and a second end comprising a pivot point about which the characterization jig can be articulated.

In the characterization jig, the first end of the pivot leg may be a hinge joint movable in one degree of freedom and the bottom side has a slot customized to accommodate a length of the pivot leg.

This document describes two systems—one for localization and the other for characterization. It is to be understood that these may be distinct systems that utilise the same hardware such as the optical sensor to capture images and the computing unit to execute instructions. These systems may also be distinct systems that use different hardware. It is also possible that these distinct systems communicate with each other to present a seamless user experience but optionally utilise the same hardware. Alternatively, the characterization system may be used separately from the localization system. For example, the characterization system may be used as part of quality control at a manufacturing site while manufacturing a localization system for use in a surgical setting. The hardware and software used to characterize the tracker may be completely distinct.

A characterization and/or verification system described below uses images of a tracker comprising optically detectable features that were obtained from the optical sensor while either the optical sensor or tracker is articulated about a geometrical constraint that allows a computing unit to execute operations to calculate the value of the Tracker Definition or Tracker Assessment Parameter.

In one such example of a characterization system, a characterization jig may be used with the components of the localization system such as the optical sensor (e.g., a camera) and the tracker with optically detectable features (e.g., markers). The camera may be the same hardware used for localization or may be a part of a computing unit or laptop e.g., a webcam on a laptop. The camera may be attached to a platform.

The characterization jig comprises a rigid base with a top side and a bottom side, a pivot leg with two ends, and at least two mounting locations on the top side upon which a tracker can be attached. Two objects are "attached" when both are in contact with each other to form a connection and there is a holding mechanism to enforce the connection. The attachment may be rigid and removable, for example, selectively removable. It may also be repeatable by virtue of the type of mechanism used for attachment, for e.g., a kinematic mount.

The pivot leg is a shaft-like attachment (temporary or permanent) to the jig and has two ends. A first end attaches the pivot leg to the bottom side of the jig, opposite the top side of the jig that comprises tracker mounting locations. A second end comprises a pivot point (e.g. a tip) such that the entire characterization jig can be articulated about the point. In this document, "articulate" is a verb referring to the movement of an object (or a part of it) within a constraint such that the movement is restricted about a single center of rotation. Multiple methods of attachment of the pivot leg to the jig are contemplated. For example, the pivot leg may be a standalone piece that is attached to the jig using a helical thread running around the first end; the pivot leg may be attached to the jig as a hinge joint movable in one degree of freedom and foldable into a slot customized to accommodate the length of the pivot leg, the slot being located on the bottom side of the characterization jig; there may be a strong magnetic connection between the first end of the pivot leg and the bottom side of the characterization jig to allow a user to articulate the jig about the pivot point without slippage, etc.

The jig may be made of sterilisable material to allow use within an operating room or any such sterilized environment. The geometry of the characterization jig is known to the computing unit. This implies that the physical shape, size, features etc. of the characterization jig are known since the jig may be manufactured under strict tolerances. The characterization and/or verification operations described herein utilize known spatial relationships between the various components of the characterization jig.

These known spatial relationships or any of the other geometrical characteristics of the jig may be pre-loaded into the memory of the computing unit of the characterization system (e.g. as a hard-coded value, as a 3D model, etc.) and used in the calculation of the Tracker Definition or the calculation of a Tracker Assessment Parameter to verify of the accuracy of a tracker with respect to a Static Tracker Definition. The Tracker Assessment Parameter may be displayed to a user on a display unit. Using this configuration of the jig, the computing unit may optionally calculate a Tracker Base Geometry (i.e. how the optically detectable features relate to the base of the tracker) as part of the Tracker Definition. It may also be possible to verify the accuracy of the tracker with respect to the Static Tracker Definition that comprises a Static Tracker Base Geometry.

An Inter Tracker Mount Spatial Relationship (i.e. the spatial relationship between two tracker mounting locations on the jig) and a Pivot Tracker Mount Spatial Relationship (i.e. the spatial relationship between any one of the tracker mounting locations and the pivot point on the second end of the pivot leg of the jig) may be stored in memory as a numerical representation of the relative poses between the mounting locations represented as rotation matrices, quaternions, euler angles, translational vectors, Cartesian distances etc. The characterization jig comprising the pivot leg may be manufactured to meet a specific Inter Tracker Mount Spatial Relationship and/or Pivot Tracker Mount Spatial Relationship. The same spatial relationships may be accessible to the computing unit. For example, the numerical representation of the spatial relationships may be data stored in memory, preferably in a manner that prevents or reduces the possibility of deletion. There may be an identifier such as a barcode, QR-code, URL, etc. on the characterization jig itself that identifies the relationships. The identifier may be read using the optical sensor and used to look up the relationships that are stored in memory or remotely on a network.

To characterize the tracker of verify the accuracy of the tracker, the camera captures images specifically for characterization (also called "articulation image data" in this document) of the tracker when the tracker is attached to the tracker mounting locations on the characterization jig, and the jig is articulated about the pivot point of the pivot leg. Using known spatial relationships of the characterization jig (such as the Inter Tracker Mount Spatial Relationship and the Pivot Tracker Mount Spatial Relationship) and knowing that the articulation image data is obtained while the jig is pivoted about the pivot point, the computing unit can execute instructions to calculate a Tracker Definition or a Tracker Assessment Parameter. When articulated about a point, a person skilled in the art will understand that a minimum of four distinct images during each articulation will be required in order to calculate a center of a sphere. The characterization and verification processes are further described below.

Figure 31:
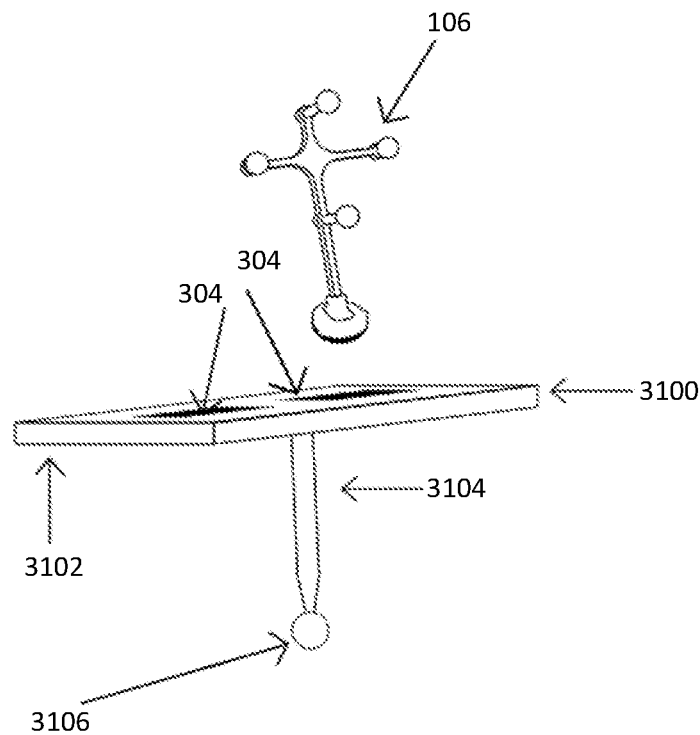
FIG. 31 illustrates a characterization jig with two tracker mounting locations and a pivot leg, as an example for clarity.

Reference is now made to FIG. 31 that illustrates the characterization jig 3100 with the pivot leg 3104 comprising a pivot point 3106 affixed to the rigid base 3102. The pivot leg 3104 is further configured to mate with a mating member on a rigid surface. The mating member on the rigid surface may be such that a user can access it repeatedly to articulate the characterization jig 3100.

The characterization jig 3100 is not to be limited to the examples shown above. For example, a surgical probe with a tip may be articulated about the tip within a hemi-spherical divot on the surface. In addition to its utility in the process of tracker characterization, the probe may have additional utility for navigation or localization. The probe may provide a first mounting location 304 for the tracker 106. A second mounting location 304 may be provided by a separate attachment to the probe that attaches in a fixed and repeatable manner to form a characterization jig 3100 with a known Inter Tracker Mount Spatial Relationship 802 between the mounting locations and a known Pivot Tracker Mount Spatial Relationship.

Figure 32:
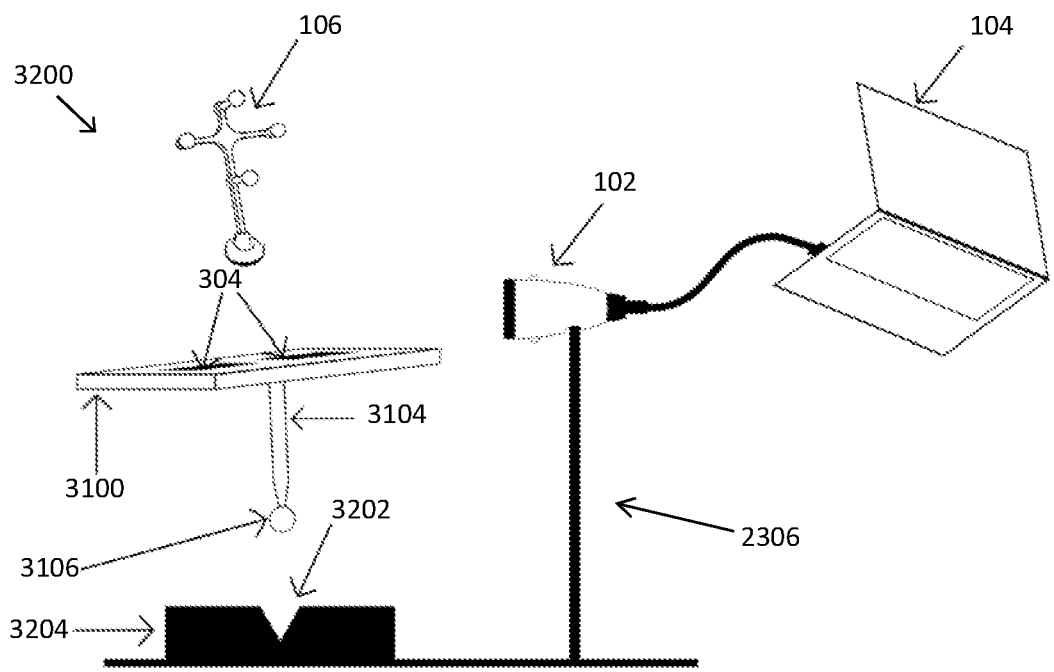
FIG. 32 illustrates a system including the jig and an optical sensor connected to a computing unit.
Figure 33:
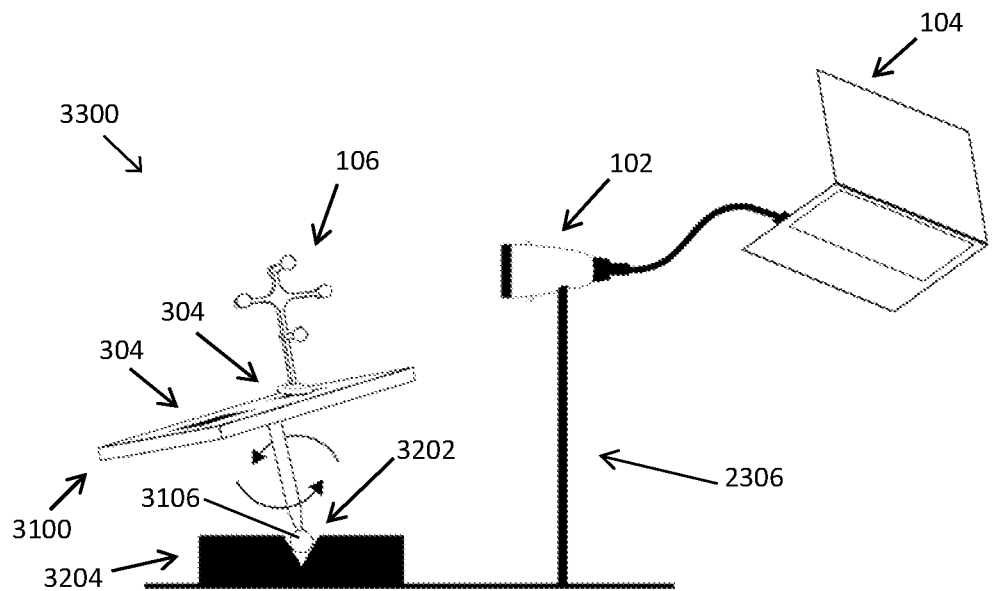
FIG. 33 illustrates the jig being articulated in a rotatory motion.

Reference is now made to FIG. 32 showing a configuration of a system 3200 using the characterization jig 3100 with at least two tracker mounting locations 304 and the pivot leg 3104 as an example for clarity. The pivot point 3106 of the pivot leg 3104 is mated with the mating member 3202 on the rigid surface 3204. A user attaches the optical sensor 102 (e.g.: a camera) to a sensor mounting location 306 or platform 2306. The optical sensor 102 is in communication with a computing unit 104. The computing unit 104 may provide corresponding user instructions. The sensor mounting location 306 or platform 2306 may optionally be on the same rigid surface 205 as the mating member 3202. The spatial relationship between the sensor mounting location 306 or platform 2306 and the mating member 3202 is not required to be known to the computing unit 104. The user attaches the tracker 106 to the tracker mounting locations 304 on the characterization jig 3100 and articulates the characterization jig 3100 while the tracker 106 is within a field of view of the optical sensor 102. Reference is now made to FIG. 33 that depicts the configuration of a system 3300 where the characterization jig 3100 is being articulated while the pivot point 3106 is mated with the mating member 3202 on the rigid surface 3204. As the characterization jig 3100 is articulated within the mating member 3202, the optical sensor 102 captures articulation image data.

In further variations of this configuration of the system, the mating member 3202 and the pivot point 3106 may each comprise a magnetic component to allow the mating member 3202 and the pivot point 3106 of the characterization jig 3100 to mate magnetically. This allows a repeatable and stable mating connection between the mating member 3202 and the characterization jig 3100. The magnetic force may further assist a user in keeping the pivot point 3106 engaged with the mating member 3202 during articulation, thus potentially reducing errors introduced due to slippage of the pivot point 3106 within the mating member 3202 while articulating. The mating member 3202 may be provided on a sterilization tray containing medical instruments for use in a surgical procedure. The pivot leg 3104 and the mating member 3202 should be interpreted as broadly as possible. For example, while FIG. 32 depicts the pivot leg 3104 of the characterization jig 3100 and the mating member 3202 as a part of the rigid surface 3204, the locations or geometrical shapes of these components may be reversed such that the characterization jig 3100 comprises the mating member 3202 and the pivot leg 3104 is attached to the rigid surface 3204. This would allow the characterization jig 3100 to be stationary while the surface 3204 (for example, in the form of a rectangular tray with a sensor mounting location 306) is articulated about the pivot point 3106.

Figure 34A:
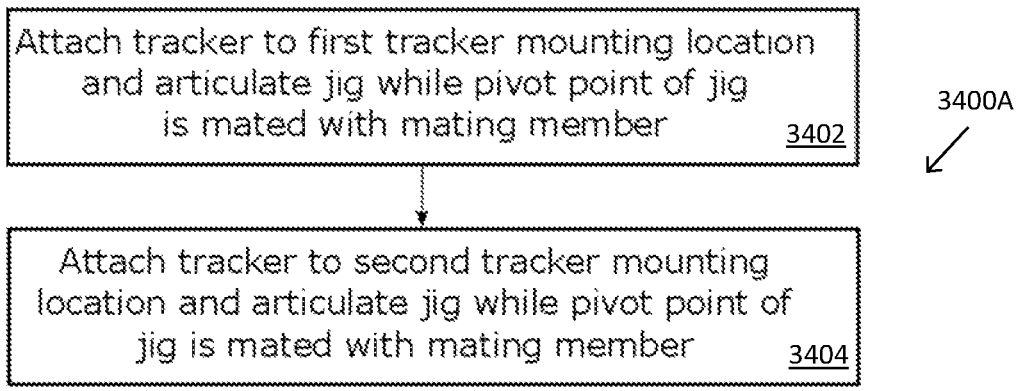
FIGS. 34A and 34B illustrate a method of use and a computer implemented method of use for calculating a Tracker Definition using image data collected during articulation.
Figure 34B:
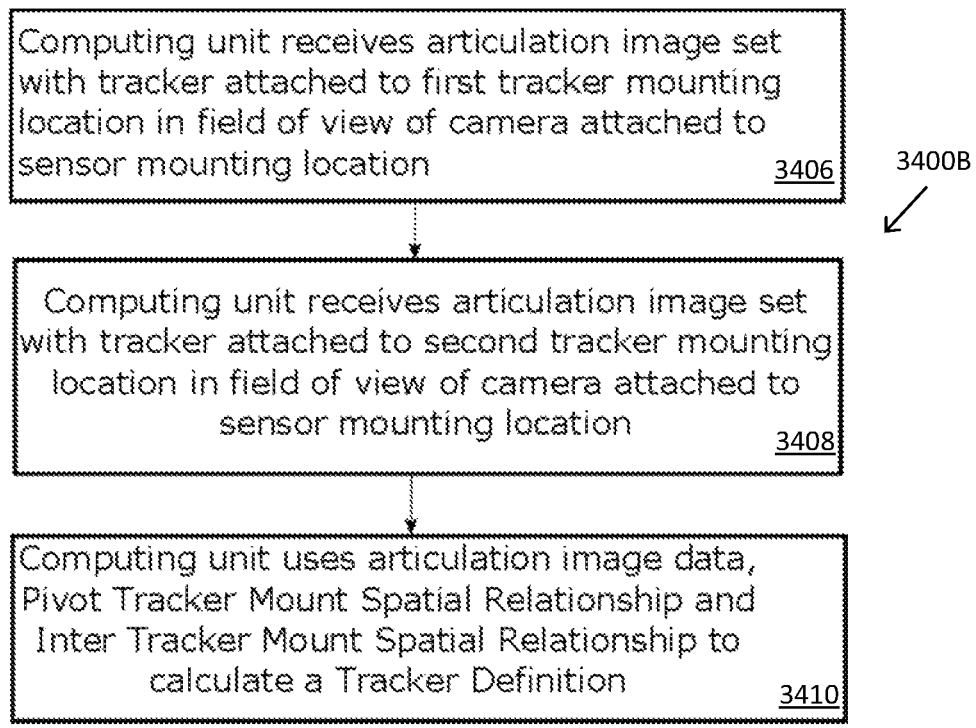

Reference is now made to FIGS. 34A and 34B. In a method of use and a corresponding computer implemented method to obtain a Tracker Definition 806, a camera 102 is rigidly attached to a sensor mounting location 306 and connected to a computing unit 104. In a first step 3402: A user attaches a tracker 106 (with an unknown Tracker Definition 806) to a first mounting location 304 on the characterization jig 3100; The user mates the characterization jig through its pivot leg 203 within a mating member 3202 on a rigid surface 3204 and articulates the characterization jig 3100, while the tracker 106 is in a field of view of the camera 102. The computing unit 104 receives a first set of articulation images 3406. In a second step 3404: The user then attaches the tracker 106 to a second tracker mounting 304 and articulates the characterization jig 3100 while the tracker 106 is in the field of view of the camera 102. The computing unit 104 receives a second set of articulation images 3408. Knowing that both sets of articulation image data is obtained by articulating the characterization jig 3100 about a fixed point, and using both sets of articulation image data, the Inter Tracker Mount Spatial Relationship 802, and the Pivot Tracker Mount Spatial Relationship 3612, the computing unit 104 executes instructions to calculate a Tracker Definition 806 for the tracker 106 using characterization operations 3410. This Tracker Definition 806 may also comprise a Tracker Base Geometry.

There may be multiple mating members 3202 available for use such that the characterization jig 3100 is placed within a first mating member 3202 to obtain a first set of articulation images, and a second mating member 3202 to obtain a second set of articulation images. It is not necessary to use the same mating member 3202 since the Pivot Tracker Mount Spatial Relationship 3612 is known. The first and second mating members 204 may optionally be coincident as shown in the figures of this document.

The sensor mounting location 306 and the tracker mounting locations 304 may be reversed such that there are two sensor mounting locations 306 on the characterization jig 3100 (in which case, the tracker 106 must be stationary while the articulation image data is captured). This may be advantageous where the tracker 106 does not have a base 2302 (e.g., if the tracker 106 is integrally formed with a tool), or where multiple trackers 106 are to be simultaneously characterized. The instructions executing on the computing unit 104 may be modified accordingly such that the calculated result includes the spatial relationship between the optical sensor 102 and its base, in addition to the Tracker Definition 806 (excluding Tracker Base Geometry). The calculation of this spatial relationship of the optical sensor 102 may further be useful in scenarios where the optical sensor 102 is attached to a tool. When the spatial relationship between an effector of a tool and the sensor attachment location is known and/or accessible to the computing unit 104 during navigation, the computing unit 104 may perform navigation with respect to the effector of the tool. FIGS. 35A-35D illustrate a group of sensor systems (3500A, 3500B, 3500C, 3500D) where an optical sensor 102 is attached to various tools, including a probe 1612, a robot manipulator 3502, a broach handle 3504 and a calibration tool 3506 respectively.

The computing unit 104 may comprise multiple, distributed processing units (e.g. characterization may be carried out on one computing unit 104, whereas intra-operative localization may be carried out by another computing unit 104). It will be evident to those skilled in the art what data must be transferred between the various computing units 104 to enable the functionality of the systems and methods described herein. Tracker characterization or verification may be performed on an ad-hoc basis as part of routine maintenance of trackers 106, or may be performed prior to each localization procedure that uses a tracker 106. A person skilled in the art will appreciate that the level of accuracy of measurements will improve with an increase in the number of mounting locations 306 for the camera 102 and the corresponding articulation image data captured by the camera 102.

Figure 35A:
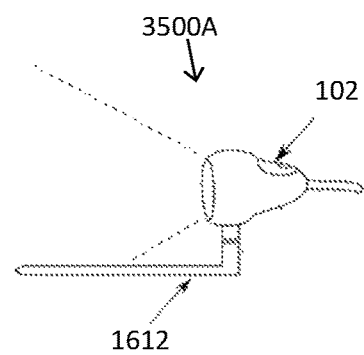
FIGS. 35A-35D illustrate examples of when a sensor is attached to a tool in different applications.
Figure 35B:
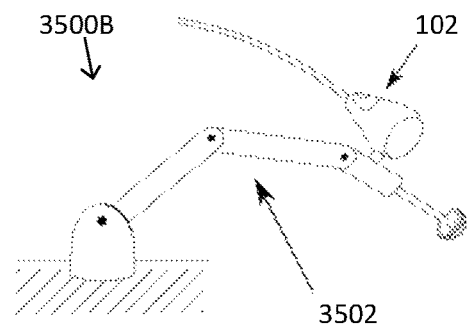
Figure 35C:
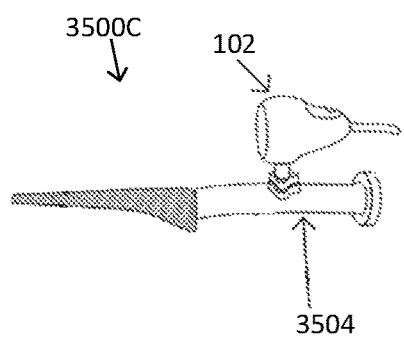
Figure 35D:
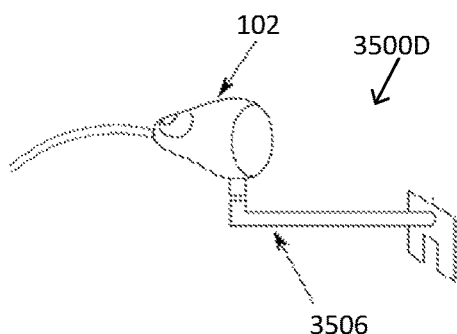
Figure 36A:
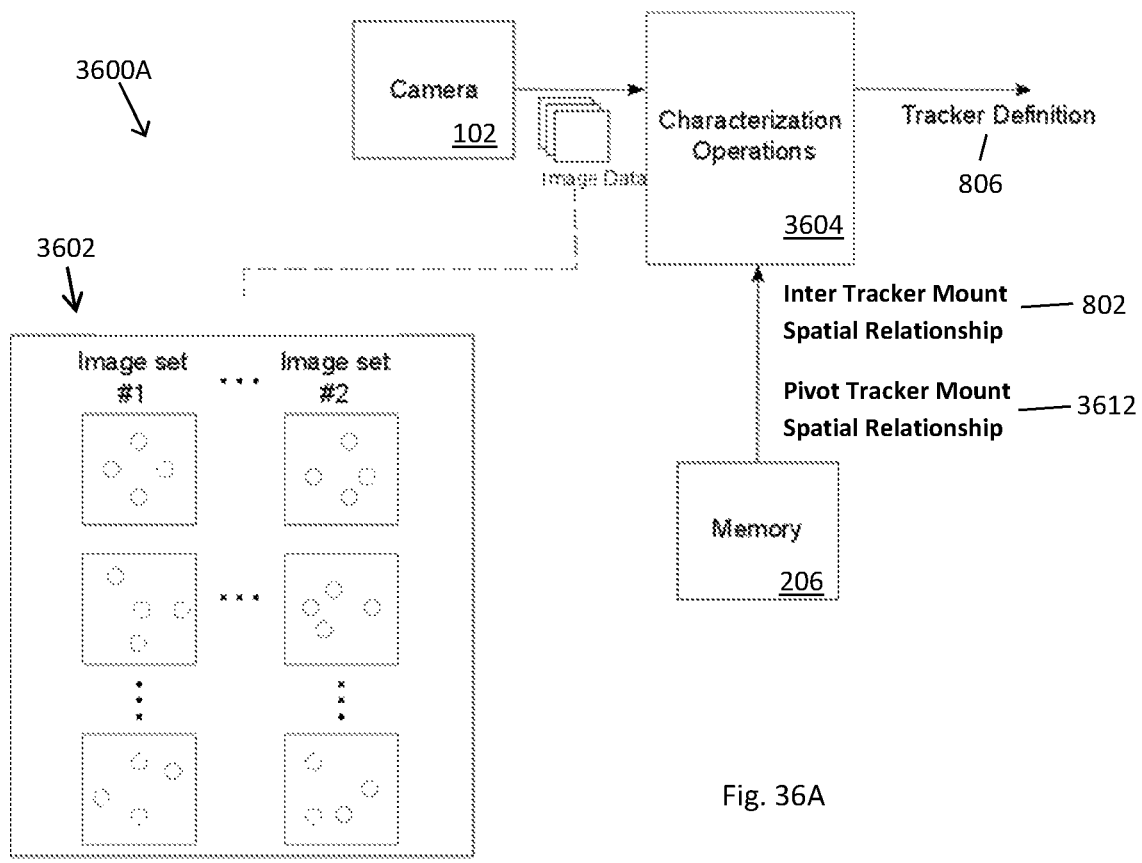
FIGS. 36A and 36B are block diagrams illustrating the inputs into characterization operations that determine a Tracker Definition and illustrating the output of a characterization operation being used as an input in localization operations.
Figure 36B:
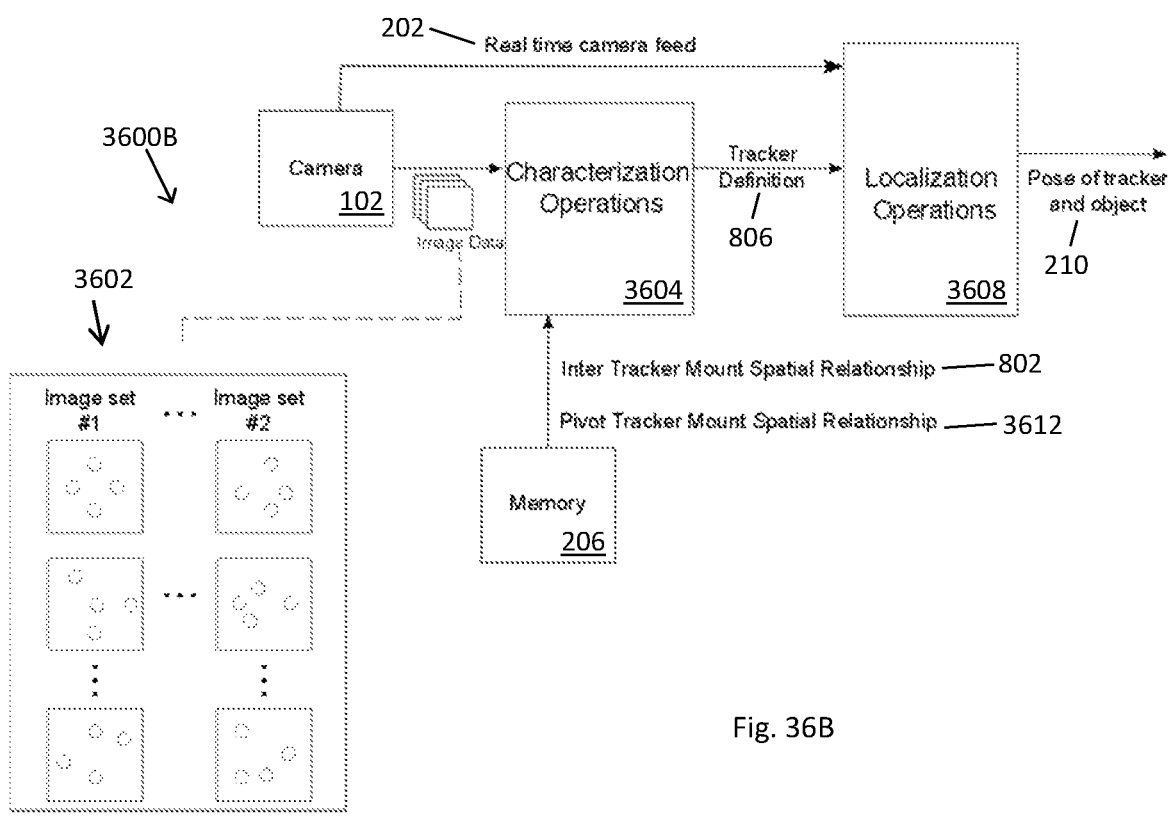

Reference is now made to FIG. 36A which illustrates the method 3600A and the flow of information to determine the Tracker Definition 806 of the tracker 106. Using the methods described above to obtain articulation image data 3602, characterization operations 3604 may calculate the Tracker Definition 806 using the Inter Tracker Mount Spatial Relationship 3610 and the Pivot Tracker Mount Spatial Relationship 3612, for example, by optimizing for the Tracker Definition 806 using the spatial relationships as constraints. FIG. 35B illustrates the output of a characterization operation 3604 being used in localization operations 3608 to calculate a pose of a tracker 210. As mentioned previously, the characterization jig 3100 may be configured as a probe 1612 that has utility in localization as well.

Figure 37:
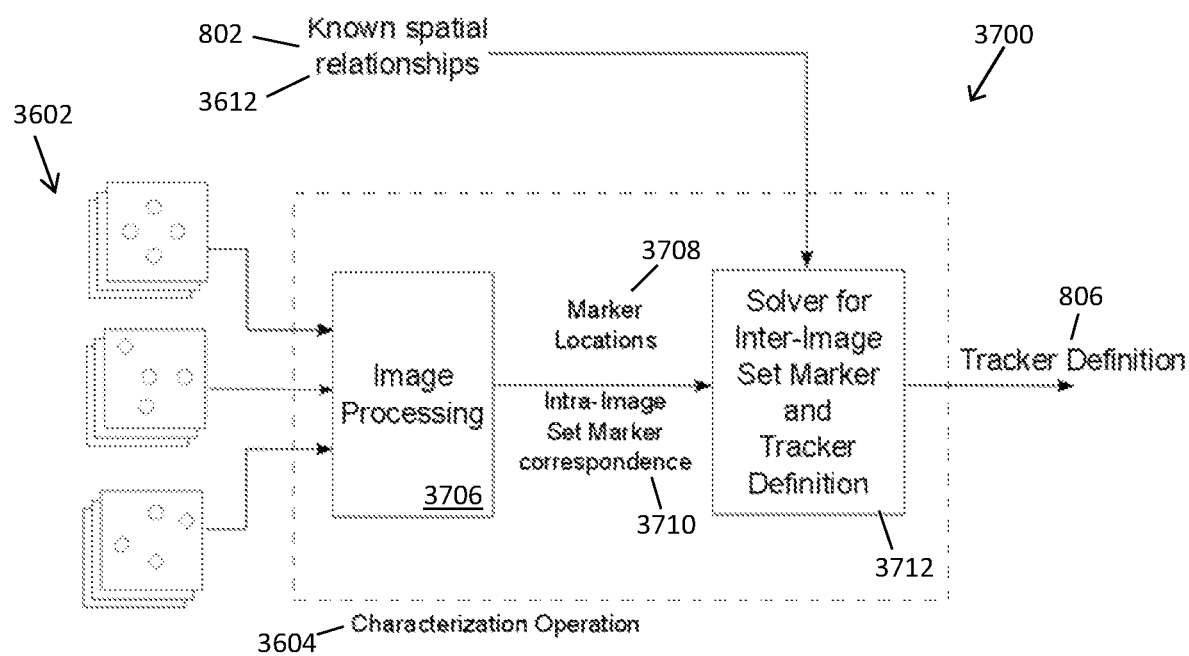
FIG. 37 shows a characterization operation as an example for clarity.

A exemplary method 3700 of the characterization operation 3604 is shown in FIG. 37 for clarity. First, articulation image data 3602 (comprising image sets of articulation images of the tracker 106 when the tracker is coupled to the characterization jig 3100 and the characterization jig 3100 is articulated about the pivot point 3106) is received from the camera 102 and processed 3706 to identify the location of the optically detectable features 3708 (e.g., markers) in each image. Note: The articulation of the characterization jig 3100 may be arbitrary with respect to direction/magnitude, or there may be some guidance provided to a user by the computing unit 104 to ensure that the articulation image data 3602 has the appropriate characteristics (e.g. number of images, angular span, direction, magnitude, etc.) to allow the computing unit 104 to execute instructions to accurately solve for the Tracker Definition 806. The operation also generates and maintains an intra-image set marker correspondence 3710 such that across each image in the articulation image set 3602, the optically detectable features 108 are associated with the same physical feature. Several methods for generating and maintaining the intra-image set marker correspondence 3710 may be used, and are evident to those skilled in the art. This process is repeated for each articulation image set 3602. The marker locations 3708 of each optically detectable feature 108, as well as the intra-image set marker correspondence 3710 are used in the next stage where, in conjunction with the Pivot Tracker Mount Spatial Relationship 3612 (i.e. how any one tracker mounting location 304 spatially relates to the pivot point 3106 of the characterization jig 3100), the Inter-Tracker Mount Spatial Relationship 3610 (i.e. how the tracker mounting locations 304 spatially relate to each other) and the knowledge that the articulation image sets 3602 are of a tracker 106 (attached to a characterization jig 3100) being articulated about a pivot point 3106, the Tracker Definition 806 is calculated 3712. The calculation of the Tracker Definition 806 (i.e. how the optically detectable features of the tracker 106 relate to each other) may include calculation of the Tracker Base Geometry (i.e. how the optically detectable features 108 of the tracker relate to the base of the tracker 2302). This calculation may utilize optimization routines where the unknown Tracker Definition 806 is being optimized, based on the marker locations 3708 in the articulation image sets 3602, the intra-image set marker correspondence 3710, and further utilizing the Pivot Tracker Mount Spatial Relationship 3612, the Inter Tracker Mount Spatial Relationship 3610 and the knowledge of the articulation being about a fixed point as optimization constraints. To solve for the Tracker Definition 806, it may be necessary to simultaneously solve for the inter-image set marker correspondence 3710.

Figure 38A:
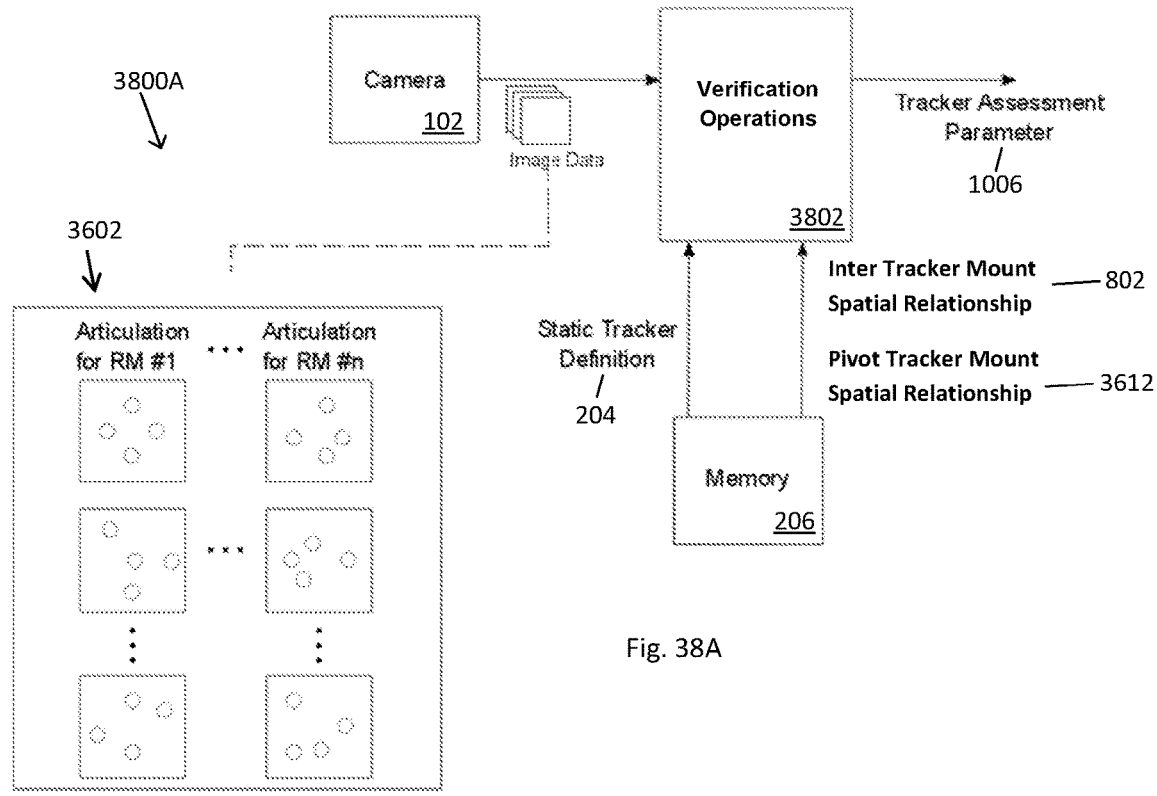
FIGS. 38A and 38B are block diagrams illustrating the inputs into characterization operations that assess the accuracy of a tracker and illustrating the output of a verification operation being used as an input in localization operations.
Figure 38B:
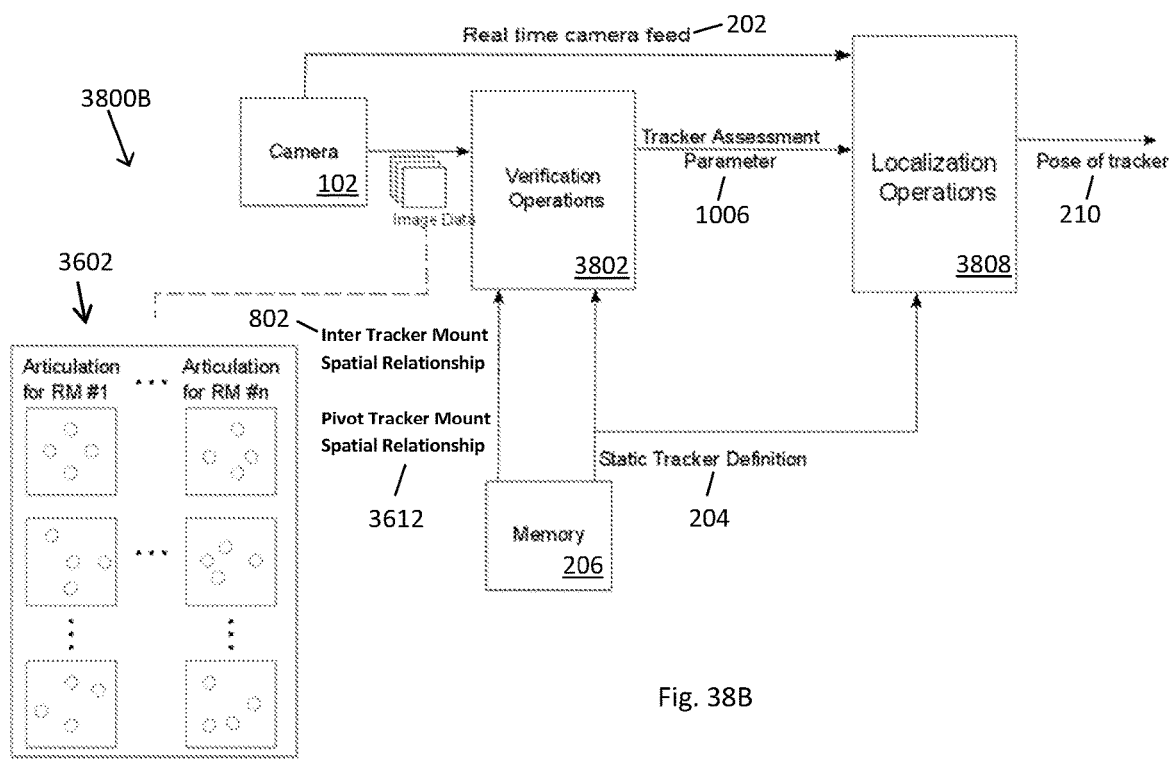

Reference is now made to FIG. 38A where there is illustrated the method 3800A and flow of information through verification operations 3802 to determine the accuracy of a tracker 106 with respect to a Static Tracker Definition 204. For example, verification operations 3802 may be set up as optimization operations that minimize error between the articulation image data 3602 and a Static Tracker Definition 204 further comprising a Static Tracker Base Geometry 2918 (if applicable). The Inter Tracker Mount Spatial Relationship 802 and the Pivot Tracker Mount Spatial Relationship 3612 provide optimization constraints. The operations may determine whether the Tracker Definition 806 comprising Tracker Base Geometry of a given tracker 106 is within a prescribed tolerance of the Static Tracker Definition 204 comprising Static Tracker Base Geometry 2918. The operations may further calculate a Tracker Assessment Parameter 1006 to quantify the deviation of the Tracker Definition 806 from the Static Tracker Definition 204. FIG. 38B illustrates a system where the output of a verification operation 3802 being used in localization operations 3808 to calculate pose of a tracker 210. The localization operations 3808 may use or discard the Static Tracker Definition 204, depending on the Tracker Assessment Parameter 1006.

Figure 39A:
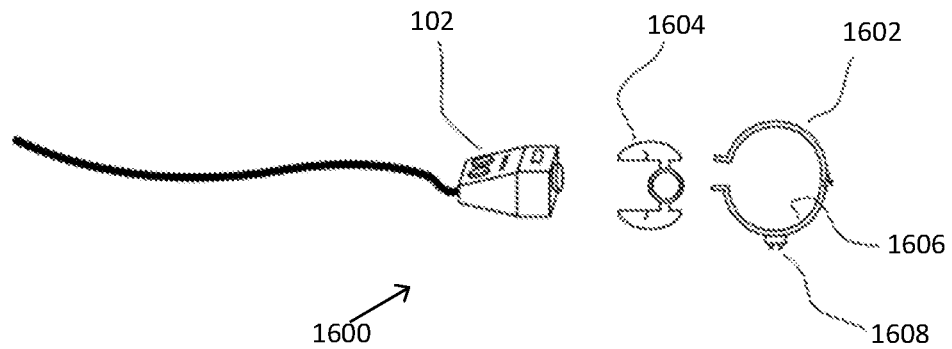
FIGS. 39A-39C show the optical sensor, a shroud and a clamp as individual components, as assembled, and as part of a characterization system respectively.
Figure 39B:
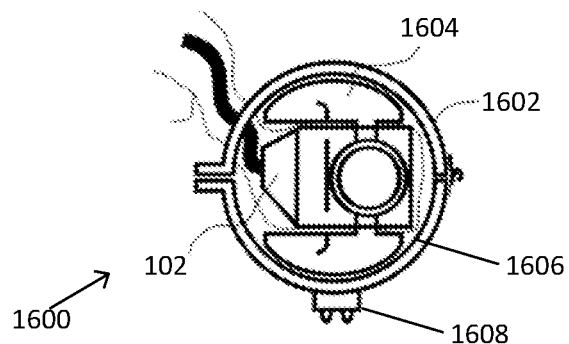
Figure 39C:
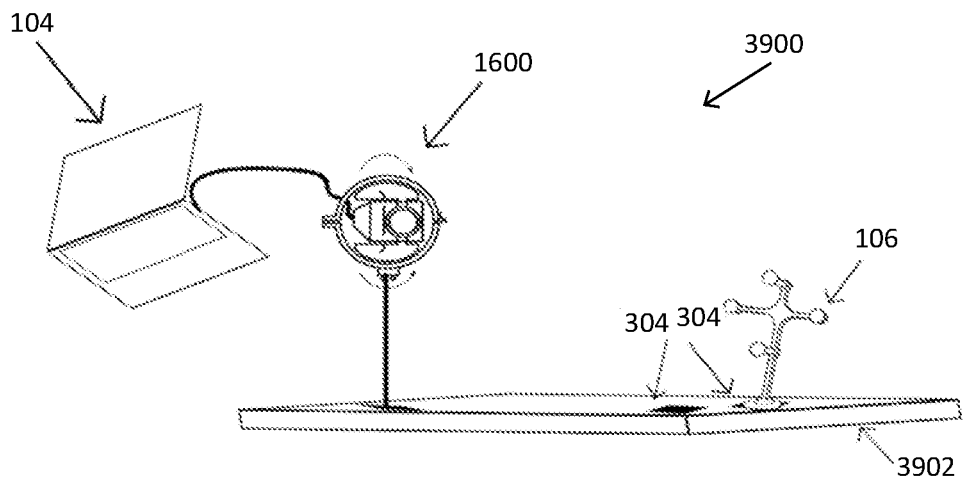

In another example of a characterization system, the optical sensor is articulated instead of the tracker attached to the jig. The optical sensor 102 is enclosed within a spherical shroud 1604 and clamp 1602 as illustrated in FIGS. 39A-39C. The optical sensor 102 (secured within the shroud 1604) may be articulated by virtue of its shape within the constraints of a geometry of the shroud 1604 and clamp 1602. For example, if the outer surface of the shroud 1604 and the inner surface of a clamp 1602 have curved mating surfaces (which curves define potions of a sphere), the optical sensor 102 will be articulated about a geometrical point that corresponds to the center of the sphere i.e. the center of the clamp 1602. As seen in system 3900 illustrated in FIG. 39C, the movement of the optical sensor 102 and shroud 1604 within the clamp 1602 allows the computing unit 104 to obtain articulation image data 3602 of the tracker 106. The tracker 106 may be attached to tracker mounting locations 304 on a characterization jig 3902 sequentially to obtain articulation image data 3602. The tracker mounting locations 304 may be provided by a characterization jig 160 with a known Inter Tracker Mount Spatial Relationship 802. Knowing that the articulation image data 3602 is obtained by articulating about a point, the system may be used to execute characterization operations 3604 to determine the Tracker Definition 806 of the tracker 106 using the articulation image data 3602, the Inter Tracker Mount Spatial Relationship 802 and the spatial relationship between the point (for e.g., the center of the clamp) and at least one of the tracker mounting locations 304. This spatial relationship is analogous to the Pivot Tracker Mount Spatial Relationship 3612 of the previous embodiment where the characterization jig 3100 comprises the pivot leg 3104. The calculated Tracker Definition 806 comprises the Tracker Base Geometry of the tracker 106 which describes how the optically detectable features 108 of the tracker 106 spatially relate to the base of the tracker 2302. As discussed above, this is useful in scenarios where there is a desire to know how the tracker 106 spatially relates to an object that it is attached to, through its base 2302 such that the localization system can provide relevant spatial measurements of the object.

Tracker Characterization with Inertial Sensor

Systems, methods and components for tracker characterization using an inertial sensor are predominantly described with reference to FIGS. 1-2, 6, and 40A-46 though it will be understood that there is some overlap with concepts, etc., to earlier or later described embodiments herein. There is provided a system comprising: a computer-readable storage device storing instructions and/or data which, when executed on a computing unit, configures the computing unit to: receive a first image of a tracker from an optical sensor at a first vantage point and a first inertial measurement from one or more inertial sensors, wherein the one or more inertial sensors are co-registered to the optical sensor and wherein the first image and first inertial measurement are obtained by the respective optical sensor and one or more inertial sensors when the tracker is at a resting position in a field of view of the optical sensor; receive a second image of the tracker from the optical sensor at a second vantage point and a second inertial measurement from the one or more inertial sensors, wherein the second image and second inertial measurement are obtained by the respective optical sensor and one or more inertial sensors when the tracker is at the resting position in a field of view of the optical sensor; and calculate at least one of: a Tracker Definition using the first image, the second image and a difference in orientation in at least 2 DOF between the first vantage point and the second vantage point; and a Tracker Assessment Parameter using the first image, the second image, the difference in orientation in at least 2 DOF between the first vantage point and the second vantage point, and a Static Tracker Definition.

The computing unit may be further configured to calculate the difference in orientation in at least 2 DOF between the first vantage point and the second vantage point using the first inertial measurement and the second inertial measurement.

Each of the one or more inertial sensors comprises any of an accelerometer, a gyroscope and a magnetometer.

The computing unit may be configured to: calculate a Tracker Definition; calculate a Tracker Base Geometry using the first image, the first inertial measurement, the second image, the second inertial measurement and the resting position of the tracker; and provide the Tracker Base Geometry for use in a localization procedure.

The computing unit may be configured to provide one of the Tracker Definition and the Tracker Assessment Parameter for use in a localization procedure.

The computing unit may be further configured to provide user instructions to move the sensor apparatus from the first vantage point to the second vantage point for display on a display unit.

The computing unit may be configured to calculate the Tracker Assessment Parameter and is further configured to provide the Tracker Assessment Parameter for display on a display unit. The system may further comprise the display unit to display the Tracker Assessment Parameter.

The system may further comprise the tracker.

The system may further comprise the optical sensor.

The system may further comprise the one or more inertial sensors.

There is provided a computer-implemented method comprising: receiving, by a computing unit, a first image of a tracker from an optical sensor at a first vantage point and a first inertial measurement from one or more inertial sensors, wherein the one or more inertial sensors are co-registered to the optical sensor and wherein the first image and first inertial measurement are obtained by the respective optical sensor and one or more inertial sensors when the tracker is at a resting position in a field of view of the optical sensor; receiving, but the computing unit, a second image of the tracker from the optical sensor at a second vantage point and a second inertial measurement from the one or more inertial sensors, wherein the second image and second inertial measurement are obtained by the respective optical sensor and one or more inertial sensors when the tracker is at the resting position in a field of view of the optical sensor; and calculating, by the computing unit, at least one of: a Tracker Definition using the first image, the second image and a difference in orientation in at least 2 DOF between the first vantage point and the second vantage point; and a Tracker Assessment Parameter using the first image, the second image, the difference in orientation in at least 2 DOF between the first vantage point and the second vantage point and a Static Tracker Definition.

The method may further comprise calculating the difference in orientation in at least 2 DOF between the first vantage point and the second vantage point using the first inertial measurement and the second inertial measurement.

There is provided a system comprising: a computer-readable storage device storing instructions and/or data which, when executed on a computing unit, configures the computing unit to: receive a first image of a tracker from an optical sensor at a first vantage point and a first inertial measurement from one or more inertial sensors, wherein the one or more inertial sensors are co-registered to the optical sensor and wherein the first image and first inertial measurement are obtained by the respective optical sensor and one or more inertial sensors when the tracker is at a resting position in a field of view of the optical sensor; and calculate a Tracker Assessment Parameter using the first image, the first inertial measurement, the resting position of the tracker, and a Static Tracker Definition.

The data stored by the computer readable storage device may comprise the Static Tracker Definition. The Static Tracker Definition may comprise a Static Tracker Base Geometry.

The computing unit may be further configured to provide the Tracker Assessment Parameter for use in a localization procedure.

The computing unit may be further configured to provide user instructions to capture the first image for display on a display unit.

The computing unit may be further configured to provide the Tracker Assessment Parameter for display on a display unit.

The system may further comprise a display unit to display the Tracker Assessment Parameter.

There is provided a computer-implemented method comprising: receiving, by a computing unit, a first image of a tracker from an optical sensor at a first vantage point and a first inertial measurement from one or more inertial sensors, wherein the one or more inertial sensors are co-registered to the optical sensor and wherein the first image and first inertial measurement are obtained by the respective optical sensor and one or more inertial sensors when the tracker is at a resting position in a field of view of the optical sensor; and calculating, by the computing unit, a Tracker Assessment Parameter using the first image, the first inertial measurement, the resting position of the tracker, and a Static Tracker Definition.

This document describes two systems—one for localization and the other for characterization. It is to be understood that these may be distinct systems that utilise the same hardware such as the camera to capture images and the computing unit to execute instructions. These systems may also be distinct units that use different hardware. It is also possible that these distinct systems communicate with each other to present a seamless user experience but optionally utilise the same hardware. Alternatively, the characterization system may be used separately from the localization system. For example, the characterization system may be used as part of quality control at a manufacturing site while manufacturing a localization system for use in a surgical setting. The hardware and software used to characterize the tracker may be completely distinct. Tracker characterization may be performed on an ad-hoc basis as part of routine maintenance of trackers, or may be performed prior to each localization procedure that uses a tracker.

In an embodiment to calculate a Tracker Definition, the sensor apparatus further comprises one or more an inertial sensors, in addition to the optical sensor. The inertial and optical sensors are co-registered to each other, i.e. the coordinate frame of the optical sensor (in which optical measurements are calculated) is known to the computing unit with respect to the coordinate frame of the inertial sensor (in which inertial measurements are calculated). This can be done through a suitable calibration method, several of which are known in the art. Each of the one or more inertial sensors may be an accelerometer, gyroscope, magnetometer, etc. As an example, this document describes the use of an accelerometer as the inertial sensor to provide inertial measurements with respect to gravity.

Figure 40A:
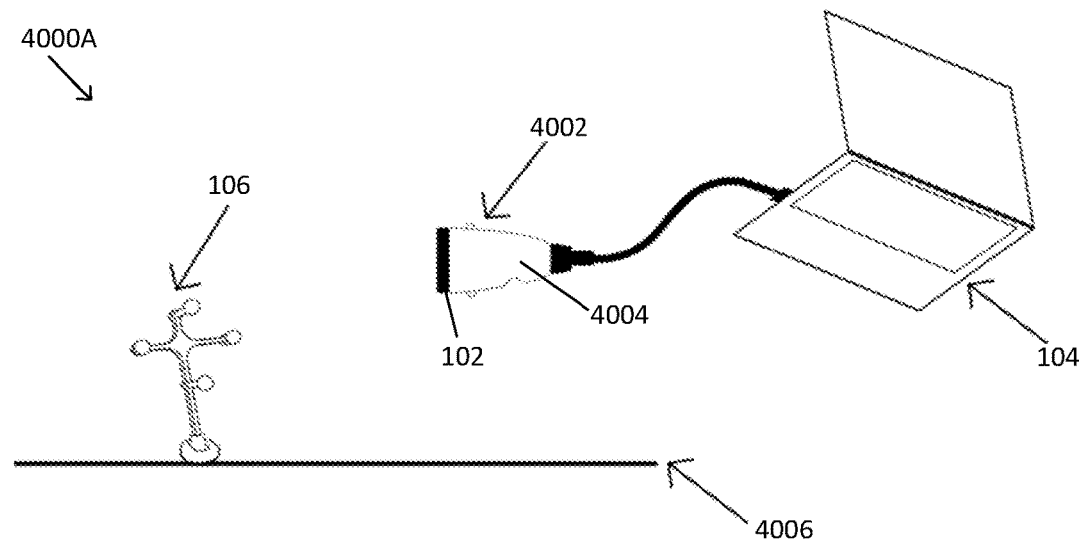
FIGS. 40A and 40B illustrating two configurations of a system using a sensor comprising a camera (optical sensor) and an accelerometer (inertial sensor)
Figure 40B:
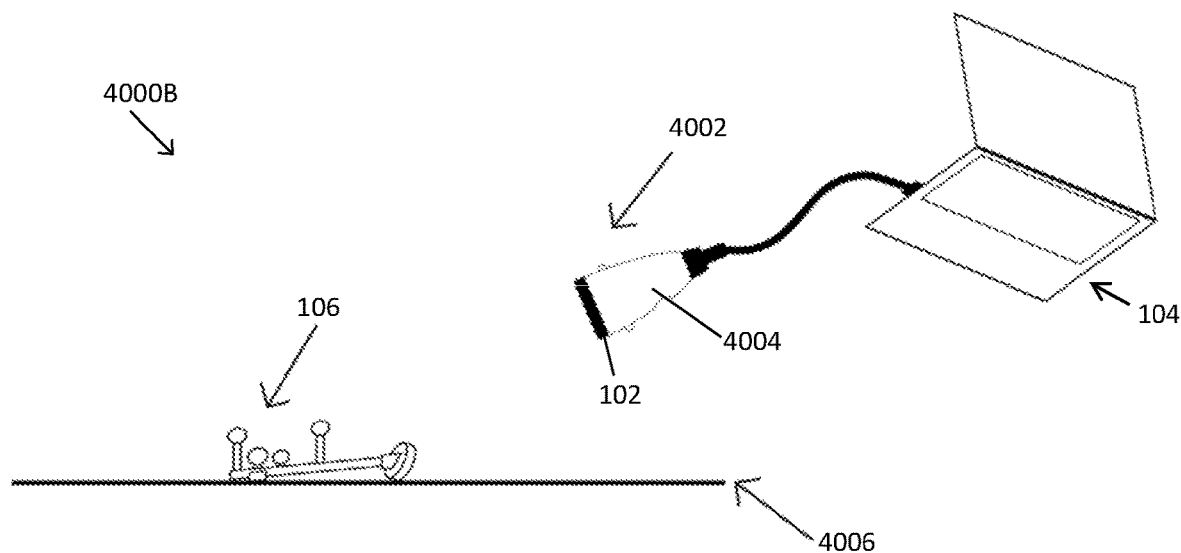

Reference is now made to FIGS. 40A and 40B illustrating two configurations of a system 4000A, 4000B using the sensor apparatus 4002 comprising a camera (optical sensor) 102 and an accelerometer (inertial sensor) 4004. The sensor apparatus 138 is connected to a computing unit 104. The sensor apparatus 138 may be handheld as it is moved to various vantage points around a tracker 106 such that the view of the tracker 106 is substantially different from each vantage point. A person skilled in the art will appreciate that the sensor apparatus 138 is moved steadily to each vantage point in order to avoid any unexpected and random movement introduced by a user that may affect the accuracy of measurements. From each vantage point, the computing unit 104 is provided image data and inertial measurements required for characterization. The tracker 106 is placed in a resting position such that an unoccluded view of the optically detectable features 108 of the tracker 106 is seen from the optical sensor 102. The tracker 106 must remain in the same resting position while multiple optical and inertial measurements are captured. A minimum of two images and two corresponding inertial measurements 4206 from two different vantage points are required for this configuration to calculate a Tracker Definition 806. However, a person skilled in the art will understand that multiple optical and inertial measurements may be used to improve accuracy. The inertial measurements 4206 are used as inputs into characterization operations 4204 to determine a difference in orientation in at least 2 DOF between the vantage points 4618, along with corresponding optical measurement at the same timestamp, in order to calculate a Tracker Definition 806 for the tracker 106.

If a Tracker Base Geometry is to be calculated, the tracker 106 may be placed in a known resting position with respect to the inertial measurement of gravity e.g.: tracker 106 may be placed upright on a rigid surface 4006 through its base as illustrated in FIG. 40A. Using the additional knowledge of the resting position of the tracker with respect to the inertial measurements 4206, the computing unit 104 may calculate the Tracker Base Geometry in addition to the Tracker Definition 806. In an alternative configuration illustrated in FIG. 40B, the tracker 106 is placed on a flat surface 4006 such that its optically detectable features are facing up.

Figure 41A:
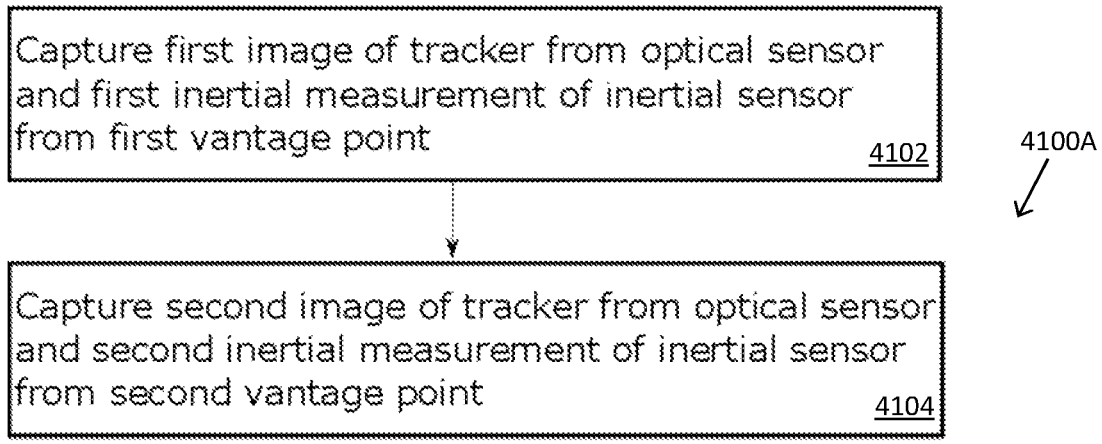
FIGS. 41A and 41B illustrate a user method and a corresponding computer implemented method to calculate a Tracker Definition.
Figure 41B:
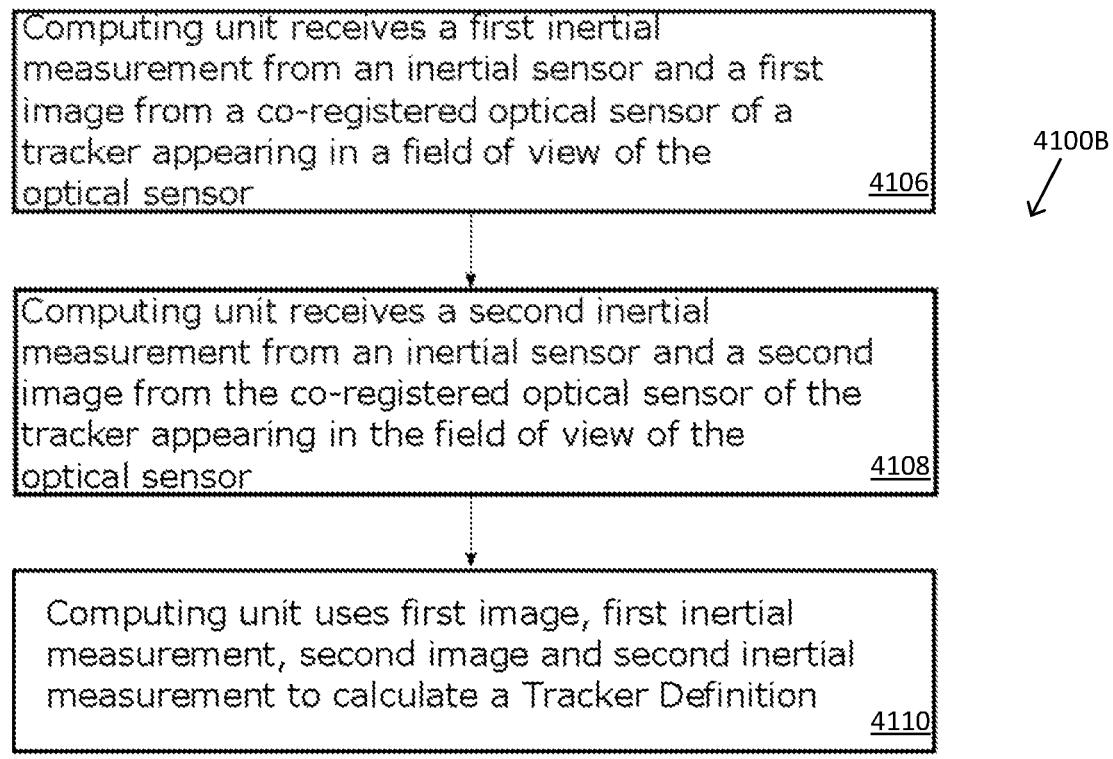

FIGS. 41A and 41B illustrate a user method 4100A and a corresponding computer implemented method 4100B to calculate a Tracker Definition 806. A workflow executing on the computing unit 104 instructs the user to capture a first image of a tracker 106 from an optical sensor 102 and a first inertial measurement from an inertial sensor 4004 co-registered with the optical sensor 102 from a first vantage point 4102. The user is then instructed to capture a second image of a tracker 106 from an optical sensor 102 and a second inertial measurement from an inertial sensor 4004 co-registered with the optical sensor 102 from a second vantage point 4104. The computing unit 104 executes instructions to receive the optical and inertial measurements from a co-registered optical sensor and inertial sensor 4106, 4108. Using the optical measurements in combination with a difference in orientation in at least 2 DOF between each vantage point derived from the inertial measurements, the computing unit 104 is able to calculate a Tracker Definition 806 for the tracker 106, 4110. This calculated Tracker Definition 806 comprises the spatial relationship between the optically detectable features 108 of the tracker.

Figure 42:
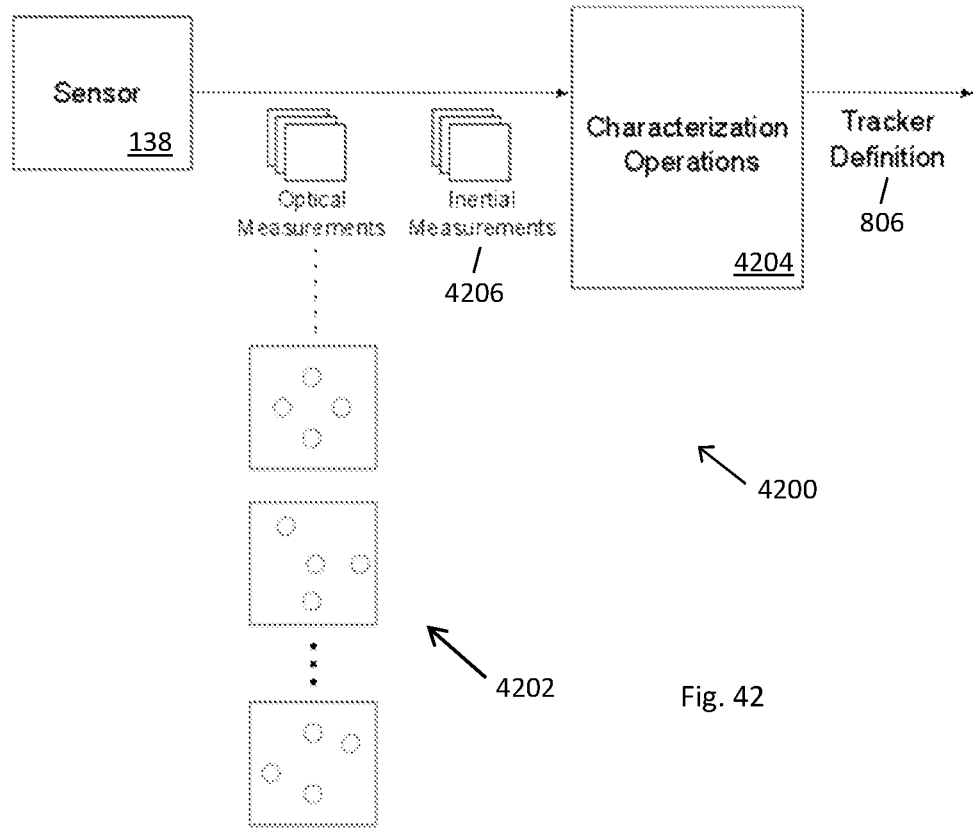
FIG. 42 illustrates a block diagram showing the inputs into a characterization operation to calculate a Tracker Definition.
Figure 43:
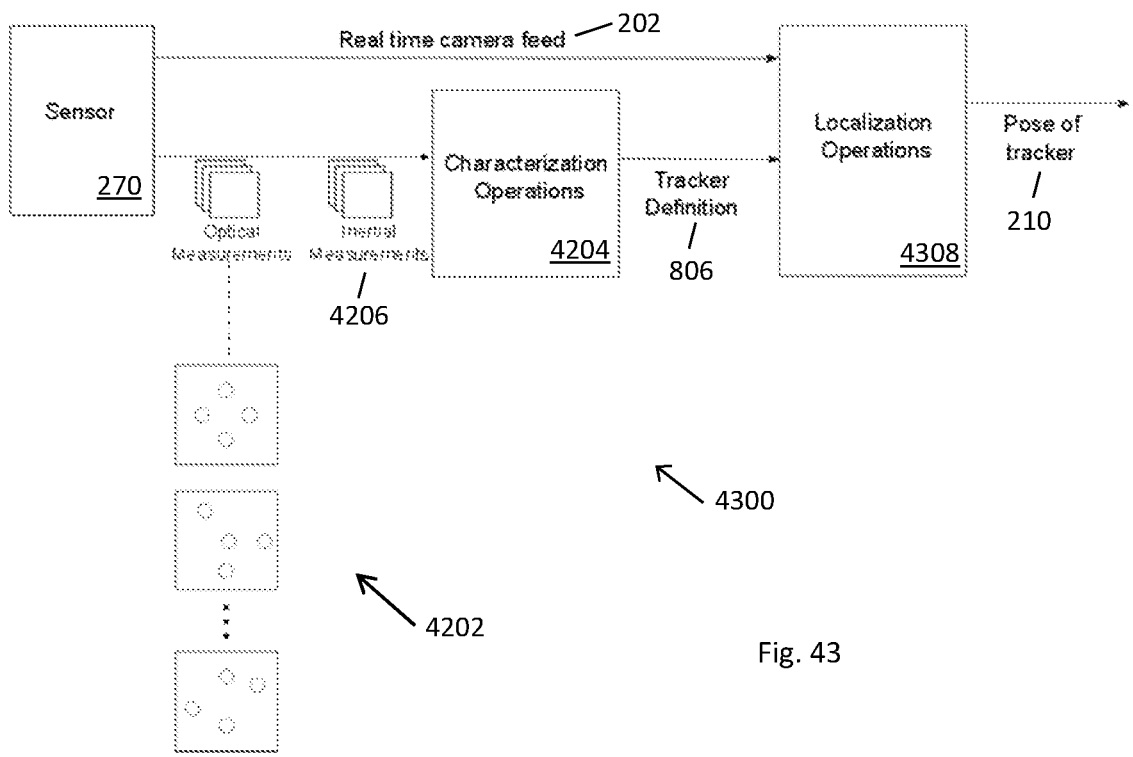
FIG. 43 illustrates a block diagram depicting the Tracker Definition being used in localization operations to calculate a pose of the tracker.

FIG. 42 illustrates a system 4200 using a block diagram to show the inputs into a characterization operation 4204 to calculate a Tracker Definition 806 comprising optical measurements 4202 and inertial measurement 4206 captured by a sensor apparatus 138 comprising an optical sensor 102 and an inertial sensor 4004. FIG. 43 further illustrates a system 4300 using a block diagram depicting the Tracker Definition 806 (and optionally, the Tracker Base Geometry) being used in localization operations 4308 to calculate a pose of the tracker 210. This diagram also illustrates the optical sensor 102 providing optical measurements 4202 for characterization operation 4204 and a real time feed of camera images 202 for localization operations 4308.

Figure 44:
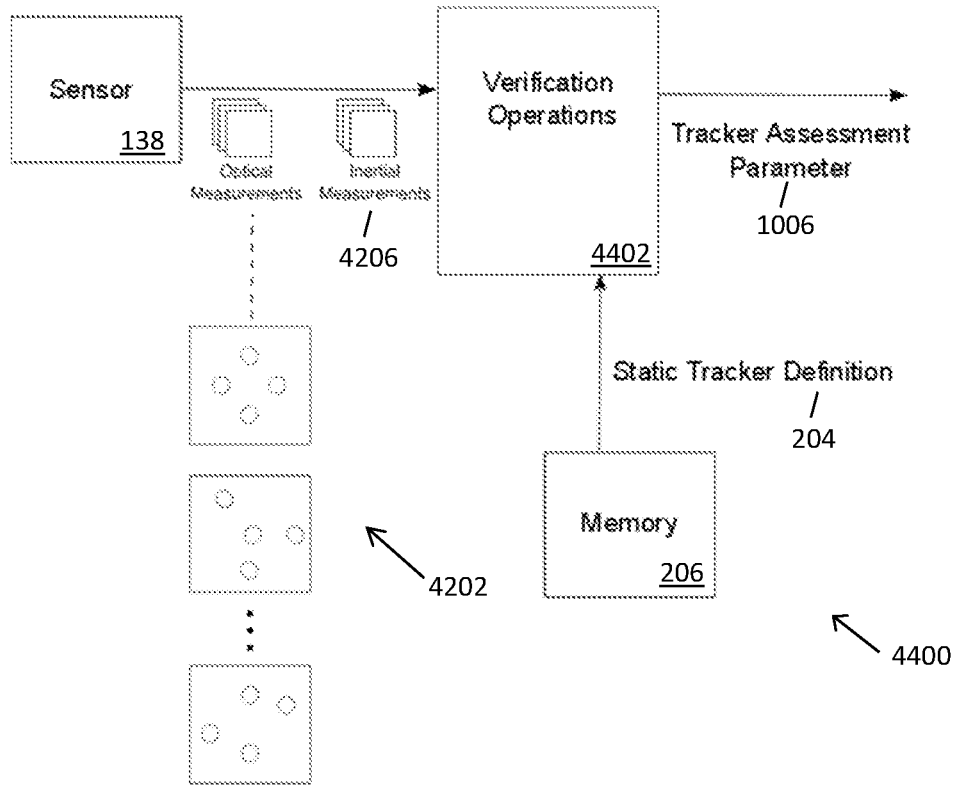
FIG. 44 illustrates a block diagram showing the inputs into a verification operation to calculate a Tracker Assessment Parameter to verify the accuracy of a tracker with respect to a Static Tracker Definition.

It is possible that for some surgical applications, deviation (e.g. by more than a threshold amount) of a tracker 106 from a Static Tracker Definition 204 is unacceptable. The system may generate a Tracker Assessment Parameter 1006 to quantify this deviation. This Tracker Assessment Parameter 1006 may then be used by the computing unit 104 during a localization procedure to determine whether the tracker 106 being used is accurate or not. Some of the examples of how the Tracker Assessment Parameter 1006 is presented could be a Boolean flag, a single numerical value or multiple numerical values associated with how closely the Tracker Definition 806 matches the Static Tracker Definition 204, etc. FIG. 44 illustrates a system 4400 as a block diagram to show the inputs into a verification operation 4402 to calculate the Tracker Assessment Parameter 1006 that is used to verify the accuracy of a tracker with respect to a Static Tracker Definition 204. The Tracker Assessment Parameter 1006 may simply be presented to the user (e.g.: on a display unit 1206) to allow the user to make further decisions. The accuracy of a tracker can be verified by comparing its calculated Tracker Definition 806 to a Static Tracker Definition 204. A tracker may also be verified by comparing actual optical measurements 4202 (in combination with a change in orientation in at least 2 DOF between each vantage point calculated using the inertial measurements 4206) with expected optical measurements calculated using a Static Tracker Definition 204, and further based on the change in orientation in at least 2 DOF between each vantage point 4618.

Figure 45:
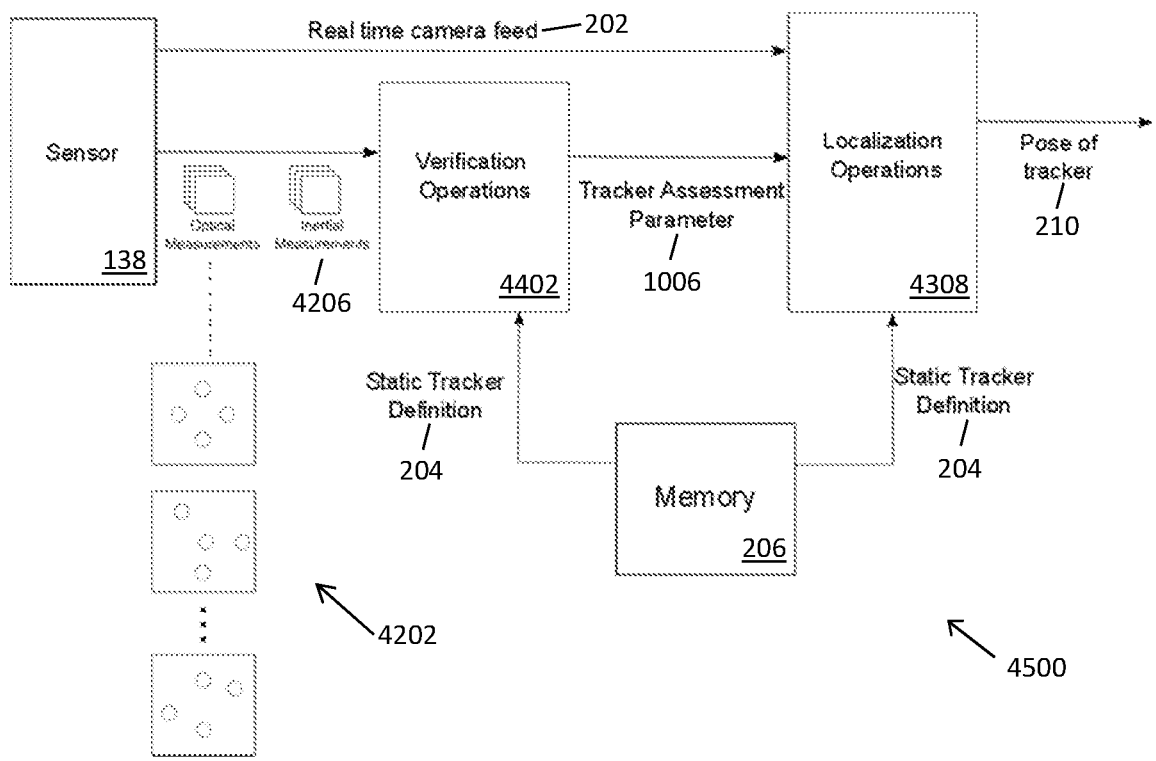
FIG. 45 illustrates a block diagram depicting the Tracker Assessment Parameter being used in localization operations to calculate a pose of the tracker.

In the exemplary configuration illustrated in FIG. 40A, the computing unit 104 may only require a single inertial measurement 4206, the corresponding optical measurement 4202, and the known resting position of the tracker 106 with respect to the inertial measurement 4206 to verify the accuracy of the tracker 106 with respect to the Static Tracker Definition 204. The computing unit 104 may further verify the accuracy of the tracker 106 with respect to a Static Tracker Base Geometry 2918, if provided. FIG. 45 illustrates a system as a block diagram depicting the Tracker Assessment Parameter 1006 being used in localization operations 7308 to calculate a pose of the tracker 210.

Figure 46:
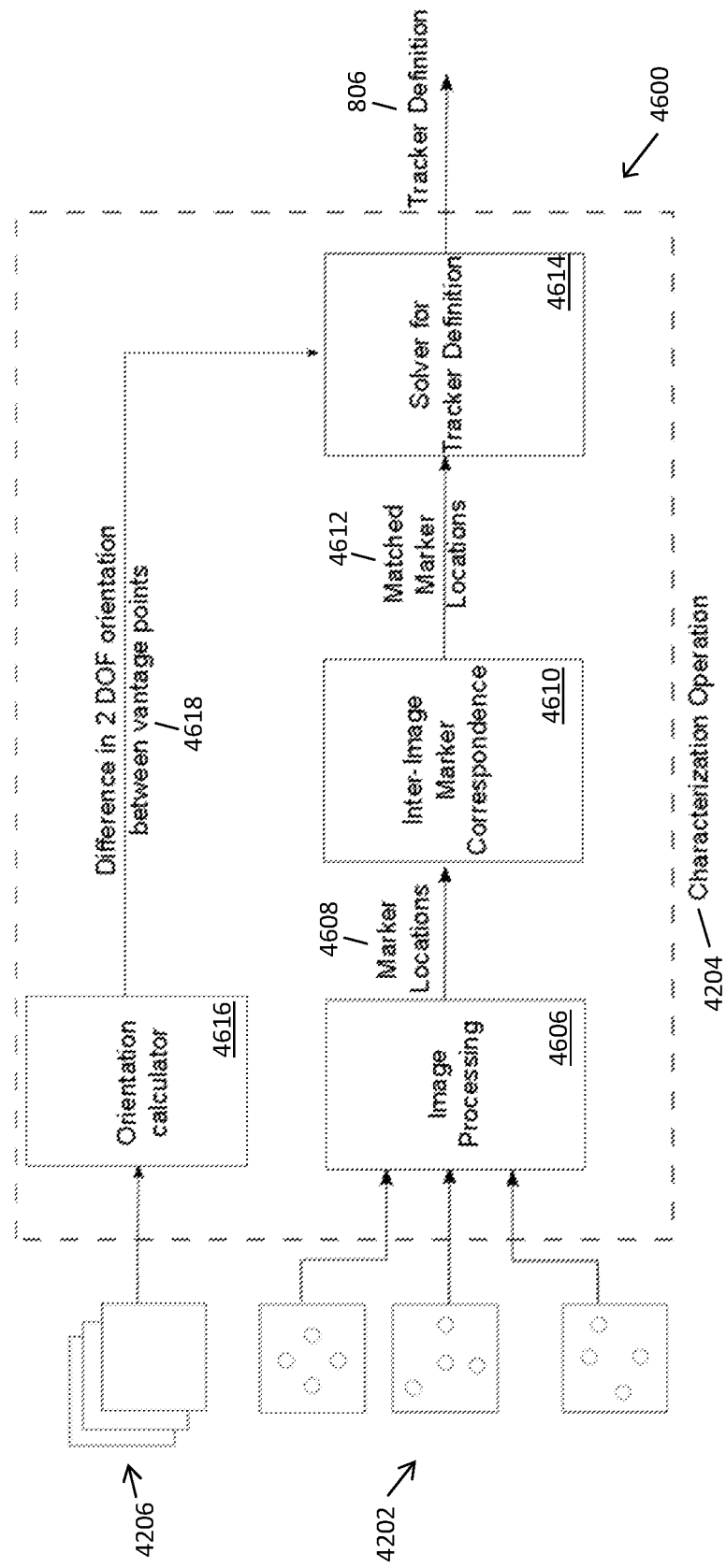
FIG. 46 depicts an exemplary characterization operation.

FIG. 46 depicts an exemplary method 4600 of the characterization operation 4204. The figure describes three stages of the characterization operation 4204. First, optical measurements 4202 (comprising multiple 2D images) are received from the optical sensor 102 and processed 4606 to identify the optically detectable features (e.g., markers) 108 of the tracker 106 in each image. The locations of each optically detectable feature, also called the marker locations 4608, in all the images 4202 are used in the next stage where the operations create a correspondence between an optically detectable feature of a first image and the same feature in a second image, and so on 4610. Meanwhile, the inertial measurements 4206 from the inertial sensor 4004 are used by the orientation calculator 4616 to calculate a difference in the orientation in at least 2 DOF between each vantage point from where a corresponding image was captured 4618. Using this difference and the matched marker locations 4612, the operation solves 4614 for a value for a Tracker Definition 806. Persons skilled in the art will understand that this is an exemplary operation, and that there may be a variety of operations that can be executed to perform such calculations.

Accordingly, it is to be understood that this subject matter is not limited to particular embodiments described, and as such may vary. It is also to be understood that the terminology used herein is for the purpose of describing particular embodiments only, and is not intended to be limiting.

As will be apparent to those of skill in the art upon reading this disclosure, each of the individual embodiments described and illustrated herein has discrete components and features which may be readily separated from or combined with the features of any of the other several embodiments without departing from the teachings herein. Any recited method can be carried out in the order of events recited or in any other order which is logically possible.

Various embodiments have been described herein with reference to the accompanying drawings. It will, however, be evident that various modifications and changes may be made thereto, and additional embodiments may be implemented, without departing from the broader scope of the disclosed embodiments as set forth in the claims that follow.

What is claimed is:

1. A computer implemented method comprising the steps of:
    receiving, by a computing unit, and from an optical sensor, a set of images of a tracker, the set of images showing a plurality of optical features of the tracker from a variety of vantage points; and
    calculating, by the computing unit, at least one of: a tracker definition and a tracker assessment parameter;
    wherein the calculating comprises, for each same feature of the plurality of optical features, creating a respective location correspondence for the same feature in each of the set of images.

2. The method of claim 1 wherein calculating comprises performing an optimization for each respective location correspondence.

3. The method of claim 1, wherein the tracker assessment parameter is calculated using a static tracker definition.

4. The method of claim 1 further comprising providing, by the computing unit, at least one of the tracker definition and the tracker assessment parameter as calculated for use in a localization procedure.

5. The method of claim 1 wherein the set of images comprises a first set of articulation images of the tracker when attached to a first tracker mounting location and a second set of articulation images of the tracker when attached to a second tracker mounting location.

6. The method of claim 5 wherein:
    the first tracker mounting location and the second tracker mounting location are respective tracker mounting locations on a characterization jig;
    the characterization jig comprises a base, the respective tracker mounting locations and a pivot leg, the pivot leg having a first end that attaches the pivot leg to the characterization jig and a second end that has a pivot point;
    the first set of articulation images are generated as the characterization jig is pivoted about the pivot point while the pivot point is mated with a first mating member of a surface; and
    the second set of articulation images are generated as the characterization jig is pivoted about the pivot point while the pivot point is mated with a second mating member of the surface.

7. The method of claim 6 wherein the optical sensor is separately coupled to the surface independently of the characterization jig.

8. The method of claim 6 wherein each of the first set of articulation images and the second set of articulation images comprise at least four distinct images of optically detectable features of the tracker.

9. The method of claim 6 wherein the step of calculating uses a known, fixed spatial relationship between the first tracker mounting location and the second tracker mounting location.

10. The method of claim 6 wherein the characterization jig comprises an identifier to identify a spatial relationship between the first tracker mounting location and the second tracker mounting location of the characterization jig for use to perform the calculating.

11. The method of claim 10 comprising receiving the identifier, by the computing unit via the optical sensor.

12. A system comprising:
    a computer-readable storage device storing instructions and/or data which, when executed on a computing unit, configures the computing unit to:
        receive, from an optical sensor, a set of images of a tracker, the set of images showing a plurality of optical features of the tracker from a variety of vantage points; and
        calculate at least one of: a tracker definition and a tracker assessment parameter; and
        providing at least one of the tracker definition and the tracker assessment parameter as calculated for use in a localization procedure; and
        wherein to calculate comprises, for each same feature of the plurality of optical features, creating a respective location correspondence for the same feature in each of the set of images.

13. The system of claim 12 wherein to calculate comprises performing an optimization for each respective location correspondence.

14. The system of claim 12, wherein the tracker assessment parameter is calculated using a static tracker definition.

15. The system of claim 12 wherein the set of images comprises a first set of articulation images of the tracker when attached to a first tracker mounting location and a second set of articulation images of the tracker when attached to a second tracker mounting location.

16. The system of claim 15 comprising a characterization jig, the jig comprising a base, respective tracker mounting locations and a pivot leg, the pivot leg having a first end that attaches the pivot leg to the characterization jig and a second end that has a pivot point; and
  wherein:
    the first tracker mounting location and the second tracker mounting location comprise respective tracker mounting locations on the characterization jig;
    the first set of articulation images are generated as the characterization jig is pivoted about the pivot point while the pivot point is mated with a first mating member of a surface; and
    the second set of articulation images are generated as the characterization jig is pivoted about the pivot point while the pivot point is mated with a second mating member of the surface.

17. The system of claim 16 wherein the optical sensor is separately coupled to the surface independently of the characterization jig.

18. The system of claim 16 wherein each of the first set of articulation images and the second set of articulation images comprise at least four distinct images of optically detectable features of the tracker.

19. The system of claim 16 wherein the step of calculating uses a known, fixed spatial relationship between the first tracker mounting location and the second tracker mounting location.

20. The system of claim 16 wherein the pivot leg and at least one of the first mating member and the second mating member may further comprise a magnetic component to allow a magnetic connection therebetween.

21. The system of claim 16 wherein the first mating member and second mating member are coincident on the surface.

22. The system of claim 16 wherein the surface comprises a sterilization tray surface of a sterilization tray containing medical instruments for use in a surgical procedure.

23. The system of claim 16 wherein the first end of the pivot leg comprises a hinge joint movable in one degree of freedom and coupled to a bottom side of the characterization jig, the bottom side forming a slot to accommodate a length of the pivot leg.

24. The system of claim 12 further comprising any of the tracker, the optical sensor; the computing unit and a display unit.

* * * * *